US012723080B2

(12) United States Patent
Li et al.

(10) Patent No.: US 12,723,080 B2
(45) Date of Patent: Sep. 1, 2026

(54) MONOCLONAL ANTIBODY-CYTOKINE FUSION PROTEIN DIMER AND APPLICATION THEREOF

(71) Applicant: Nanjing GenScript Biotech Co., Ltd., Nanjing (CN)

(72) Inventors: Zhongdao Li, Nanjing (CN); Liusong Yin, Nanjing (CN); Zhenyu Liu, Nanjing (CN); Tielin Zhou, Singapore (SG); Zhuo Fang, Nanjing (CN)

(73) Assignee: Nanjing GenScript Biotech Co., Ltd., Nanjing (CN)

(*) Notice: Subject to any disclaimer, the term of this patent is extended or adjusted under 35 U.S.C. 154(b) by 1303 days.

(21) Appl. No.: 17/617,156

(22) PCT Filed: Jun. 24, 2020

(86) PCT No.: PCT/CN2020/097927

§ 371 (c)(1),
(2) Date: Dec. 7, 2021

(87) PCT Pub. No.: WO2020/259536

PCT Pub. Date: Dec. 30, 2020

(65) Prior Publication Data

US 2022/0235133 A1 Jul. 28, 2022

(30) Foreign Application Priority Data

Jun. 24, 2019 (CN) ......................... 201910549915.0

(51) Int. Cl.

| | |
|---|---|
| ***C07K 16/28*** | (2006.01) |
| ***A61K 39/00*** | (2006.01) |
| ***A61K 47/68*** | (2017.01) |
| ***A61P 35/00*** | (2006.01) |
| ***C07K 14/54*** | (2006.01) |
| ***C07K 14/55*** | (2006.01) |

(52) U.S. Cl.

CPC ...... *C07K 16/2818* (2013.01); *A61K 47/6813* (2017.08); *A61P 35/00* (2018.01); *C07K 14/544* (2013.01); *C07K 14/55* (2013.01); *C07K 16/2827* (2013.01); *A61K 2039/505* (2013.01)

(58) Field of Classification Search

None

See application file for complete search history.

(56) References Cited

U.S. PATENT DOCUMENTS

| | | | | |
|---|---|---|---|---|
| 6,617,135 | B1 | 9/2003 | Gillies et al. | |
| 11,970,537 | B2 * | 4/2024 | Li ...................... | A61K 47/6813 |
| 2012/0276125 | A1 * | 11/2012 | Ast .................... | C07K 16/2866 435/69.6 |
| 2018/0326010 | A1 | 11/2018 | Deak et al. | |
| 2018/0326011 | A1 | 11/2018 | Deak et al. | |

FOREIGN PATENT DOCUMENTS

| | | | |
|---|---|---|---|
| CN | 1382158 | A | 11/2002 |
| CN | 105377889 | A | 3/2016 |
| EP | 1731531 | B1 | 5/2012 |
| WO | WO 2014/145806 | A2 | 9/2014 |
| WO | WO 2019/010219 | A1 | 1/2019 |

OTHER PUBLICATIONS

Ni et al., The Protein Journal, 43, pp. 683-696, Jul. 2024 (Year: 2024).*

Hutmacher and Neri, "Antibody-cytokine fusion proteins: Biopharmaceuticals with immunomodulatory properties for cancer therapy," *Adv Drug Deliv Rev.* 141:67-91, 2018.

International Search Report and Written Opinion mailed on Sep. 28, 2020 in International Application No. PCT/CN2020/097927 (10 pages).

English translation of International Search Report and Written Opinion mailed on Sep. 28, 2020 in International Application No. PCT/CN2020/097927 (4 pages).

Extended European Search Report for EP20832735.3, issued by the European Patent Office, mailed on Jul. 11, 2023, 8 pages.

Jahn et al., "An IL12-IL2-Antibody Fusion Protein Targeting Hodgkin's Lymphoma Cells Potentiates Activation of NK and T cells for an Anti-Tumor Attack", *PLOS ONE*, vol. 7, No. 9, e44482, Sep. 18, 2012, 13 pages.

* cited by examiner

*Primary Examiner* — Peter J Reddig
*Assistant Examiner* — Cheng Lu
(74) *Attorney, Agent, or Firm* — Yong Chen; Lin Sun-Hoffman; Liu Chen & Hoffman LLP

(57) ABSTRACT

Provided are a monoclonal antibody-cytokine fusion protein dimer and an application thereof. The monoclonal antibody comprises two heavy chains, the fusion protein dimer comprises a first heavy chain polypeptide chain and a second heavy chain polypeptide chain, wherein one heavy chain of the monoclonal antibody is connected to a cytokine to form the first heavy chain polypeptide chain, and the other heavy chain of the monoclonal antibody is optionally connected to another cytokine to form the second heavy chain polypeptide chain. The monoclonal antibody-cytokine fusion protein dimer provided not only fully retains the biological activity of the antibody, but also significantly improves the biological activity of the cytokine(s). More importantly, by using the target specificity of the antibody molecule, the immune response of immune cells is enhanced and the toxicity of the cytokine(s) is reduced, and thus, on the premise of enhancing the efficacy of the drug, the safety of the medication is ensured.

16 Claims, 7 Drawing Sheets

Specification includes a Sequence Listing.

| | mLAG301 | IL-2 | mLAG303 |
|---|---|---|---|
| EC50 | 37.06 | 78.14 | 18.45 |

| | mPDL101 | mPDL103 | IL-2 |
|---|---|---|---|
| EC50 | 18.68 | 16.77 | 78.14 |

0.6
0.4
0.2
0.0
Net OD 490
$10^{-1}$ $10^{0}$ $10^{1}$ $10^{2}$ $10^{3}$ $10^{4}$
IL-2 (pmol/l)
mTIGIT01
mTIGIT03
IL-2

| | mTIGIT01 | mTIGIT03 | IL-2 |
|---|---|---|---|
| EC50 | 32.56 | 52.55 | 78.14 |

| | mPD103 | mPD101 | IL-2 |
|---|---|---|---|
| EC50 | 52.38 | 53.69 | 62.35 |

| IL-12 | mLAG301 | mLAG302 |
|---|---|---|
| 7.388 | 4.661 | 7.238 |

| mPDL101 | mPDL102 | IL-12 |
|---|---|---|
| 8.216 | 1.221 | 8.845 |

mTIGIT01
IL-12
mTIGIT02
Net OD(450nm-570nm)
IL-12 (pmol/l)

| mTIGIT01 | IL-12 | mTIGIT02 |
|---|---|---|
| 12.08 | 7.412 | 5.443 |

| | mPD101 | IL-12 | mPD102 |
|---|---|---|---|
| EC50 | 0.2423 | 2.083 | 1.558 |

| | mLAG301 | mLAG302 | mLAG303 | mLAG300 |
|---|---|---|---|---|
| EC50 | 1.276 | 1.074 | 2.991 | 3.034 |

| | mPDL100 | mPDL101 | mPDL102 | mPDL103 |
|---|---|---|---|---|
| EC50 | 0.3291 | 0.5879 | 0.4798 | 0.5701 |

| | mTIGIT01 | mTIGIT02 | mTIGIT03 | mTIGIT00 |
|---|---|---|---|---|
| EC50 | 22.32 | 20.20 | 30.87 | 27.61 |

| | mPD101 | mPD100 | mPD102 | mPD103 |
|---|---|---|---|---|
| EC50 | 3.717 | 1.826 | 2.707 | 2.340 |

SEQUENCE LISTING

```
<160> NUMBER OF SEQ ID NOS: 71

<210> SEQ ID NO 1
<211> LENGTH: 57
<212> TYPE: DNA
<213> ORGANISM: Artificial Sequence
<220> FEATURE:
<223> OTHER INFORMATION: DNA sequence of signal peptide

<400> SEQUENCE: 1

atgggatggt cttggatcct gctgttcctg ctgagcgtga cagctggcgt gcactct        57


<210> SEQ ID NO 2
<211> LENGTH: 19
<212> TYPE: PRT
<213> ORGANISM: Artificial Sequence
<220> FEATURE:
<223> OTHER INFORMATION: Amino acid sequence of signal peptide

<400> SEQUENCE: 2

Met Gly Trp Ser Trp Ile Leu Leu Phe Leu Leu Ser Val Thr Ala Gly
1               5                   10                  15

Val His Ser


<210> SEQ ID NO 3
```

<211> LENGTH: 1554
<212> TYPE: DNA
<213> ORGANISM: Artificial Sequence
<220> FEATURE:
<223> OTHER INFORMATION: DNA sequence of cytokine IL-12

<400> SEQUENCE: 3

```
atttgggagc tgaagaaaga cgtgtacgtg gtcgagctgg actggtaccc tgatgcccca     60
ggcgagatgg tcgtgctgac ctgcgataca ccagaggaag atggtatcac ctggacactg    120
gatcagtcct cagaggtgct gggctctggt aaaacactga ccattcaggt gaaggagttc    180
ggtgacgctg gacagtacac ttgtcataag ggcggggagg tgctgtctca ctccctgctg    240
ctgctgcata agaaggagga tggaatctgg tccactgaca tcctgaaaga ccagaaggag    300
ccaaagaaca aaaccttcct gcgatgcgag gctaagaact acagcggccg ctttacatgc    360
tggtggctga caaccatcag caccgatctg acctttagcg tgaagtcatc caggggcagt    420
tcagaccctc agggagtcac atgtggcgcc gcaaccctgt cagcagagcg agtgcgggga    480
gacaataagg aatacgagta cagcgtcgag tgtcaggagg attccgcatg tccagctgca    540
gaagaatccc tgcctatcga agtcatggtg gacgctgtgc ataaactgaa gtacgagaat    600
tacaccagca gctttttcat ccgggacatc atcaagcccg atccacctaa gaatctgcag    660
ctgaagcctc tgaaaaatag ccgacaggtc gaagtgtcat gggaataccc agacacctgg    720
tcaacaccac actcctactt ctccctgacc ttctgtgtgc aggtccaggg aaaaagcaag    780
cgggaaaaga aagatcgggt gttcaccgac aagaccagtg ctacagtgat ttgccggaag    840
aatgccagca tttctgtcag agctcaggac cggtactata gctcttcctg gagcgagtgg    900
gcttcagtgc catgttctgg aggcggtgga tctggcggag gtggaagcgg aggcggtgga    960
tctagaaacc tgcccgtcgc aacccctgat ccagggatgt tcccctgtct gcatcacagc   1020
cagaatctgc tgagggctgt ctccaacatg ctgcagaagg ctcgacagac cctggagttc   1080
tacccatgta ccagcgaaga gatcgaccac gaggatatca caaaggataa aaccagcaca   1140
gtggaagcat gcctgcctct ggaactgacc aagaatgaga gctgcctgaa tagcagggag   1200
acctccttca tcaccaacgg ctcatgcctg gcttcaagga agaccagctt catgatggct   1260
ctgtgtctga gctctatcta tgaggacctg aagatgtacc aggtggagtt caagaccatg   1320
aacgccaagc tgctgatgga tccaaagagg cagatcttcc tggatcagaa tatgctggca   1380
gtgatcgatg agctgatgca ggccctgaat tttaacagtg agacagtgcc tcagaagagc   1440
tctctggaag agccagactt ttacaaaact aagatcaagc tgtgcattct gctgcacgct   1500
ttccgcatca gagctgtcac tatcgataga gtgatgagct atctgaatgc ctca         1554
```

<210> SEQ ID NO 4
<211> LENGTH: 518
<212> TYPE: PRT
<213> ORGANISM: Artificial Sequence
<220> FEATURE:
<223> OTHER INFORMATION: Amino acid sequence of cytokine IL-12 full-length

<400> SEQUENCE: 4

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45
```

-continued

```
Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460
```

```
Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser
        515


<210> SEQ ID NO 5
<211> LENGTH: 399
<212> TYPE: DNA
<213> ORGANISM: Artificial Sequence
<220> FEATURE:
<223> OTHER INFORMATION: DNA sequence of cytokine IL-2

<400> SEQUENCE: 5

gcacctactt caagttctac aaagaaaaca cagctacaac tggagcattt actgctggat     60

ttacagatga ttttgaatgg aattaataat tacaagaatc ccaaactcac caggatgctc    120

acatttaagt tttacatgcc caagaaggcc acagaactga aacatcttca gtgtctagaa    180

gaagaactca aacctctgga ggaagtgcta aatttagctc aaagcaaaaa ctttcactta    240

agacccaggg acttaatcag caatatcaac gtaatagttc tggaactaaa gggatctgaa    300

acaacattca tgtgtgaata tgctgatgag acagcaacca ttgtagaatt tctgaacaga    360

tggattacct tttgtcaaag catcatctca acactgact                           399


<210> SEQ ID NO 6
<211> LENGTH: 133
<212> TYPE: PRT
<213> ORGANISM: Artificial Sequence
<220> FEATURE:
<223> OTHER INFORMATION: Amino acid sequence of Cytokine IL-2

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 7
<211> LENGTH: 1338
<212> TYPE: DNA
<213> ORGANISM: Artificial Sequence
<220> FEATURE:
```

<223> OTHER INFORMATION: DNA sequence of polypeptide chain H1

<400> SEQUENCE: 7

```
caagtgcagc tgcagcagtg gggcgctggc ctgctgaagc cttccgagac actgtctctg      60
acctgtgctg tttacggcgg ctccttctcc gactactact ggaactggat cagacagcct     120
cctggcaagg gcctggaatg gatcggcgag atcaaccaca gaggctctac caactccaac     180
ccatctctga agtccagagt gacactgagt ctggacacct ctaagaatca gttctccctg     240
aagctgagat ctgtgaccgc cgccgacacc gctgtgtact actgcgcctt cggctactcc     300
gactatgaat acaactggtt cgacccttgg ggccagggca ccctggtgac cgtgagctct     360
gcttccacaa aaggccctag cgtgtttcct ctggcccctt gctccagatc cacttctgag     420
tccaccgctg ctctcggctg cctggtgaag gactacttcc ccgaacccgt caccgtgtcc     480
tggaacagcg gcgccttgac ctccggcgtg cacaccttcc ctgccgtgct gcagagtagc     540
ggactgtata gcctgtccag cgtcgtgacc gtgccttcct cttccctggg cacaaagaca     600
tacacctgca acgtggacca caagccctct aacaccaaag tggataagcg ggtagagtcc     660
aagtacggcc ccccttgccc tccttgtcct gctcctgagt tcctgggagg cccttctgtg     720
tttctgttcc cccccaaacc taaggatacc ctgatgatct ctcggacccc tgaggtgacc     780
tgcgtggtgg tggacgtgtc acaagaggat cctgaagtgc agtttaattg gtacgtggac     840
ggcgtggaag tgcataacgc caaaaccaaa ccacgcgaag aacagttcaa ctccacctac     900
agagtcgtca gcgtgctgac cgtgctgcac caggattggc tgaacggcaa ggagtacaag     960
tgcaaggtgt ccaacaaggg actgccttct tccatcgaga agaccatctc caaggccaag    1020
ggccagcctc gggagcctca ggtgtacacc ctccctccat cccaggaaga gatgaccaag    1080
aaccaggtgt ccctgacctg tctggtcaag ggcttctacc cctctgacat cgccgtggag    1140
tgggagtcta atggccaacc cgagaacaac tacaagacca cccctccagt gctggactct    1200
gatggatctt tcttcctgta ctcccggctg acagtggaca agagcagatg gcaggaaggc    1260
aacgtgttct cctgctccgt gatgcacgag gccctgcata accactatac ccagaagtct    1320
ctgtctctgt ctctggga                                                  1338
```

<210> SEQ ID NO 8
<211> LENGTH: 446
<212> TYPE: PRT
<213> ORGANISM: Artificial Sequence
<220> FEATURE:
<223> OTHER INFORMATION: Amino acid sequence of polypeptide chain H1

<400> SEQUENCE: 8

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
```

-continued

```
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 9
<211> LENGTH: 642
<212> TYPE: DNA
<213> ORGANISM: Artificial Sequence
<220> FEATURE:
<223> OTHER INFORMATION: DNA sequence of polypeptide chain L1

<400> SEQUENCE: 9

gagatcgtgc tgacccagtc ccccgccact ttgtctctgt ctcctggcga gagagctacc      60

ctgtcctgca gagcctctca gtccatctct tcctacctgg cctggtacca gcagaaacct     120
```

```
ggacaggctc ctcggctgct gatctacgac gcttctaatc gcgctacagg catccctgct    180

agattctccg gctctggctc cggcaccgat tttaccctga ccatctccag cctcgagccc    240

gaagattttg ccgtgtacta ctgccagcag cggtccaact ggcctctgac cttcggccag    300

ggaacaaacc tggaaatcaa gcggaccgtg gccgccccta gcgtcttcat cttccctcct    360

tccgacgaac aactgaagtc tggcaccgct agcgtggtgt gcctgctgaa caacttctac    420

cccagagagg ccaaagtgca gtggaaggtg gacaacgccc tgcagtctgg caactcccaa    480

gagtccgtga ccgagcagga ctccaaggac tctacctatt ccctgtcttc tacactgacc    540

ctgagcaagg ccgactacga gaagcacaag gtgtacgcct gcgaggtgac ccaccagggc    600

ctgtccagcc cagtcaccaa gtccttcaac agaggcgaat gt                       642


<210> SEQ ID NO 10
<211> LENGTH: 214
<212> TYPE: PRT
<213> ORGANISM: Artificial Sequence
<220> FEATURE:
<223> OTHER INFORMATION: Amino acid sequence of polypeptide chain L1

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 11
<211> LENGTH: 1338
<212> TYPE: DNA
<213> ORGANISM: Artificial Sequence
<220> FEATURE:
<223> OTHER INFORMATION: DNA sequence of polypeptide chain H2

<400> SEQUENCE: 11
```

```
caagtgcagc tgcagcagtg gggcgctggc ctgctgaagc cttccgagac actgtctctg     60

acctgtgctg tttacggcgg ctccttctcc gactactact ggaactggat cagacagcct    120

cctggcaagg gcctggaatg gatcggcgag atcaaccaca gaggctctac caactccaac    180

ccatctctga agtccagagt gacactgagt ctggacacct ctaagaatca gttctccctg    240

aagctgagat ctgtgaccgc cgccgacacc gctgtgtact actgcgcctt cggctactcc    300

gactatgaat acaactggtt cgacccttgg ggccagggca ccctggtgac cgtgagctct    360

gcttccacaa aaggccctag cgtgtttcct ctggcccctt gctccagatc cacttctgag    420

tccaccgctg ctctcggctg cctggtgaag gactacttcc ccgaacccgt caccgtgtcc    480

tggaacagcg gcgccttgac ctccggcgtg cacaccttcc ctgccgtgct gcagagtagc    540

ggactgtata gcctgtccag cgtcgtgacc gtgccttcct cttccctggg cacaaagaca    600

tacacctgca acgtggacca caagccctct aacaccaaag tggataagcg ggtagagtcc    660

aagtacggcc ccccttgccc tccttgtcct gctcctgagt tcctgggagg cccttctgtg    720

tttctgttcc cccccaaacc taaggatacc ctgatgatct ctcggacccc tgaggtgacc    780

tgcgtggtgg tggacgtgtc acaagaggat cctgaagtgc agtttaattg gtacgtggac    840

ggcgtggaag tgcataacgc caaaaccaaa ccacgcgaag aacagttcaa ctccacctac    900

agagtcgtca gcgtgctgac cgtgctgcac caggattggc tgaacggcaa ggagtacaag    960

tgcaaggtgt ccaacaaggg actgccttct tccatcgaga agaccatctc caaggccaag   1020

ggccagcctc gggagcctca ggtgtacacc ctccctccat gccaggaaga gatgaccaag   1080

aaccaggtgt ccctgtggtg tctggtcaag ggcttctacc cctctgacat cgccgtggag   1140

tgggagtcta atggccaacc cgagaacaac tacaagacca cccctccagt gctggactct   1200

gatggatctt tcttcctgta ctcccggctg acagtggaca agagcagatg gcaggaaggc   1260

aacgtgttct cctgctccgt gatgcacgag gccctgcata accactatac ccagaagtct   1320

ctgtctctgt ctctggga                                                 1338
```

<210> SEQ ID NO 12
<211> LENGTH: 446
<212> TYPE: PRT
<213> ORGANISM: Artificial Sequence
<220> FEATURE:
<223> OTHER INFORMATION: Amino acid sequence of polypeptide chain H2

<400> SEQUENCE: 12

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
```

```
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 13
<211> LENGTH: 1338
<212> TYPE: DNA
<213> ORGANISM: Artificial Sequence
<220> FEATURE:
<223> OTHER INFORMATION: DNA sequence of polypeptide chain H3

<400> SEQUENCE: 13

caagtgcagc tgcagcagtg gggcgctggc ctgctgaagc cttccgagac actgtctctg      60

acctgtgctg tttacggcgg ctccttctcc gactactact ggaactggat cagacagcct     120

cctggcaagg gcctggaatg gatcggcgag atcaaccaca gaggctctac caactccaac     180

ccatctctga agtccagagt gacactgagt ctggacacct ctaagaatca gttctccctg     240
```

```
aagctgagat ctgtgaccgc cgccgacacc gctgtgtact actgcgcctt cggctactcc    300

gactatgaat acaactggtt cgacccttgg ggccagggca ccctggtgac cgtgagctct    360

gcttccacaa aggccctag cgtgtttcct ctggcccctt gctccagatc cacttctgag    420

tccaccgctg ctctcggctg cctggtgaag gactacttcc ccgaacccgt caccgtgtcc    480

tggaacagcg gcgccttgac ctccggcgtg cacaccttcc ctgccgtgct gcagagtagc    540

ggactgtata gcctgtccag cgtcgtgacc gtgccttcct cttccctggg cacaaagaca    600

tacacctgca acgtggacca caagccctct aacaccaaag tggataagcg ggtagagtcc    660

aagtacggcc cccccttgccc tccttgtcct gctcctgagt tcctgggagg cccttctgtg    720

tttctgttcc cccccaaacc taaggatacc ctgatgatct ctcggacccc tgaggtgacc    780

tgcgtggtgg tggacgtgtc acaagaggat cctgaagtgc agtttaattg gtacgtggac    840

ggcgtggaag tgcataacgc caaaaccaaa ccacgcgaag aacagttcaa ctccacctac    900

agagtcgtca gcgtgctgac cgtgctgcac caggattggc tgaacggcaa ggagtacaag    960

tgcaaggtgt ccaacaaggg actgccttct tccatcgaga agaccatctc caaggccaag   1020

ggccagcctc gggagcctca ggtgtgtacc ctccctccat cccaggaaga gatgaccaag   1080

aaccaggtgt ccctgtcctg tgctgtcaag ggttctacc cctctgacat cgccgtggag    1140

tgggagtcta atggccaacc cgagaacaac tacaagacca cccctccagt gctggactct   1200

gatggatctt tcttcctggt gtcccggctg acagtggaca agagcagatg gcaggaaggc   1260

aacgtgttct cctgctccgt gatgcacgag gccctgcata accactatac ccagaagtct   1320

ctgtctctgt ctctggga                                                 1338
```

<210> SEQ ID NO 14
<211> LENGTH: 446
<212> TYPE: PRT
<213> ORGANISM: Artificial Sequence
<220> FEATURE:
<223> OTHER INFORMATION: Amino acid sequence of polypeptide chain H3

<400> SEQUENCE: 14

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Cys Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 15
<211> LENGTH: 2940
<212> TYPE: DNA
<213> ORGANISM: Artificial Sequence
<220> FEATURE:
<223> OTHER INFORMATION: DNA sequence of polypeptide chain H2a

<400> SEQUENCE: 15

```
caagtgcagc tgcagcagtg gggcgctggc ctgctgaagc cttccgagac actgtctctg      60

acctgtgctg tttacggcgg ctccttctcc gactactact ggaactggat cagacagcct     120

cctggcaagg gcctggaatg gatcggcgag atcaaccaca gaggctctac caactccaac     180

ccatctctga agtccagagt gacactgagt ctggacacct ctaagaatca gttctccctg     240

aagctgagat ctgtgaccgc cgccgacacc gctgtgtact actgcgcctt cggctactcc     300

gactatgaat acaactggtt cgacccttgg ggccagggca ccctggtgac cgtgagctct     360

gcttccacaa aggccctag cgtgtttcct ctggcccctt gctccagatc cacttctgag     420

tccaccgctg ctctcggctg cctggtgaag gactacttcc ccgaacccgt caccgtgtcc     480
```

```
tggaacagcg gcgccttgac ctccggcgtg cacaccttcc ctgccgtgct gcagagtagc    540
ggactgtata gcctgtccag cgtcgtgacc gtgccttcct cttccctggg cacaaagaca    600
tacacctgca acgtggacca caagccctct aacaccaaag tggataagcg ggtagagtcc    660
aagtacggcc ccccttgccc tccttgtcct gctcctgagt tcctgggagg cccttctgtg    720
tttctgttcc cccccaaacc taaggatacc ctgatgatct ctcggacccc tgaggtgacc    780
tgcgtggtgg tggacgtgtc acaagaggat cctgaagtgc agtttaattg gtacgtggac    840
ggcgtggaag tgcataacgc caaaaccaaa ccacgcgaag aacagttcaa ctccacctac    900
agagtcgtca gcgtgctgac cgtgctgcac caggattggc tgaacggcaa ggagtacaag    960
tgcaaggtgt ccaacaaggg actgccttct tccatcgaga agaccatctc caaggccaag   1020
ggccagcctc gggagcctca ggtgtacacc ctccctccat gccaggaaga gatgaccaag   1080
aaccaggtgt ccctgtggtg tctggtcaag ggttctacc cctctgacat cgccgtggag   1140
tgggagtcta atggccaacc cgagaacaac tacaagacca cccctccagt gctggactct   1200
gatggatctt tcttcctgta ctcccggctg acagtggaca agagcagatg gcaggaaggc   1260
aacgtgttct cctgctccgt gatgcacgag gccctgcata accactatac ccagaagtct   1320
ctgtctctgt ctctgggatc aggtggaggc ggtagtggcg gaggcggttc aggcggaggc   1380
ggatctattt gggagctgaa gaaagacgtg tacgtggtcg agctggactg gtaccctgat   1440
gccccaggcg agatggtcgt gctgacctgc gatacaccag aggaagatgg tatcacctgg   1500
acactggatc agtcctcaga ggtgctgggc tctggtaaaa cactgaccat tcaggtgaag   1560
gagttcggtg acgctggaca gtacacttgt cataagggcg gggaggtgct gtctcactcc   1620
ctgctgctgc tgcataagaa ggaggatgga atctggtcca ctgacatcct gaaagaccag   1680
aaggagccaa agaacaaaac cttcctgcga tgcgaggcta agaactacag cggccgcttt   1740
acatgctggt ggctgacaac catcagcacc gatctgacct ttagcgtgaa gtcatccagg   1800
ggcagttcag accctcaggg agtcacatgt ggcgccgcaa ccctgtcagc agagcgagtg   1860
cggggagaca ataaggaata cgagtacagc gtcgagtgtc aggaggattc cgcatgtcca   1920
gctgcagaag aatccctgcc tatcgaagtc atggtggacg ctgtgcataa actgaagtac   1980
gagaattaca ccagcagctt tttcatccgg gacatcatca agcccgatcc acctaagaat   2040
ctgcagctga agcctctgaa aaatagccga caggtcgaag tgtcatggga atacccagac   2100
acctggtcaa caccacactc ctacttctcc ctgaccttct gtgtgcaggt ccagggaaaa   2160
agcaagcggg aaaagaaaga tcgggtgttc accgacaaga ccagtgctac agtgatttgc   2220
cggaagaatg ccagcatttc tgtcagagct caggaccggt actatagctc ttcctggagc   2280
gagtgggctt cagtgccatg ttctggaggc ggtggatctg gcggaggtgg aagcggaggc   2340
ggtggatcta gaaacctgcc cgtcgcaacc cctgatccag ggatgttccc ctgtctgcat   2400
cacagccaga atctgctgag ggctgtctcc aacatgctgc agaaggctcg acagaccctg   2460
gagttctacc catgtaccag cgaagagatc gaccacgagg atatcacaaa ggataaaacc   2520
agcacagtgg aagcatgcct gcctctggaa ctgaccaaga atgagagctg cctgaatagc   2580
agggagacct ccttcatcac caacggctca tgcctggctt caaggaagac cagcttcatg   2640
atggctctgt gtctgagctc tatctatgag gacctgaaga tgtaccaggt ggagttcaag   2700
accatgaacg ccaagctgct gatggatcca aagaggcaga tcttcctgga tcagaatatg   2760
ctggcagtga tcgatgagct gatgcaggcc ctgaatttta acagtgagac agtgcctcag   2820
```

aagagctctc tggaagagcc agacttttac aaaactaaga tcaagctgtg cattctgctg 2880
cacgctttcc gcatcagagc tgtcactatc gatagagtga tgagctatct gaatgcctca 2940

<210> SEQ ID NO 16
<211> LENGTH: 980
<212> TYPE: PRT
<213> ORGANISM: Artificial Sequence
<220> FEATURE:
<223> OTHER INFORMATION: Amino acid sequence of polypeptide chain H2a

<400> SEQUENCE: 16

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Ser Gly
        435                 440                 445

Gly Gly Gly Ser Gly Gly Gly Gly Ser Gly Gly Gly Gly Ser Ile Trp
    450                 455                 460

Glu Leu Lys Lys Asp Val Tyr Val Val Glu Leu Asp Trp Tyr Pro Asp
465                 470                 475                 480

Ala Pro Gly Glu Met Val Val Leu Thr Cys Asp Thr Pro Glu Glu Asp
                485                 490                 495

Gly Ile Thr Trp Thr Leu Asp Gln Ser Ser Glu Val Leu Gly Ser Gly
            500                 505                 510

Lys Thr Leu Thr Ile Gln Val Lys Glu Phe Gly Asp Ala Gly Gln Tyr
        515                 520                 525

Thr Cys His Lys Gly Gly Glu Val Leu Ser His Ser Leu Leu Leu Leu
    530                 535                 540

His Lys Lys Glu Asp Gly Ile Trp Ser Thr Asp Ile Leu Lys Asp Gln
545                 550                 555                 560

Lys Glu Pro Lys Asn Lys Thr Phe Leu Arg Cys Glu Ala Lys Asn Tyr
                565                 570                 575

Ser Gly Arg Phe Thr Cys Trp Trp Leu Thr Thr Ile Ser Thr Asp Leu
            580                 585                 590

Thr Phe Ser Val Lys Ser Ser Arg Gly Ser Ser Asp Pro Gln Gly Val
        595                 600                 605

Thr Cys Gly Ala Ala Thr Leu Ser Ala Glu Arg Val Arg Gly Asp Asn
    610                 615                 620

Lys Glu Tyr Glu Tyr Ser Val Glu Cys Gln Glu Asp Ser Ala Cys Pro
625                 630                 635                 640

Ala Ala Glu Glu Ser Leu Pro Ile Glu Val Met Val Asp Ala Val His
                645                 650                 655

Lys Leu Lys Tyr Glu Asn Tyr Thr Ser Ser Phe Phe Ile Arg Asp Ile
            660                 665                 670

Ile Lys Pro Asp Pro Pro Lys Asn Leu Gln Leu Lys Pro Leu Lys Asn
        675                 680                 685

Ser Arg Gln Val Glu Val Ser Trp Glu Tyr Pro Asp Thr Trp Ser Thr
    690                 695                 700

Pro His Ser Tyr Phe Ser Leu Thr Phe Cys Val Gln Val Gln Gly Lys
705                 710                 715                 720

Ser Lys Arg Glu Lys Lys Asp Arg Val Phe Thr Asp Lys Thr Ser Ala
                725                 730                 735

Thr Val Ile Cys Arg Lys Asn Ala Ser Ile Ser Val Arg Ala Gln Asp
            740                 745                 750

Arg Tyr Tyr Ser Ser Ser Trp Ser Glu Trp Ala Ser Val Pro Cys Ser
        755                 760                 765
```

```
Gly Gly Gly Gly Ser Gly Gly Gly Gly Ser Gly Gly Gly Gly Ser Arg
    770                 775                 780

Asn Leu Pro Val Ala Thr Pro Asp Pro Gly Met Phe Pro Cys Leu His
785                 790                 795                 800

His Ser Gln Asn Leu Leu Arg Ala Val Ser Asn Met Leu Gln Lys Ala
                805                 810                 815

Arg Gln Thr Leu Glu Phe Tyr Pro Cys Thr Ser Glu Glu Ile Asp His
            820                 825                 830

Glu Asp Ile Thr Lys Asp Lys Thr Ser Thr Val Glu Ala Cys Leu Pro
        835                 840                 845

Leu Glu Leu Thr Lys Asn Glu Ser Cys Leu Asn Ser Arg Glu Thr Ser
    850                 855                 860

Phe Ile Thr Asn Gly Ser Cys Leu Ala Ser Arg Lys Thr Ser Phe Met
865                 870                 875                 880

Met Ala Leu Cys Leu Ser Ser Ile Tyr Glu Asp Leu Lys Met Tyr Gln
                885                 890                 895

Val Glu Phe Lys Thr Met Asn Ala Lys Leu Leu Met Asp Pro Lys Arg
            900                 905                 910

Gln Ile Phe Leu Asp Gln Asn Met Leu Ala Val Ile Asp Glu Leu Met
        915                 920                 925

Gln Ala Leu Asn Phe Asn Ser Glu Thr Val Pro Gln Lys Ser Ser Leu
    930                 935                 940

Glu Glu Pro Asp Phe Tyr Lys Thr Lys Ile Lys Leu Cys Ile Leu Leu
945                 950                 955                 960

His Ala Phe Arg Ile Arg Ala Val Thr Ile Asp Arg Val Met Ser Tyr
                965                 970                 975

Leu Asn Ala Ser
            980
```

<210> SEQ ID NO 17
<211> LENGTH: 1785
<212> TYPE: DNA
<213> ORGANISM: Artificial Sequence
<220> FEATURE:
<223> OTHER INFORMATION: DNA sequence of polypeptide chain H3a

<400> SEQUENCE: 17

```
caagtgcagc tgcagcagtg gggcgctggc ctgctgaagc cttccgagac actgtctctg     60

acctgtgctg tttacggcgg ctccttctcc gactactact ggaactggat cagacagcct    120

cctggcaagg gcctggaatg gatcggcgag atcaaccaca gaggctctac caactccaac    180

ccatctctga agtccagagt gacactgagt ctggacacct ctaagaatca gttctccctg    240

aagctgagat ctgtgaccgc cgccgacacc gctgtgtact actgcgcctt cggctactcc    300

gactatgaat acaactggtt cgacccttgg ggccagggca ccctggtgac cgtgagctct    360

gcttccacaa aaggccctag cgtgtttcct ctggcccctt gctccagatc cacttctgag    420

tccaccgctg ctctcggctg cctggtgaag gactacttcc ccgaacccgt caccgtgtcc    480

tggaacagcg gcgccttgac ctccggcgtg cacaccttcc ctgccgtgct gcagagtagc    540

ggactgtata gcctgtccag cgtcgtgacc gtgccttcct cttccctggg cacaaagaca    600

tacacctgca acgtggacca caagccctct aacaccaaag tggataagcg ggtagagtcc    660

aagtacggcc ccccttgccc tccttgtcct gctcctgagt tcctgggagg cccttctgtg    720

tttctgttcc cccccaaacc taaggatacc ctgatgatct ctcggacccc tgaggtgacc    780

tgcgtggtgg tggacgtgtc acaagaggat cctgaagtgc agtttaattg gtacgtggac    840
```

```
ggcgtggaag tgcataacgc caaaaccaaa ccacgcgaag aacagttcaa ctccacctac    900

agagtcgtca gcgtgctgac cgtgctgcac caggattggc tgaacggcaa ggagtacaag    960

tgcaaggtgt ccaacaaggg actgccttct tccatcgaga agaccatctc caaggccaag   1020

ggccagcctc gggagcctca ggtgtgtacc ctccctccat cccaggaaga gatgaccaag   1080

aaccaggtgt ccctgtcctg tgctgtcaag ggcttctacc cctctgacat cgccgtggag   1140

tgggagtcta atggccaacc cgagaacaac tacaagacca cccctccagt gctggactct   1200

gatggatctt tcttcctggt gtcccggctg acagtggaca agagcagatg gcaggaaggc   1260

aacgtgttct cctgctccgt gatgcacgag gccctgcata accactatac ccagaagtct   1320

ctgtctctgt ctctgggatc aggtggaggc ggtagtggcg gaggcggttc aggcggaggc   1380

ggatctgcac ctacttcaag ttctacaaag aaaacacagc tacaactgga gcatttactg   1440

ctggatttac agatgatttt gaatggaatt aataattaca agaatcccaa actcaccagg   1500

atgctcacat ttaagtttta catgcccaag aaggccacag aactgaaaca tcttcagtgt   1560

ctagaagaag aactcaaacc tctggaggaa gtgctaaatt tagctcaaag caaaaacttt   1620

cacttaagac ccagggactt aatcagcaat atcaacgtaa tagttctgga actaaaggga   1680

tctgaaacaa cattcatgtg tgaatatgct gatgagacag caaccattgt agaatttctg   1740

aacagatgga ttaccttttg tcaaagcatc atctcaacac tgact                   1785
```

<210> SEQ ID NO 18
<211> LENGTH: 595
<212> TYPE: PRT
<213> ORGANISM: Artificial Sequence
<220> FEATURE:
<223> OTHER INFORMATION: Amino acid sequence of polypeptide chain H3a

<400> SEQUENCE: 18

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Cys Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Ser Gly
        435                 440                 445

Gly Gly Gly Ser Gly Gly Gly Gly Ser Gly Gly Gly Gly Ser Ala Pro
    450                 455                 460

Thr Ser Ser Ser Thr Lys Lys Thr Gln Leu Gln Leu Glu His Leu Leu
465                 470                 475                 480

Leu Asp Leu Gln Met Ile Leu Asn Gly Ile Asn Asn Tyr Lys Asn Pro
                485                 490                 495

Lys Leu Thr Arg Met Leu Thr Phe Lys Phe Tyr Met Pro Lys Lys Ala
            500                 505                 510

Thr Glu Leu Lys His Leu Gln Cys Leu Glu Glu Glu Leu Lys Pro Leu
        515                 520                 525

Glu Glu Val Leu Asn Leu Ala Gln Ser Lys Asn Phe His Leu Arg Pro
    530                 535                 540

Arg Asp Leu Ile Ser Asn Ile Asn Val Ile Val Leu Glu Leu Lys Gly
545                 550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Cys Gln Ser Ile Ile Ser
            580                 585                 590

Thr Leu Thr
        595
```

<210> SEQ ID NO 19
<211> LENGTH: 1785
<212> TYPE: DNA
<213> ORGANISM: Artificial Sequence
<220> FEATURE:
<223> OTHER INFORMATION: DNA sequence of polypeptide chain H2b

<400> SEQUENCE: 19

```
caagtgcagc tgcagcagtg gggcgctggc ctgctgaagc cttccgagac actgtctctg     60
acctgtgctg tttacggcgg ctccttctcc gactactact ggaactggat cagacagcct    120
cctggcaagg gcctggaatg gatcggcgag atcaaccaca gaggctctac caactccaac    180
ccatctctga agtccagagt gacactgagt ctggacacct ctaagaatca gttctccctg    240
aagctgagat ctgtgaccgc cgccgacacc gctgtgtact actgcgcctt cggctactcc    300
gactatgaat acaactggtt cgacccttgg ggccagggca ccctggtgac cgtgagctct    360
gcttccacaa aaggccctag cgtgtttcct ctggcccctt gctccagatc cacttctgag    420
tccaccgctg ctctcggctg cctggtgaag gactacttcc ccgaacccgt caccgtgtcc    480
tggaacagcg gcgccttgac ctccggcgtg cacaccttcc ctgccgtgct gcagagtagc    540
ggactgtata gcctgtccag cgtcgtgacc gtgccttcct cttccctggg cacaaagaca    600
tacacctgca acgtggacca caagccctct aacaccaaag tggataagcg ggtagagtcc    660
aagtacggcc ccccttgccc tccttgtcct gctcctgagt tcctgggagg cccttctgtg    720
tttctgttcc cccccaaacc taaggatacc ctgatgatct ctcggacccc tgaggtgacc    780
tgcgtggtgg tggacgtgtc acaagaggat cctgaagtgc agtttaattg gtacgtggac    840
ggcgtggaag tgcataacgc caaaaccaaa ccacgcgaag aacagttcaa ctccacctac    900
agagtcgtca gcgtgctgac cgtgctgcac caggattggc tgaacggcaa ggagtacaag    960
tgcaaggtgt ccaacaaggg actgccttct tccatcgaga agaccatctc caaggccaag   1020
ggccagcctc gggagcctca ggtgtacacc ctccctccat gccaggaaga gatgaccaag   1080
aaccaggtgt ccctgtggtg tctggtcaag ggtttctacc cctctgacat cgccgtggag   1140
tgggagtcta atggccaacc cgagaacaac tacaagacca cccctccagt gctggactct   1200
gatggatctt tcttcctgta ctcccggctg acagtggaca agagcagatg gcaggaaggc   1260
aacgtgttct cctgctccgt gatgcacgag gccctgcata accactatac ccagaagtct   1320
ctgtctctgt ctctgggatc aggtggaggc ggtagtggcg gaggcggttc aggcggaggc   1380
ggatctgcac ctacttcaag ttctacaaag aaaacacagc tacaactgga gcatttactg   1440
ctggatttac agatgatttt gaatggaatt aataattaca agaatcccaa actcaccagg   1500
atgctcacat ttaagtttta catgcccaag aaggccacag aactgaaaca tcttcagtgt   1560
ctagaagaag aactcaaacc tctggaggaa gtgctaaatt tagctcaaag caaaaacttt   1620
cacttaagac ccagggactt aatcagcaat atcaacgtaa tagttctgga actaaaggga   1680
tctgaaacaa cattcatgtg tgaatatgct gatgagacag caaccattgt agaatttctg   1740
aacagatgga ttaccttttg tcaaagcatc atctcaacac tgact                   1785
```

<210> SEQ ID NO 20
<211> LENGTH: 595
<212> TYPE: PRT
<213> ORGANISM: Artificial Sequence
<220> FEATURE:
<223> OTHER INFORMATION: Amino acid sequence of polypeptide chain H2b

<400> SEQUENCE: 20

-continued

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
```

```
        420                 425                 430

His Asn His Tyr Thr Gln Lys Ser Leu Ser Leu Ser Leu Gly Ser Gly
        435                 440                 445

Gly Gly Gly Ser Gly Gly Gly Gly Ser Gly Gly Gly Gly Ser Ala Pro
    450                 455                 460

Thr Ser Ser Ser Thr Lys Lys Thr Gln Leu Gln Leu Glu His Leu Leu
465                 470                 475                 480

Leu Asp Leu Gln Met Ile Leu Asn Gly Ile Asn Asn Tyr Lys Asn Pro
                485                 490                 495

Lys Leu Thr Arg Met Leu Thr Phe Lys Phe Tyr Met Pro Lys Lys Ala
            500                 505                 510

Thr Glu Leu Lys His Leu Gln Cys Leu Glu Glu Glu Leu Lys Pro Leu
        515                 520                 525

Glu Glu Val Leu Asn Leu Ala Gln Ser Lys Asn Phe His Leu Arg Pro
    530                 535                 540

Arg Asp Leu Ile Ser Asn Ile Asn Val Ile Val Leu Glu Leu Lys Gly
545                 550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Cys Gln Ser Ile Ile Ser
            580                 585                 590

Thr Leu Thr
        595
```

<210> SEQ ID NO 21
<211> LENGTH: 1344
<212> TYPE: DNA
<213> ORGANISM: Artificial Sequence
<220> FEATURE:
<223> OTHER INFORMATION: DNA sequence of polypeptide chain H4

<400> SEQUENCE: 21

```
gaggtgcagc tggtggaaag cggaggaggc ctggtacagc ctggcggctc tctgcggctg     60

tcttgtgccg cttctggctt taccttctcc gattcctgga tccactgggt ccgccaggcc    120

ccgggcaagg gcctggaatg ggtggcttgg atctctcctt acggcggatc tacatattac    180

gccgactctg tgaagggcag attcaccatc tctgccgata cctctaagaa caccgcctac    240

ctgcagatga acagcctgag agccgaggac accgctgtgt actactgcgc ccggagacac    300

tggcctggcg gcttcgacta ctggggccaa ggcaccctcg tcacagtgtc ctccgcctct    360

accaagggac ctagtgtgtt ccctctggcc ccctcttcca aaagcacctc cggtggcacc    420

gctgctctgg gctgcctggt gaaggactac ttccccgagc ccgtgaccgt gtcttggaac    480

tccggcgctc tgacatctgg cgtccataca tttcctgctg tgcttcagtc cagcggactg    540

tacagcctgt cctccgtggt gaccgtgccc tcctcttccc tcggcacaca gacctatatc    600

tgcaacgtga accacaagcc ttccaatacc aaggtggaca agaaagtgga acctaagtct    660

tgcgacaaga cccacacctg ccctccttgt cctgctcccg agctgctggg cggcccttcc    720

gtgtttctgt tcccacctaa gcccaaggac accctgatga tcagccggac ccctgaagtg    780

acatgcgtgg tcgtggacgt gtctcatgag gatcctgaag tgaagttcaa ctggtacgtg    840

gatggcgtgg aagtgcacaa cgccaagacc aaacctcggg aagagcagta cgcctctacc    900

tacagagtgg tgtccgtgct gacagtgctg caccaggact ggctgaacgg aaaagagtac    960

aagtgcaagg tgtccaacaa ggccctgcct gctcctatcg agaagaccat ctccaaggct   1020
```

-continued

```
aagggccagc ctagagaacc acaagtgtac accctgcctc catctagaga ggagatgacc   1080

aaaaaccagg ttagtctgac ctgtctggtc aagggcttct acccttctga catcgccgtg   1140

gagtgggagt ccaacggcca gcccgagaac aactacaaga ccaccccccc tgtgctggac   1200

tccgacggct ccttcttcct gtactccaag ctgaccgtgg ataagtccag gtggcagcag   1260

ggcaacgtgt tctcctgctc cgtgatgcac gaggccctgc acaatcacta cacccagaag   1320

tccctgtctc tgtcccctgg caag                                          1344
```

<210> SEQ ID NO 22
<211> LENGTH: 448
<212> TYPE: PRT
<213> ORGANISM: Artificial Sequence
<220> FEATURE:
<223> OTHER INFORMATION: Amino acid sequence of polypeptide chain H4

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 23
<211> LENGTH: 642
<212> TYPE: DNA
<213> ORGANISM: Artificial Sequence
<220> FEATURE:
<223> OTHER INFORMATION: DNA sequence of polypeptide chain L2

<400> SEQUENCE: 23

gacatccaga tgacccagtc tccatcttcc ctctctgctt ctgtgggcga cagagtgaca     60

atcacctgca gagcctctca ggacgtgtcc acagctgtgg cttggtacca gcagaagcct    120

ggcaaggctc ccaagctgct gatctactcc gccagcttcc tgtactccgg cgtgccctcc    180

cgcttttctg gctctggctc cggcaccgac ttcaccctga ccatctccag cctgcagcct    240

gaagattttg ctacctacta ctgccagcag tacctgtacc accctgccac cttcggccaa    300

ggcaccaagg ttgaaatcaa gcggaccgtg gccgctccca gcgtgttcat cttccctcct    360

tctgatgaac agctgaagtc cggaaccgcc tccgtggtgt gcctgctgaa caacttctac    420

cctcgggagg ccaaagtcca gtggaaggtg gacaacgccc tgcagtccgg aaatagccaa    480

gagtccgtca ccgagcagga ttctaaggac agcacctatt ctctgtcctc caccctgaca    540

ctgtccaagg ccgactacga gaagcacaag gtgtacgcct gcgaggtgac ccatcagggc    600

ctgtcttctc ctgtgaccaa atccttcaac agaggcgagt gt                       642


<210> SEQ ID NO 24
<211> LENGTH: 214
<212> TYPE: PRT
<213> ORGANISM: Artificial Sequence
<220> FEATURE:
<223> OTHER INFORMATION: Amino acid sequence of polypeptide chain L2

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 25
<211> LENGTH: 1341
<212> TYPE: DNA
<213> ORGANISM: Artificial Sequence
<220> FEATURE:
<223> OTHER INFORMATION: DNA sequence of polypeptide chain H5

<400> SEQUENCE: 25

```
gaggtgcagc tggtggaaag cggaggaggc ctggtacagc ctggcggctc tctgcggctg     60

tcttgtgccg cttctggctt taccttctcc gattcctgga tccactgggt ccgccaggcc    120

ccgggcaagg gcctggaatg ggtggcttgg atctctcctt acggcggatc tacatattac    180

gccgactctg tgaagggcag attcaccatc tctgccgata cctctaagaa caccgcctac    240

ctgcagatga acagcctgag agccgaggac accgctgtgt actactgcgc ccggagacac    300

tggcctggcg gcttcgacta ctggggccaa ggcaccctcg tcacagtgtc ctccgcctct    360

accaagggac ctagtgtgtt ccctctggcc ccctcttcca aaagcacctc cggtggcacc    420

gctgctctgg gctgcctggt gaaggactac ttccccgagc ccgtgaccgt gtcttggaac    480

tccggcgctc tgacatctgg cgtccataca tttcctgctg tgcttcagtc cagcggactg    540

tacagcctgt cctccgtggt gaccgtgccc tcctcttccc tcggcacaca gacctatatc    600

tgcaacgtga accacaagcc ttccaatacc aaggtggaca agaaagtgga acctaagtct    660

tgcgacaaga cccacacctg ccctccttgt cctgctcccg agctgctggg cggcccttcc    720

gtgtttctgt tcccacctaa gcccaaggac accctgatga tcagccggac ccctgaagtg    780

acatgcgtgg tcgtggacgt gtctcatgag gatcctgaag tgaagttcaa ctggtacgtg    840

gatggcgtgg aagtgcacaa cgccaagacc aaacctcggg aagagcagta cgcctctacc    900

tacagagtgg tgtccgtgct gacagtgctg caccaggact ggctgaacgg aaaagagtac    960

aagtgcaagg tgtccaacaa ggccctgcct gctcctatcg agaagaccat ctccaaggct   1020

aagggccagc ctagagaacc acaagtgtac accctgcctc catgtagaga ggagatgacc   1080

aaaaaccagg ttagtctgtg gtgtctggtc aagggcttct acccttctga catcgccgtg   1140
```

```
gagtgggagt ccaacggcca gcccgagaac aactacaaga ccaccccccc tgtgctggac   1200

tccgacggct ccttcttcct gtactccaag ctgaccgtgg ataagtccag gtggcagcag   1260

ggcaacgtgt tctcctgctc cgtgatgcac gaggccctgc acaatcacta cacccagaag   1320

tccctgtctc tgtcccctgg c                                             1341


<210> SEQ ID NO 26
<211> LENGTH: 447
<212> TYPE: PRT
<213> ORGANISM: Artificial Sequence
<220> FEATURE:
<223> OTHER INFORMATION: Amino acid sequence of polypeptide chain H5

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320
```

-continued

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 27
<211> LENGTH: 1341
<212> TYPE: DNA
<213> ORGANISM: Artificial Sequence
<220> FEATURE:
<223> OTHER INFORMATION: DNA sequence of polypeptide chain H6

<400> SEQUENCE: 27

gaggtgcagc tggtggaaag cggaggaggc ctggtacagc ctggcggctc tctgcggctg      60

tcttgtgccg cttctggctt taccttctcc gattcctgga tccactgggt ccgccaggcc     120

ccgggcaagg gcctggaatg ggtggcttgg atctctcctt acggcggatc tacatattac     180

gccgactctg tgaagggcag attcaccatc tctgccgata cctctaagaa caccgcctac     240

ctgcagatga acagcctgag agccgaggac accgctgtgt actactgcgc ccggagacac     300

tggcctggcg gcttcgacta ctggggccaa ggcaccctcg tcacagtgtc ctccgcctct     360

accaagggac ctagtgtgtt ccctctggcc ccctcttcca aaagcacctc cggtggcacc     420

gctgctctgg gctgcctggt gaaggactac ttccccgagc ccgtgaccgt gtcttggaac     480

tccggcgctc tgacatctgg cgtccataca tttcctgctg tgcttcagtc cagcggactg     540

tacagcctgt cctccgtggt gaccgtgccc tcctcttccc tcggcacaca gacctatatc     600

tgcaacgtga accacaagcc ttccaatacc aaggtggaca agaaagtgga acctaagtct     660

tgcgacaaga cccacacctg ccctccttgt cctgctcccg agctgctggg cggcccttcc     720

gtgtttctgt tcccacctaa gcccaaggac accctgatga tcagccggac ccctgaagtg     780

acatgcgtgg tcgtggacgt gtctcatgag gatcctgaag tgaagttcaa ctggtacgtg     840

gatggcgtgg aagtgcacaa cgccaagacc aaacctcggg aagagcagta cgcctctacc     900

tacagagtgg tgtccgtgct gacagtgctg caccaggact ggctgaacgg aaaagagtac     960

aagtgcaagg tgtccaacaa ggccctgcct gctcctatcg agaagaccat ctccaaggct    1020

aagggccagc ctagagaacc acaagtgtgc accctgcctc catctagaga ggagatgacc    1080

aaaaaccagg ttagtctgag ctgtgctgtc aagggcttct acccttctga catcgccgtg    1140

gagtgggagt ccaacggcca gcccgagaac aactacaaga ccacccccccc tgtgctggac    1200

tccgacggct ccttcttcct ggtctccaag ctgaccgtgg ataagtccag gtggcagcag    1260

ggcaacgtgt tctcctgctc cgtgatgcac gaggccctgc acaatcacta cacccagaag    1320

tccctgtctc tgtcccctgg c                                              1341
```

<210> SEQ ID NO 28
<211> LENGTH: 447
<212> TYPE: PRT
<213> ORGANISM: Artificial Sequence
<220> FEATURE:
<223> OTHER INFORMATION: Amino acid sequence of polypeptide chain H6

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365
```

```
Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 29
<211> LENGTH: 2943
<212> TYPE: DNA
<213> ORGANISM: Artificial Sequence
<220> FEATURE:
<223> OTHER INFORMATION: DNA sequence of polypeptide chain H5a

<400> SEQUENCE: 29

gaggtgcagc tggtggaaag cggaggaggc ctggtacagc ctggcggctc tctgcggctg     60

tcttgtgccg cttctggctt taccttctcc gattcctgga tccactgggt ccgccaggcc    120

ccgggcaagg gcctggaatg ggtggcttgg atctctcctt acggcggatc tacatattac    180

gccgactctg tgaagggcag attcaccatc tctgccgata cctctaagaa caccgcctac    240

ctgcagatga acagcctgag agccgaggac accgctgtgt actactgcgc ccggagacac    300

tggcctggcg gcttcgacta ctggggccaa ggcaccctcg tcacagtgtc ctccgcctct    360

accaagggac ctagtgtgtt ccctctggcc ccctcttcca aaagcacctc cggtggcacc    420

gctgctctgg gctgcctggt gaaggactac ttccccgagc ccgtgaccgt gtcttggaac    480

tccggcgctc tgacatctgg cgtccataca tttcctgctg tgcttcagtc cagcggactg    540

tacagcctgt cctccgtggt gaccgtgccc tcctcttccc tcggcacaca gacctatatc    600

tgcaacgtga accacaagcc ttccaatacc aaggtggaca agaaagtgga acctaagtct    660

tgcgacaaga cccacacctg ccctccttgt cctgctcccg agctgctggg cggcccttcc    720

gtgtttctgt tcccacctaa gcccaaggac accctgatga tcagccggac ccctgaagtg    780

acatgcgtgg tcgtggacgt gtctcatgag gatcctgaag tgaagttcaa ctggtacgtg    840

gatggcgtgg aagtgcacaa cgccaagacc aaacctcggg aagagcagta cgcctctacc    900

tacagagtgg tgtccgtgct gacagtgctg caccaggact ggctgaacgg aaaagagtac    960

aagtgcaagg tgtccaacaa ggccctgcct gctcctatcg agaagaccat ctccaaggct   1020

aagggccagc ctagagaacc acaagtgtac accctgcctc catgtagaga ggagatgacc   1080

aaaaaccagg ttagtctgtg gtgtctggtc aagggcttct acccttctga catcgccgtg   1140

gagtgggagt ccaacggcca gcccgagaac aactacaaga ccaccccccc tgtgctggac   1200

tccgacggct ccttcttcct gtactccaag ctgaccgtgg ataagtccag gtggcagcag   1260

ggcaacgtgt tctcctgctc cgtgatgcac gaggccctgc acaatcacta cacccagaag   1320

tccctgtctc tgtcccctgg ctcaggtgga ggcggtagtg gcggaggcgg ttcaggcgga   1380

ggcggatcta tttgggagct gaagaaagac gtgtacgtgg tcgagctgga ctggtaccct   1440

gatgccccag gcgagatggt cgtgctgacc tgcgatacac cagaggaaga tggtatcacc   1500

tggacactgg atcagtcctc agaggtgctg ggctctggta aaacactgac cattcaggtg   1560

aaggagttcg gtgacgctgg acagtacact tgtcataagg gcggggaggt gctgtctcac   1620
```

```
tccctgctgc tgctgcataa gaaggaggat ggaatctggt ccactgacat cctgaaagac   1680

cagaaggagc caaagaacaa aaccttcctg cgatgcgagg ctaagaacta cagcggccgc   1740

tttacatgct ggtggctgac aaccatcagc accgatctga cctttagcgt gaagtcatcc   1800

aggggcagtt cagaccctca gggagtcaca tgtggcgccg caaccctgtc agcagagcga   1860

gtgcggggag acaataagga atacgagtac agcgtcgagt gtcaggagga ttccgcatgt   1920

ccagctgcag aagaatccct gcctatcgaa gtcatggtgg acgctgtgca taaactgaag   1980

tacgagaatt acaccagcag ctttttcatc cgggacatca tcaagcccga tccacctaag   2040

aatctgcagc tgaagcctct gaaaaatagc cgacaggtcg aagtgtcatg ggaataccca   2100

gacacctggt caacaccaca ctcctacttc tccctgacct tctgtgtgca ggtccaggga   2160

aaaagcaagc gggaaaagaa agatcgggtg ttcaccgaca agaccagtgc tacagtgatt   2220

tgccggaaga atgccagcat ttctgtcaga gctcaggacc ggtactatag ctcttcctgg   2280

agcgagtggg cttcagtgcc atgttctgga ggcggtggat ctggcggagg tggaagcgga   2340

ggcggtggat ctagaaacct gcccgtcgca acccctgatc cagggatgtt cccctgtctg   2400

catcacagcc agaatctgct gagggctgtc tccaacatgc tgcagaaggc tcgacagacc   2460

ctggagttct acccatgtac cagcgaagag atcgaccacg aggatatcac aaaggataaa   2520

accagcacag tggaagcatg cctgcctctg gaactgacca agaatgagag ctgcctgaat   2580

agcagggaga cctccttcat caccaacggc tcatgcctgg cttcaaggaa gaccagcttc   2640

atgatggctc tgtgtctgag ctctatctat gaggacctga agatgtacca ggtggagttc   2700

aagaccatga acgccaagct gctgatggat ccaaagaggc agatcttcct ggatcagaat   2760

atgctggcag tgatcgatga gctgatgcag gccctgaatt ttaacagtga gacagtgcct   2820

cagaagagct ctctggaaga gccagacttt tacaaaacta agatcaagct gtgcattctg   2880

ctgcacgctt tccgcatcag agctgtcact atcgatagag tgatgagcta tctgaatgcc   2940

tca                                                                2943
```

```
<210> SEQ ID NO 30
<211> LENGTH: 981
<212> TYPE: PRT
<213> ORGANISM: Artificial Sequence
<220> FEATURE:
<223> OTHER INFORMATION: Amino acid sequence of polypeptide chain H5a

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
```

```
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ser
        435                 440                 445

Gly Gly Gly Gly Ser Gly Gly Gly Gly Ser Gly Gly Gly Gly Ser Ile
    450                 455                 460

Trp Glu Leu Lys Lys Asp Val Tyr Val Val Glu Leu Asp Trp Tyr Pro
465                 470                 475                 480

Asp Ala Pro Gly Glu Met Val Val Leu Thr Cys Asp Thr Pro Glu Glu
                485                 490                 495

Asp Gly Ile Thr Trp Thr Leu Asp Gln Ser Ser Glu Val Leu Gly Ser
            500                 505                 510

Gly Lys Thr Leu Thr Ile Gln Val Lys Glu Phe Gly Asp Ala Gly Gln
        515                 520                 525

Tyr Thr Cys His Lys Gly Gly Glu Val Leu Ser His Ser Leu Leu Leu
    530                 535                 540
```

```
Leu His Lys Lys Glu Asp Gly Ile Trp Ser Thr Asp Ile Leu Lys Asp
545                 550                 555                 560

Gln Lys Glu Pro Lys Asn Lys Thr Phe Leu Arg Cys Glu Ala Lys Asn
                565                 570                 575

Tyr Ser Gly Arg Phe Thr Cys Trp Trp Leu Thr Thr Ile Ser Thr Asp
            580                 585                 590

Leu Thr Phe Ser Val Lys Ser Ser Arg Gly Ser Ser Asp Pro Gln Gly
        595                 600                 605

Val Thr Cys Gly Ala Ala Thr Leu Ser Ala Glu Arg Val Arg Gly Asp
    610                 615                 620

Asn Lys Glu Tyr Glu Tyr Ser Val Glu Cys Gln Glu Asp Ser Ala Cys
625                 630                 635                 640

Pro Ala Ala Glu Glu Ser Leu Pro Ile Glu Val Met Val Asp Ala Val
                645                 650                 655

His Lys Leu Lys Tyr Glu Asn Tyr Thr Ser Ser Phe Phe Ile Arg Asp
            660                 665                 670

Ile Ile Lys Pro Asp Pro Pro Lys Asn Leu Gln Leu Lys Pro Leu Lys
        675                 680                 685

Asn Ser Arg Gln Val Glu Val Ser Trp Glu Tyr Pro Asp Thr Trp Ser
    690                 695                 700

Thr Pro His Ser Tyr Phe Ser Leu Thr Phe Cys Val Gln Val Gln Gly
705                 710                 715                 720

Lys Ser Lys Arg Glu Lys Lys Asp Arg Val Phe Thr Asp Lys Thr Ser
                725                 730                 735

Ala Thr Val Ile Cys Arg Lys Asn Ala Ser Ile Ser Val Arg Ala Gln
            740                 745                 750

Asp Arg Tyr Tyr Ser Ser Ser Trp Ser Glu Trp Ala Ser Val Pro Cys
        755                 760                 765

Ser Gly Gly Gly Gly Ser Gly Gly Gly Gly Ser Gly Gly Gly Gly Ser
    770                 775                 780

Arg Asn Leu Pro Val Ala Thr Pro Asp Pro Gly Met Phe Pro Cys Leu
785                 790                 795                 800

His His Ser Gln Asn Leu Leu Arg Ala Val Ser Asn Met Leu Gln Lys
                805                 810                 815

Ala Arg Gln Thr Leu Glu Phe Tyr Pro Cys Thr Ser Glu Glu Ile Asp
            820                 825                 830

His Glu Asp Ile Thr Lys Asp Lys Thr Ser Thr Val Glu Ala Cys Leu
        835                 840                 845

Pro Leu Glu Leu Thr Lys Asn Glu Ser Cys Leu Asn Ser Arg Glu Thr
    850                 855                 860

Ser Phe Ile Thr Asn Gly Ser Cys Leu Ala Ser Arg Lys Thr Ser Phe
865                 870                 875                 880

Met Met Ala Leu Cys Leu Ser Ser Ile Tyr Glu Asp Leu Lys Met Tyr
                885                 890                 895

Gln Val Glu Phe Lys Thr Met Asn Ala Lys Leu Leu Met Asp Pro Lys
            900                 905                 910

Arg Gln Ile Phe Leu Asp Gln Asn Met Leu Ala Val Ile Asp Glu Leu
        915                 920                 925

Met Gln Ala Leu Asn Phe Asn Ser Glu Thr Val Pro Gln Lys Ser Ser
    930                 935                 940

Leu Glu Glu Pro Asp Phe Tyr Lys Thr Lys Ile Lys Leu Cys Ile Leu
945                 950                 955                 960
```

```
Leu His Ala Phe Arg Ile Arg Ala Val Thr Ile Asp Arg Val Met Ser
            965                 970                 975

Tyr Leu Asn Ala Ser
        980


<210> SEQ ID NO 31
<211> LENGTH: 1788
<212> TYPE: DNA
<213> ORGANISM: Artificial Sequence
<220> FEATURE:
<223> OTHER INFORMATION: DNA sequence of polypeptide chain H6a

<400> SEQUENCE: 31

gaggtgcagc tggtggaaag cggaggaggc ctggtacagc ctggcggctc tctgcggctg      60

tcttgtgccg cttctggctt taccttctcc gattcctgga tccactgggt ccgccaggcc     120

ccgggcaagg gcctggaatg ggtggcttgg atctctcctt acggcggatc tacatattac     180

gccgactctg tgaagggcag attcaccatc tctgccgata cctctaagaa caccgcctac     240

ctgcagatga acagcctgag agccgaggac accgctgtgt actactgcgc ccggagacac     300

tggcctggcg gcttcgacta ctggggccaa ggcaccctcg tcacagtgtc ctccgcctct     360

accaagggac ctagtgtgtt ccctctggcc ccctcttcca aaagcacctc cggtggcacc     420

gctgctctgg gctgcctggt gaaggactac ttccccgagc ccgtgaccgt gtcttggaac     480

tccggcgctc tgacatctgg cgtccataca tttcctgctg tgcttcagtc cagcggactg     540

tacagcctgt cctccgtggt gaccgtgccc tcctcttccc tcggcacaca gacctatatc     600

tgcaacgtga accacaagcc ttccaatacc aaggtggaca agaaagtgga acctaagtct     660

tgcgacaaga cccacacctg ccctccttgt cctgctcccg agctgctggg cggcccttcc     720

gtgtttctgt tcccacctaa gcccaaggac accctgatga tcagccggac ccctgaagtg     780

acatgcgtgg tcgtggacgt gtctcatgag gatcctgaag tgaagttcaa ctggtacgtg     840

gatggcgtgg aagtgcacaa cgccaagacc aaacctcggg aagagcagta cgcctctacc     900

tacagagtgg tgtccgtgct gacagtgctg caccaggact ggctgaacgg aaaagagtac     960

aagtgcaagg tgtccaacaa ggccctgcct gctcctatcg agaagaccat ctccaaggct    1020

aagggccagc ctagagaacc acaagtgtgc accctgcctc catctagaga ggagatgacc    1080

aaaaaccagg ttagtctgag ctgtgctgtc aagggcttct acccttctga catcgccgtg    1140

gagtgggagt ccaacggcca gcccgagaac aactacaaga ccaccccccc tgtgctggac    1200

tccgacggct ccttcttcct ggtctccaag ctgaccgtgg ataagtccag gtggcagcag    1260

ggcaacgtgt tctcctgctc cgtgatgcac gaggccctgc acaatcacta cacccagaag    1320

tccctgtctc tgtcccctgg ctcaggtgga ggcggtagtg gcggaggcgg ttcaggcgga    1380

ggcggatctg cacctacttc aagttctaca aagaaaacac agctacaact ggagcattta    1440

ctgctggatt tacagatgat tttgaatgga attaataatt acaagaatcc caaactcacc    1500

aggatgctca catttaagtt ttacatgccc aagaaggcca cagaactgaa acatcttcag    1560

tgtctagaag aagaactcaa acctctggag gaagtgctaa atttagctca aagcaaaaac    1620

tttcacttaa gacccaggga cttaatcagc aatatcaacg taatagttct ggaactaaag    1680

ggatctgaaa caacattcat gtgtgaatat gctgatgaga cagcaaccat tgtagaattt    1740

ctgaacagat ggattacctt ttgtcaaagc atcatctcaa cactgact                 1788


<210> SEQ ID NO 32
<211> LENGTH: 596
```

```
<212> TYPE: PRT
<213> ORGANISM: Artificial Sequence
<220> FEATURE:
<223> OTHER INFORMATION: Amino acid sequence of polypeptide chain H6a

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ser
        435                 440                 445

Gly Gly Gly Gly Ser Gly Gly Gly Gly Ser Gly Gly Gly Gly Ser Ala
    450                 455                 460

Pro Thr Ser Ser Ser Thr Lys Lys Thr Gln Leu Gln Leu Glu His Leu
465                 470                 475                 480

Leu Leu Asp Leu Gln Met Ile Leu Asn Gly Ile Asn Asn Tyr Lys Asn
                485                 490                 495

Pro Lys Leu Thr Arg Met Leu Thr Phe Lys Phe Tyr Met Pro Lys Lys
            500                 505                 510

Ala Thr Glu Leu Lys His Leu Gln Cys Leu Glu Glu Glu Leu Lys Pro
        515                 520                 525

Leu Glu Glu Val Leu Asn Leu Ala Gln Ser Lys Asn Phe His Leu Arg
    530                 535                 540

Pro Arg Asp Leu Ile Ser Asn Ile Asn Val Ile Val Leu Glu Leu Lys
545                 550                 555                 560

Gly Ser Glu Thr Thr Phe Met Cys Glu Tyr Ala Asp Glu Thr Ala Thr
                565                 570                 575

Ile Val Glu Phe Leu Asn Arg Trp Ile Thr Phe Cys Gln Ser Ile Ile
            580                 585                 590

Ser Thr Leu Thr
        595
```

<210> SEQ ID NO 33
<211> LENGTH: 1788
<212> TYPE: DNA
<213> ORGANISM: Artificial Sequence
<220> FEATURE:
<223> OTHER INFORMATION: DNA sequence of polypeptide chain H5b

<400> SEQUENCE: 33

```
gaggtgcagc tggtggaaag cggaggaggc ctggtacagc ctggcggctc tctgcggctg      60

tcttgtgccg cttctggctt taccttctcc gattcctgga tccactgggt ccgccaggcc     120

ccgggcaagg gcctggaatg ggtggcttgg atctctcctt acggcggatc tacatattac     180

gccgactctg tgaagggcag attcaccatc tctgccgata cctctaagaa caccgcctac     240

ctgcagatga acagcctgag agccgaggac accgctgtgt actactgcgc ccggagacac     300

tggcctggcg gcttcgacta ctggggccaa ggcaccctcg tcacagtgtc ctccgcctct     360

accaagggac ctagtgtgtt ccctctggcc ccctcttcca aaagcacctc cggtggcacc     420

gctgctctgg gctgcctggt gaaggactac ttccccgagc ccgtgaccgt gtcttggaac     480

tccggcgctc tgacatctgg cgtccataca tttcctgctg tgcttcagtc cagcggactg     540

tacagcctgt cctccgtggt gaccgtgccc tcctcttccc tcggcacaca gacctatatc     600

tgcaacgtga accacaagcc ttccaatacc aaggtggaca agaaagtgga acctaagtct     660

tgcgacaaga cccacacctg ccctccttgt cctgctcccg agctgctggg cggcccttcc     720

gtgtttctgt tcccacctaa gcccaaggac accctgatga tcagccggac ccctgaagtg     780

acatgcgtgg tcgtggacgt gtctcatgag gatcctgaag tgaagttcaa ctggtacgtg     840
```

```
gatggcgtgg aagtgcacaa cgccaagacc aaacctcggg aagagcagta cgcctctacc    900

tacagagtgg tgtccgtgct gacagtgctg caccaggact ggctgaacgg aaaagagtac    960

aagtgcaagg tgtccaacaa ggccctgcct gctcctatcg agaagaccat ctccaaggct   1020

aagggccagc ctagagaacc acaagtgtac accctgcctc catgtagaga ggagatgacc   1080

aaaaaccagg ttagtctgtg gtgtctggtc aagggcttct acccttctga catcgccgtg   1140

gagtgggagt ccaacggcca gcccgagaac aactacaaga ccaccccccc tgtgctggac   1200

tccgacggct ccttcttcct gtactccaag ctgaccgtgg ataagtccag gtggcagcag   1260

ggcaacgtgt tctcctgctc cgtgatgcac gaggccctgc acaatcacta cacccagaag   1320

tccctgtctc tgtcccctgg ctcaggtgga ggcggtagtg gcggaggcgg ttcaggcgga   1380

ggcggatctg cacctacttc aagttctaca aagaaaacac agctacaact ggagcattta   1440

ctgctggatt tacagatgat tttgaatgga attaataatt acaagaatcc caaactcacc   1500

aggatgctca catttaagtt ttacatgccc aagaaggcca cagaactgaa acatcttcag   1560

tgtctagaag aagaactcaa acctctggag gaagtgctaa atttagctca aagcaaaaac   1620

tttcacttaa gacccaggga cttaatcagc aatatcaacg taatagttct ggaactaaag   1680

ggatctgaaa caacattcat gtgtgaatat gctgatgaga cagcaaccat tgtagaattt   1740

ctgaacagat ggattacctt ttgtcaaagc atcatctcaa cactgact                1788
```

<210> SEQ ID NO 34
<211> LENGTH: 596
<212> TYPE: PRT
<213> ORGANISM: Artificial Sequence
<220> FEATURE:
<223> OTHER INFORMATION: Amino acid sequence of polypeptide chain H5b

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ser
        435                 440                 445

Gly Gly Gly Gly Ser Gly Gly Gly Gly Ser Gly Gly Gly Gly Ser Ala
    450                 455                 460

Pro Thr Ser Ser Ser Thr Lys Lys Thr Gln Leu Gln Leu Glu His Leu
465                 470                 475                 480

Leu Leu Asp Leu Gln Met Ile Leu Asn Gly Ile Asn Asn Tyr Lys Asn
                485                 490                 495

Pro Lys Leu Thr Arg Met Leu Thr Phe Lys Phe Tyr Met Pro Lys Lys
            500                 505                 510

Ala Thr Glu Leu Lys His Leu Gln Cys Leu Glu Glu Glu Leu Lys Pro
        515                 520                 525

Leu Glu Glu Val Leu Asn Leu Ala Gln Ser Lys Asn Phe His Leu Arg
    530                 535                 540

Pro Arg Asp Leu Ile Ser Asn Ile Asn Val Ile Val Leu Glu Leu Lys
545                 550                 555                 560

Gly Ser Glu Thr Thr Phe Met Cys Glu Tyr Ala Asp Glu Thr Ala Thr
                565                 570                 575

Ile Val Glu Phe Leu Asn Arg Trp Ile Thr Phe Cys Gln Ser Ile Ile
            580                 585                 590

Ser Thr Leu Thr
        595
```

<210> SEQ ID NO 35
<211> LENGTH: 1368
<212> TYPE: DNA
<213> ORGANISM: Artificial Sequence
<220> FEATURE:
<223> OTHER INFORMATION: DNA sequence of polypeptide chain H7

<400> SEQUENCE: 35
gaagtgcagc tgcagcagtc cggccccgga ctggtcaaac cctcccagac cctgtctctt 60
acctgcgcca tctccggcga ctctgtgtcc agcaactctg ccgcttggaa ttggatccgg 120
cagtctccta gtagaggcct ggaatggctg ggcaagacat actaccggtt caagtggtat 180
tccgattacg ccgtgtccgt gaagggcaga atcaccatca accctgatac ctctaagaat 240
caattctccc tgcagctgaa ctccgtgacc cctgaggaca ccgctgtgtt ttactgcacc 300
agagagagca ccacctacga cctgctggct ggcccctttcg actactgggg ccagggaaca 360
ctcgtcaccg tgtcttccgc ctctacaaag ggcccatccg tttttcctct ggccccgtcc 420
tctaagtcta cctctggcgg caccgccgct ctgggctgcc tggtgaagga ctacttcccc 480
gagcctgtga ccgtgtcctg gaacagcggc gctctgacct ccggcgtgca taccttccct 540
gctgttctgc aatcttctgg cctgtactct ctgtcctctg tggtgaccgt gccttccagc 600
tctctgggca cccagaccta catctgcaac gtgaaccata agccttctaa cactaaggtg 660
gacaagaaag tggaacccaa gtcctgcgac aaaacccaca cctgtcctcc ttgtcctgcc 720
cctgagctgc tgggcggacc tagcgtgttc ctgttcccac ctaagcctaa ggataccctg 780
atgatctccc ggacccctga agtgacctgc gtggtcgtgg acgtgtctca cgaagatcct 840
gaagtcaagt tcaactggta cgtggatggc gtcgaggtgc acaacgccaa gaccaagccc 900
cgggaagagc agtacaactc cacatataga gtggtgagtg tgctgacagt actgcaccag 960
gactggctga acggcaaaga gtacaagtgc aaggtgtcca acaaggctct gcctgctcct 1020
atcgagaaga caatctccaa ggccaaggga cagcctagag aacctcaagt gtacaccctc 1080
ccaccttctc gcgaggagat gaccaagaac caggtgagcc tgacctgtct ggtgaaaggc 1140
ttctacccct ccgacatcgc cgtggagtgg gagtccaatg gccagccaga gaacaactac 1200
aagaccacac ctcccgtgct ggactccgac ggctccttct tcctgtactc caagctgacc 1260
gtggacaagt ctagatggca gcagggcaac gtgtttagct gctccgtgat gcacgaggcc 1320
ctgcacaacc actacaccca gaagtctctg tccctgagcc ctggaaaa 1368

<210> SEQ ID NO 36
<211> LENGTH: 456
<212> TYPE: PRT
<213> ORGANISM: Artificial Sequence
<220> FEATURE:
<223> OTHER INFORMATION: Amino acid sequence of polypeptide chain H7

<400> SEQUENCE: 36

Glu Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Lys Thr Tyr Tyr Arg Phe Lys Trp Tyr Ser Asp Tyr Ala
50 55 60

Val Ser Val Lys Gly Arg Ile Thr Ile Asn Pro Asp Thr Ser Lys Asn
65 70 75 80

```
Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 37
<211> LENGTH: 660
<212> TYPE: DNA
<213> ORGANISM: Artificial Sequence
<220> FEATURE:

<223> OTHER INFORMATION: DNA sequence of polypeptide chain L3

<400> SEQUENCE: 37

```
gatatcgtga tgacccagtc ccccgattct ctggccgtgt ccctgggcga gcgggctaca     60
atcaactgca agtcctctca gaccgtgctg tactcttcca acaacaagaa gtacctggct    120
tggtaccagc agaagcctgg ccagcctcct aatctgctga tctactgggc ctctacaagg    180
gagtccggcg tccccgatag atttagcgga tccggctctg gaaccgactt caccctgacc    240
atctccagcc tgcaagccga ggacgtggct gtgtactact gccagcagta ctattctact    300
ccttttacct tcggccccgg caccaaagtt gagatcaagc ggaccgtggc cgctccttcc    360
gtgttcatct tccctccatc cgacgaacag ctgaagtccg gcaccgctag cgtggtgtgc    420
ctgctgaaca acttctaccc tagagaagcc aaagtgcagt ggaaggtgga caacgccctg    480
cagtctggca actcccaaga gtctgtcacc gagcaggact ctaaggactc cacctactcc    540
ctcagctcca cactgaccct gtccaaggcc gactacgaga agcacaaggt gtacgcctgc    600
gaagtgaccc accagggcct gtcttctcct gtgaccaagt ccttcaacag aggcgaatgt    660
```

<210> SEQ ID NO 38
<211> LENGTH: 220
<212> TYPE: PRT
<213> ORGANISM: Artificial Sequence
<220> FEATURE:
<223> OTHER INFORMATION: Amino acid sequence of polypeptide chain L3

<400> SEQUENCE: 38

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 39
<211> LENGTH: 1365
<212> TYPE: DNA
<213> ORGANISM: Artificial Sequence
<220> FEATURE:
<223> OTHER INFORMATION: DNA sequence of polypeptide chain H8

<400> SEQUENCE: 39

```
gaagtgcagc tgcagcagtc cggccccgga ctggtcaaac cctcccagac cctgtctctt     60
acctgcgcca tctccggcga ctctgtgtcc agcaactctg ccgcttggaa ttggatccgg    120
cagtctccta gtagaggcct ggaatggctg ggcaagacat actaccggtt caagtggtat    180
tccgattacg ccgtgtccgt gaagggcaga atcaccatca accctgatac ctctaagaat    240
caattctccc tgcagctgaa ctccgtgacc cctgaggaca ccgctgtgtt ttactgcacc    300
agagagagca ccacctacga cctgctggct ggccctttcg actactgggg ccagggaaca    360
ctcgtcaccg tgtcttccgc ctctacaaag ggcccatccg tttttcctct ggccccgtcc    420
tctaagtcta cctctggcgg caccgccgct ctgggctgcc tggtgaagga ctacttcccc    480
gagcctgtga ccgtgtcctg gaacagcggc gctctgacct ccggcgtgca taccttccct    540
gctgttctgc aatcttctgg cctgtactct ctgtcctctg tggtgaccgt gccttccagc    600
tctctgggca cccagaccta catctgcaac gtgaaccata agccttctaa cactaaggtg    660
gacaagaaag tggaacccaa gtcctgcgac aaaacccaca cctgtcctcc ttgtcctgcc    720
cctgagctgc tgggcggacc tagcgtgttc ctgttcccac ctaagcctaa ggataccctg    780
atgatctccc ggacccctga agtgacctgc gtggtcgtgg acgtgtctca cgaagatcct    840
gaagtcaagt tcaactggta cgtggatggc gtcgaggtgc acaacgccaa gaccaagccc    900
cgggaagagc agtacaactc cacatataga gtggtgagtg tgctgacagt actgcaccag    960
gactggctga acggcaaaga gtacaagtgc aaggtgtcca acaaggctct gcctgctcct   1020
atcgagaaga caatctccaa ggccaaggga cagcctagag aacctcaagt gtacaccctc   1080
ccaccttgtc gcgaggagat gaccaagaac caggtgagcc tgtggtgtct ggtgaaaggc   1140
ttctacccct ccgacatcgc cgtggagtgg gagtccaatg gccagccaga gaacaactac   1200
aagaccacac ctcccgtgct ggactccgac ggctccttct tcctgtactc caagctgacc   1260
gtggacaagt ctagatggca gcagggcaac gtgtttagct gctccgtgat gcacgaggcc   1320
ctgcacaacc actacaccca gaagtctctg tccctgagcc ctgga                    1365
```

<210> SEQ ID NO 40
<211> LENGTH: 455
<212> TYPE: PRT
<213> ORGANISM: Artificial Sequence
<220> FEATURE:
<223> OTHER INFORMATION: Amino acid sequence of polypeptide chain H8

<400> SEQUENCE: 40

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Glu Glu Met Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455
```

<210> SEQ ID NO 41
<211> LENGTH: 1365
<212> TYPE: DNA
<213> ORGANISM: Artificial Sequence
<220> FEATURE:

<223> OTHER INFORMATION: DNA sequence of polypeptide chain H9

<400> SEQUENCE: 41

```
gaagtgcagc tgcagcagtc cggccccgga ctggtcaaac cctcccagac cctgtctctt     60
acctgcgcca tctccggcga ctctgtgtcc agcaactctg ccgcttggaa ttggatccgg    120
cagtctccta gtagaggcct ggaatggctg ggcaagacat actaccggtt caagtggtat    180
tccgattacg ccgtgtccgt gaagggcaga atcaccatca accctgatac ctctaagaat    240
caattctccc tgcagctgaa ctccgtgacc cctgaggaca ccgctgtgtt ttactgcacc    300
agagagagca ccacctacga cctgctggct ggccctttcg actactgggg ccagggaaca    360
ctcgtcaccg tgtcttccgc ctctacaaag ggcccatccg tttttcctct ggccccgtcc    420
tctaagtcta cctctggcgg caccgccgct ctgggctgcc tggtgaagga ctacttcccc    480
gagcctgtga ccgtgtcctg gaacagcggc gctctgacct ccggcgtgca taccttccct    540
gctgttctgc aatcttctgg cctgtactct ctgtcctctg tggtgaccgt gccttccagc    600
tctctgggca cccagaccta catctgcaac gtgaaccata agccttctaa cactaaggtg    660
gacaagaaag tggaacccaa gtcctgcgac aaaacccaca cctgtcctcc ttgtcctgcc    720
cctgagctgc tgggcggacc tagcgtgttc ctgttcccac ctaagcctaa ggataccctg    780
atgatctccc ggacccctga agtgacctgc gtggtcgtgg acgtgtctca cgaagatcct    840
gaagtcaagt tcaactggta cgtggatggc gtcgaggtgc acaacgccaa gaccaagccc    900
cgggaagagc agtacaactc cacatataga gtggtgagtg tgctgacagt actgcaccag    960
gactggctga acggcaaaga gtacaagtgc aaggtgtcca acaaggctct gcctgctcct   1020
atcgagaaga caatctccaa ggccaaggga cagcctagag aacctcaagt gtgcaccctc   1080
ccaccttctc gcgaggagat gaccaagaac caggtgagcc tgtcctgtgc tgtgaaaggc   1140
ttctacccct ccgacatcgc cgtggagtgg gagtccaatg gccagccaga gaacaactac   1200
aagaccacac ctcccgtgct ggactccgac ggctccttct tcctggtgtc caagctgacc   1260
gtggacaagt ctagatggca gcagggcaac gtgtttagct gctccgtgat gcacgaggcc   1320
ctgcacaacc actacaccca gaagtctctg tccctgagcc ctgga                    1365
```

<210> SEQ ID NO 42
<211> LENGTH: 455
<212> TYPE: PRT
<213> ORGANISM: Artificial Sequence
<220> FEATURE:
<223> OTHER INFORMATION: Amino acid sequence of polypeptide chain H9

<400> SEQUENCE: 42

```
Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
```

```
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Cys Thr Leu Pro Pro Ser Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 43
<211> LENGTH: 2967
<212> TYPE: DNA
<213> ORGANISM: Artificial Sequence
<220> FEATURE:
<223> OTHER INFORMATION: DNA sequence of polypeptide chain H8a

<400> SEQUENCE: 43

gaagtgcagc tgcagcagtc cggccccgga ctggtcaaac cctcccagac cctgtctctt     60
```

```
acctgcgcca tctccggcga ctctgtgtcc agcaactctg ccgcttggaa ttggatccgg    120
cagtctccta gtagaggcct ggaatggctg ggcaagacat actaccggtt caagtggtat    180
tccgattacg ccgtgtccgt gaagggcaga atcaccatca accctgatac ctctaagaat    240
caattctccc tgcagctgaa ctccgtgacc cctgaggaca ccgctgtgtt ttactgcacc    300
agagagagca ccacctacga cctgctggct ggccctttcg actactgggg ccagggaaca    360
ctcgtcaccg tgtcttccgc ctctacaaag ggcccatccg tttttcctct ggccccgtcc    420
tctaagtcta cctctggcgg caccgccgct ctgggctgcc tggtgaagga ctacttcccc    480
gagcctgtga ccgtgtcctg gaacagcggc gctctgacct ccggcgtgca taccttccct    540
gctgttctgc aatcttctgg cctgtactct ctgtcctctg tggtgaccgt gccttccagc    600
tctctgggca cccagaccta catctgcaac gtgaaccata agccttctaa cactaaggtg    660
gacaagaaag tggaacccaa gtcctgcgac aaaacccaca cctgtcctcc ttgtcctgcc    720
cctgagctgc tgggcggacc tagcgtgttc ctgttcccac ctaagcctaa ggataccctg    780
atgatctccc ggacccctga agtgacctgc gtggtcgtgg acgtgtctca cgaagatcct    840
gaagtcaagt tcaactggta cgtggatggc gtcgaggtgc acaacgccaa gaccaagccc    900
cgggaagagc agtacaactc cacatataga gtggtgagtg tgctgacagt actgcaccag    960
gactggctga acggcaaaga gtacaagtgc aaggtgtcca acaaggctct gcctgctcct   1020
atcgagaaga caatctccaa ggccaaggga cagcctagag aacctcaagt gtacaccctc   1080
ccaccttgtc gcgaggagat gaccaagaac caggtgagcc tgtggtgtct ggtgaaaggc   1140
ttctacccct ccgacatcgc cgtggagtgg gagtccaatg gccagccaga gaacaactac   1200
aagaccacac ctcccgtgct ggactccgac ggctccttct tcctgtactc caagctgacc   1260
gtggacaagt ctagatggca gcagggcaac gtgtttagct gctccgtgat gcacgaggcc   1320
ctgcacaacc actacaccca gaagtctctg tccctgagcc ctggatcagg tggaggcggt   1380
agtggcggag gcggttcagg cggaggcgga tctatttggg agctgaagaa agacgtgtac   1440
gtggtcgagc tggactggta ccctgatgcc ccaggcgaga tggtcgtgct gacctgcgat   1500
acaccagagg aagatggtat cacctggaca ctggatcagt cctcagaggt gctgggctct   1560
ggtaaaacac tgaccattca ggtgaaggag ttcggtgacg ctggacagta cacttgtcat   1620
aagggcgggg aggtgctgtc tcactccctg ctgctgctgc ataagaagga ggatggaatc   1680
tggtccactg acatcctgaa agaccagaag gagccaaaga acaaaacctt cctgcgatgc   1740
gaggctaaga actacagcgg ccgctttaca tgctggtggc tgacaaccat cagcaccgat   1800
ctgaccttta gcgtgaagtc atccaggggc agttcagacc ctcagggagt cacatgtggc   1860
gccgcaaccc tgtcagcaga gcgagtgcgg ggagacaata aggaatacga gtacagcgtc   1920
gagtgtcagg aggattccgc atgtccagct gcagaagaat ccctgcctat cgaagtcatg   1980
gtggacgctg tgcataaact gaagtacgag aattacacca gcagcttttt catccgggac   2040
atcatcaagc ccgatccacc taagaatctg cagctgaagc ctctgaaaaa tagccgacag   2100
gtcgaagtgt catgggaata cccagacacc tggtcaacac cacactccta cttctccctg   2160
accttctgtg tgcaggtcca gggaaaaagc aagcgggaaa agaaagatcg ggtgttcacc   2220
gacaagacca gtgctacagt gatttgccgg aagaatgcca gcatttctgt cagagctcag   2280
gaccggtact atagctcttc ctggagcgag tgggcttcag tgccatgttc tggaggcggt   2340
ggatctggcg gaggtggaag cggaggcggt ggatctagaa acctgcccgt cgcaacccct   2400
```

```
gatccaggga tgttcccctg tctgcatcac agccagaatc tgctgagggc tgtctccaac   2460

atgctgcaga aggctcgaca gaccctggag ttctacccat gtaccagcga agagatcgac   2520

cacgaggata tcacaaagga taaaaccagc acagtggaag catgcctgcc tctggaactg   2580

accaagaatg agagctgcct gaatagcagg gagacctcct tcatcaccaa cggctcatgc   2640

ctggcttcaa ggaagaccag cttcatgatg gctctgtgtc tgagctctat ctatgaggac   2700

ctgaagatgt accaggtgga gttcaagacc atgaacgcca agctgctgat ggatccaaag   2760

aggcagatct tcctggatca gaatatgctg gcagtgatcg atgagctgat gcaggccctg   2820

aattttaaca gtgagacagt gcctcagaag agctctctgg aagagccaga cttttacaaa   2880

actaagatca agctgtgcat tctgctgcac gctttccgca tcagagctgt cactatcgat   2940

agagtgatga gctatctgaa tgcctca                                        2967
```

```
<210> SEQ ID NO 44
<211> LENGTH: 989
<212> TYPE: PRT
<213> ORGANISM: Artificial Sequence
<220> FEATURE:
<223> OTHER INFORMATION: Amino acid sequence of polypeptide chain H8a

<400> SEQUENCE: 44

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
```

```
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Glu Glu Met Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Ser Gly Gly Gly Gly Ser Gly Gly Gly
    450                 455                 460

Gly Ser Gly Gly Gly Gly Ser Ile Trp Glu Leu Lys Lys Asp Val Tyr
465                 470                 475                 480

Val Val Glu Leu Asp Trp Tyr Pro Asp Ala Pro Gly Glu Met Val Val
                485                 490                 495

Leu Thr Cys Asp Thr Pro Glu Glu Asp Gly Ile Thr Trp Thr Leu Asp
            500                 505                 510

Gln Ser Ser Glu Val Leu Gly Ser Gly Lys Thr Leu Thr Ile Gln Val
        515                 520                 525

Lys Glu Phe Gly Asp Ala Gly Gln Tyr Thr Cys His Lys Gly Gly Glu
    530                 535                 540

Val Leu Ser His Ser Leu Leu Leu Leu His Lys Lys Glu Asp Gly Ile
545                 550                 555                 560

Trp Ser Thr Asp Ile Leu Lys Asp Gln Lys Glu Pro Lys Asn Lys Thr
                565                 570                 575

Phe Leu Arg Cys Glu Ala Lys Asn Tyr Ser Gly Arg Phe Thr Cys Trp
            580                 585                 590

Trp Leu Thr Thr Ile Ser Thr Asp Leu Thr Phe Ser Val Lys Ser Ser
        595                 600                 605

Arg Gly Ser Ser Asp Pro Gln Gly Val Thr Cys Gly Ala Ala Thr Leu
    610                 615                 620

Ser Ala Glu Arg Val Arg Gly Asp Asn Lys Glu Tyr Glu Tyr Ser Val
625                 630                 635                 640

Glu Cys Gln Glu Asp Ser Ala Cys Pro Ala Ala Glu Glu Ser Leu Pro
                645                 650                 655

Ile Glu Val Met Val Asp Ala Val His Lys Leu Lys Tyr Glu Asn Tyr
            660                 665                 670

Thr Ser Ser Phe Phe Ile Arg Asp Ile Ile Lys Pro Asp Pro Pro Lys
        675                 680                 685
```

```
Asn Leu Gln Leu Lys Pro Leu Lys Asn Ser Arg Gln Val Glu Val Ser
    690                 695                 700

Trp Glu Tyr Pro Asp Thr Trp Ser Thr Pro His Ser Tyr Phe Ser Leu
705                 710                 715                 720

Thr Phe Cys Val Gln Val Gln Gly Lys Ser Lys Arg Glu Lys Lys Asp
                725                 730                 735

Arg Val Phe Thr Asp Lys Thr Ser Ala Thr Val Ile Cys Arg Lys Asn
            740                 745                 750

Ala Ser Ile Ser Val Arg Ala Gln Asp Arg Tyr Tyr Ser Ser Ser Trp
        755                 760                 765

Ser Glu Trp Ala Ser Val Pro Cys Ser Gly Gly Gly Gly Ser Gly Gly
    770                 775                 780

Gly Gly Ser Gly Gly Gly Gly Ser Arg Asn Leu Pro Val Ala Thr Pro
785                 790                 795                 800

Asp Pro Gly Met Phe Pro Cys Leu His His Ser Gln Asn Leu Leu Arg
                805                 810                 815

Ala Val Ser Asn Met Leu Gln Lys Ala Arg Gln Thr Leu Glu Phe Tyr
            820                 825                 830

Pro Cys Thr Ser Glu Glu Ile Asp His Glu Asp Ile Thr Lys Asp Lys
        835                 840                 845

Thr Ser Thr Val Glu Ala Cys Leu Pro Leu Glu Leu Thr Lys Asn Glu
    850                 855                 860

Ser Cys Leu Asn Ser Arg Glu Thr Ser Phe Ile Thr Asn Gly Ser Cys
865                 870                 875                 880

Leu Ala Ser Arg Lys Thr Ser Phe Met Met Ala Leu Cys Leu Ser Ser
                885                 890                 895

Ile Tyr Glu Asp Leu Lys Met Tyr Gln Val Glu Phe Lys Thr Met Asn
            900                 905                 910

Ala Lys Leu Leu Met Asp Pro Lys Arg Gln Ile Phe Leu Asp Gln Asn
        915                 920                 925

Met Leu Ala Val Ile Asp Glu Leu Met Gln Ala Leu Asn Phe Asn Ser
    930                 935                 940

Glu Thr Val Pro Gln Lys Ser Ser Leu Glu Glu Pro Asp Phe Tyr Lys
945                 950                 955                 960

Thr Lys Ile Lys Leu Cys Ile Leu Leu His Ala Phe Arg Ile Arg Ala
                965                 970                 975

Val Thr Ile Asp Arg Val Met Ser Tyr Leu Asn Ala Ser
            980                 985
```

<210> SEQ ID NO 45
<211> LENGTH: 1812
<212> TYPE: DNA
<213> ORGANISM: Artificial Sequence
<220> FEATURE:
<223> OTHER INFORMATION: DNA sequence of polypeptide chain H9a

<400> SEQUENCE: 45

```
gaagtgcagc tgcagcagtc cggccccgga ctggtcaaac cctcccagac cctgtctctt     60

acctgcgcca tctccggcga ctctgtgtcc agcaactctg ccgcttggaa ttggatccgg    120

cagtctccta gtagaggcct ggaatggctg ggcaagacat actaccggtt caagtggtat    180

tccgattacg ccgtgtccgt gaagggcaga atcaccatca accctgatac ctctaagaat    240

caattctccc tgcagctgaa ctccgtgacc cctgaggaca ccgctgtgtt ttactgcacc    300

agagagagca ccacctacga cctgctggct ggccctttcg actactgggg ccagggaaca    360
```

```
ctcgtcaccg tgtcttccgc ctctacaaag ggcccatccg tttttcctct ggccccgtcc    420

tctaagtcta cctctggcgg caccgccgct ctgggctgcc tggtgaagga ctacttcccc    480

gagcctgtga ccgtgtcctg gaacagcggc gctctgacct ccggcgtgca taccttccct    540

gctgttctgc aatcttctgg cctgtactct ctgtcctctg tggtgaccgt gccttccagc    600

tctctgggca cccagaccta catctgcaac gtgaaccata agccttctaa cactaaggtg    660

gacaagaaag tggaacccaa gtcctgcgac aaaacccaca cctgtcctcc ttgtcctgcc    720

cctgagctgc tgggcggacc tagcgtgttc ctgttcccac ctaagcctaa ggataccctg    780

atgatctccc ggacccctga agtgacctgc gtggtcgtgg acgtgtctca cgaagatcct    840

gaagtcaagt tcaactggta cgtggatggc gtcgaggtgc acaacgccaa gaccaagccc    900

cgggaagagc agtacaactc cacatataga gtggtgagtg tgctgacagt actgcaccag    960

gactggctga acggcaaaga gtacaagtgc aaggtgtcca acaaggctct gcctgctcct   1020

atcgagaaga caatctccaa ggccaaggga cagcctagag aacctcaagt gtgcaccctc   1080

ccaccttctc gcgaggagat gaccaagaac caggtgagcc tgtcctgtgc tgtgaaaggc   1140

ttctacccct ccgacatcgc cgtggagtgg gagtccaatg gccagccaga gaacaactac   1200

aagaccacac ctcccgtgct ggactccgac ggctccttct tcctggtgtc caagctgacc   1260

gtggacaagt ctagatggca gcagggcaac gtgtttagct gctccgtgat gcacgaggcc   1320

ctgcacaacc actacaccca gaagtctctg tccctgagcc ctggatcagg tggaggcggt   1380

agtggcggag gcggttcagg cggaggcgga tctgcaccta cttcaagttc tacaaagaaa   1440

acacagctac aactggagca tttactgctg gatttacaga tgattttgaa tggaattaat   1500

aattacaaga atcccaaact caccaggatg ctcacattta agttttacat gcccaagaag   1560

gccacagaac tgaaacatct tcagtgtcta gaagaagaac tcaaacctct ggaggaagtg   1620

ctaaatttag ctcaaagcaa aaactttcac ttaagaccca gggacttaat cagcaatatc   1680

aacgtaatag ttctggaact aaagggatct gaaacaacat tcatgtgtga atatgctgat   1740

gagacagcaa ccattgtaga atttctgaac agatggatta ccttttgtca aagcatcatc   1800

tcaacactga ct                                                       1812
```

```
<210> SEQ ID NO 46
<211> LENGTH: 604
<212> TYPE: PRT
<213> ORGANISM: Artificial Sequence
<220> FEATURE:
<223> OTHER INFORMATION: Amino acid sequence of polypeptide chain H9a

<400> SEQUENCE: 46

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

```
Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Cys Thr Leu Pro Pro Ser Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Ser Gly Gly Gly Gly Ser Gly Gly Gly
    450                 455                 460

Gly Ser Gly Gly Gly Gly Ser Ala Pro Thr Ser Ser Ser Thr Lys Lys
465                 470                 475                 480

Thr Gln Leu Gln Leu Glu His Leu Leu Leu Asp Leu Gln Met Ile Leu
                485                 490                 495

Asn Gly Ile Asn Asn Tyr Lys Asn Pro Lys Leu Thr Arg Met Leu Thr
            500                 505                 510

Phe Lys Phe Tyr Met Pro Lys Lys Ala Thr Glu Leu Lys His Leu Gln
```

```
        515                 520                 525

Cys Leu Glu Glu Glu Leu Lys Pro Leu Glu Glu Val Leu Asn Leu Ala
    530                 535                 540

Gln Ser Lys Asn Phe His Leu Arg Pro Arg Asp Leu Ile Ser Asn Ile
545                 550                 555                 560

Asn Val Ile Val Leu Glu Leu Lys Gly Ser Glu Thr Thr Phe Met Cys
                565                 570                 575

Glu Tyr Ala Asp Glu Thr Ala Thr Ile Val Glu Phe Leu Asn Arg Trp
            580                 585                 590

Ile Thr Phe Cys Gln Ser Ile Ile Ser Thr Leu Thr
        595                 600
```

<210> SEQ ID NO 47
<211> LENGTH: 1812
<212> TYPE: DNA
<213> ORGANISM: Artificial Sequence
<220> FEATURE:
<223> OTHER INFORMATION: DNA sequence of polypeptide chain H8b

<400> SEQUENCE: 47

```
gaagtgcagc tgcagcagtc cggccccgga ctggtcaaac cctcccagac cctgtctctt     60

acctgcgcca tctccggcga ctctgtgtcc agcaactctg ccgcttggaa ttggatccgg    120

cagtctccta gtagaggcct ggaatggctg ggcaagacat actaccggtt caagtggtat    180

tccgattacg ccgtgtccgt gaagggcaga atcaccatca accctgatac ctctaagaat    240

caattctccc tgcagctgaa ctccgtgacc cctgaggaca ccgctgtgtt ttactgcacc    300

agagagagca ccacctacga cctgctggct ggccctttcg actactgggg ccagggaaca    360

ctcgtcaccg tgtcttccgc ctctacaaag ggcccatccg tttttcctct ggccccgtcc    420

tctaagtcta cctctggcgg caccgccgct ctgggctgcc tggtgaagga ctacttcccc    480

gagcctgtga ccgtgtcctg gaacagcggc gctctgacct ccggcgtgca taccttccct    540

gctgttctgc aatcttctgg cctgtactct ctgtcctctg tggtgaccgt gccttccagc    600

tctctgggca cccagaccta catctgcaac gtgaaccata agccttctaa cactaaggtg    660

gacaagaaag tggaacccaa gtcctgcgac aaaacccaca cctgtcctcc ttgtcctgcc    720

cctgagctgc tgggcggacc tagcgtgttc ctgttcccac ctaagcctaa ggataccctg    780

atgatctccc ggacccctga agtgacctgc gtggtcgtgg acgtgtctca cgaagatcct    840

gaagtcaagt tcaactggta cgtggatggc gtcgaggtgc acaacgccaa gaccaagccc    900

cgggaagagc agtacaactc cacatataga gtggtgagtg tgctgacagt actgcaccag    960

gactggctga acggcaaaga gtacaagtgc aaggtgtcca acaaggctct gcctgctcct   1020

atcgagaaga caatctccaa ggccaaggga cagcctagag aacctcaagt gtacaccctc   1080

ccaccttgtc gcgaggagat gaccaagaac caggtgagcc tgtggtgtct ggtgaaaggc   1140

ttctacccct ccgacatcgc cgtggagtgg gagtccaatg gccagccaga gaacaactac   1200

aagaccacac ctcccgtgct ggactccgac ggctccttct tcctgtactc caagctgacc   1260

gtggacaagt ctagatggca gcagggcaac gtgtttagct gctccgtgat gcacgaggcc   1320

ctgcacaacc actacaccca gaagtctctg tccctgagcc ctggatcagg tggaggcggt   1380

agtggcggag gcggttcagg cggaggcgga tctgcaccta cttcaagttc tacaaagaaa   1440

acacagctac aactggagca tttactgctg gatttacaga tgattttgaa tggaattaat   1500

aattacaaga atcccaaact caccaggatg ctcacattta agttttacat gcccaagaag   1560
```

```
gccacagaac tgaaacatct tcagtgtcta gaagaagaac tcaaacctct ggaggaagtg   1620

ctaaatttag ctcaaagcaa aaactttcac ttaagaccca gggacttaat cagcaatatc   1680

aacgtaatag ttctggaact aaagggatct gaaacaacat tcatgtgtga atatgctgat   1740

gagacagcaa ccattgtaga atttctgaac agatggatta ccttttgtca aagcatcatc   1800

tcaacactga ct                                                       1812
```

```
<210> SEQ ID NO 48
<211> LENGTH: 604
<212> TYPE: PRT
<213> ORGANISM: Artificial Sequence
<220> FEATURE:
<223> OTHER INFORMATION: Amino acid sequence of polypeptide chain H8b

<400> SEQUENCE: 48

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Cys Arg Glu Glu Met Thr
        355                 360                 365

Lys Asn Gln Val Ser Leu Trp Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Ser Gly Gly Gly Gly Ser Gly Gly Gly
    450                 455                 460

Gly Ser Gly Gly Gly Gly Ser Ala Pro Thr Ser Ser Ser Thr Lys Lys
465                 470                 475                 480

Thr Gln Leu Gln Leu Glu His Leu Leu Leu Asp Leu Gln Met Ile Leu
                485                 490                 495

Asn Gly Ile Asn Asn Tyr Lys Asn Pro Lys Leu Thr Arg Met Leu Thr
            500                 505                 510

Phe Lys Phe Tyr Met Pro Lys Lys Ala Thr Glu Leu Lys His Leu Gln
        515                 520                 525

Cys Leu Glu Glu Glu Leu Lys Pro Leu Glu Glu Val Leu Asn Leu Ala
    530                 535                 540

Gln Ser Lys Asn Phe His Leu Arg Pro Arg Asp Leu Ile Ser Asn Ile
545                 550                 555                 560

Asn Val Ile Val Leu Glu Leu Lys Gly Ser Glu Thr Thr Phe Met Cys
                565                 570                 575

Glu Tyr Ala Asp Glu Thr Ala Thr Ile Val Glu Phe Leu Asn Arg Trp
            580                 585                 590

Ile Thr Phe Cys Gln Ser Ile Ile Ser Thr Leu Thr
        595                 600
```

<210> SEQ ID NO 49
<211> LENGTH: 1332
<212> TYPE: DNA
<213> ORGANISM: Artificial Sequence
<220> FEATURE:
<223> OTHER INFORMATION: DNA sequence of polypeptide chain H10

<400> SEQUENCE: 49

```
gaagtgcagc tggtggaatc tggcggagga ctggttcaac ctggcggctc tctgagactg     60

tcttgtgccg ccagcggctt cgtgttcagc agatacgata tggcctgggt ccgacaggcc    120

cctggcaaag gacttgagtg ggtgtccttt atcagcggcg gaggcagcaa cacctactat    180

cccgataccg tgaagggcag attcaccatc agccgggaca acagcaagaa caccctgtac    240

ctgcagatga acagcctgag agccgaggac accgccgtgt actactgcat cagcccctac    300

tactacgcca tggaatactg gggccagggc accaccgtga cagtgtctag cgcctctaca    360

aagggcccca gcgttttccc actggctccc tgtagcagaa gcaccagcga atctacagcc    420
```

```
gctctgggct gcctggtcaa ggactacttt cctgagcctg tgaccgtgtc ctggaactct    480

ggcgctctga caagcggagt gcacaccttt ccagccgtgc tgcaaagcag cggcctgtac    540

tctctgagca gcgtggtcac agtgcctagc tctagcctgg gcaccaagac ctacacctgt    600

aatgtggacc acaagcctag caacaccaag gtggacaagc gcgtggaatc taagtacggc    660

cctccttgtc ctccatgtcc tgcacctgag tttctcggcg gaccctccgt gttcctgttt    720

cctccaaagc ctaaggatac cctgatgatc agcagaaccc ctgaagtgac ctgcgtggtg    780

gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020

agagaacccc aggtgtacac actgcctcca agccaagagg aaatgaccaa gaaccaggtg   1080

tccctgacct gcctcgtgaa gggattctac cccctccgata tcgccgtgga atgggagagc   1140

aatggacagc ccgagaacaa ctacaagaca acccctcctg tgctggacag cgacggctca   1200

ttcttcctgt acagcagact gaccgtggac aagagcagat ggcaagaggg caacgtgttc   1260

tcctgcagcg tgatgcacga ggccctgcac aaccactaca cccagaagtc tctgtccctg   1320

tctctgggca ag                                                      1332
```

<210> SEQ ID NO 50
<211> LENGTH: 444
<212> TYPE: PRT
<213> ORGANISM: Artificial Sequence
<220> FEATURE:
<223> OTHER INFORMATION: Amino acid sequence of polypeptide chain H10

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
```

```
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 51
<211> LENGTH: 642
<212> TYPE: DNA
<213> ORGANISM: Artificial Sequence
<220> FEATURE:
<223> OTHER INFORMATION: DNA sequence of polypeptide chain L4

<400> SEQUENCE: 51

gacatccaga tgacacagag ccctagcagc gtgtccgcct ctgtgggaga cagagtgacc     60

atcacatgca aggccagcca ggatgtggat acagccgtgg cctggtatca gcagaagcct    120

ggaaaggccc ctaagctgct gatctactgg gccagcacaa gacacacagg cgtgcccagc    180

agattttctg gcagcggctc tggcaccgac ttcaccctga ccatatctag cctgcagcct    240

gaggacttcg ccacctacta ctgccagcag tacagcacat tcccctggac ctttggcgga    300

ggcaccaagg tggaaatcaa gcggacagtg gccgctccta gcgtgttcat ctttccacct    360

agcgacgagc agctgaagtc cggcacagcc tctgttgtgt gcctgctgaa caacttctac    420

cccagagaag ccaaggtgca gtggaaggtg gacaacgccc tgcagagcgg caatagccaa    480

gagtctgtga ccgagcagga cagcaaggac tctacctaca gcctgtccag cacactgacc    540

ctgagcaagg ccgactacga gaagcacaaa gtgtacgcct gcgaagtgac ccaccagggc    600

ctttctagcc ctgtgaccaa gagcttcaac cggggcgaat gt                       642
```

<210> SEQ ID NO 52
<211> LENGTH: 214
<212> TYPE: PRT
<213> ORGANISM: Artificial Sequence
<220> FEATURE:
<223> OTHER INFORMATION: Amino acid sequence of polypeptide chain L4

<400> SEQUENCE: 52

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 53
<211> LENGTH: 1329
<212> TYPE: DNA
<213> ORGANISM: Artificial Sequence
<220> FEATURE:
<223> OTHER INFORMATION: DNA sequence of polypeptide chain H11

<400> SEQUENCE: 53

```
gaagtgcagc tggtggaatc tggcggagga ctggttcaac ctggcggctc tctgagactg     60

tcttgtgccg ccagcggctt cgtgttcagc agatacgata tggcctgggt ccgacaggcc    120

cctggcaaag gacttgagtg ggtgtccttt atcagcggcg gaggcagcaa cacctactat    180

cccgataccg tgaagggcag attcaccatc agccgggaca acagcaagaa caccctgtac    240

ctgcagatga acagcctgag agccgaggac accgccgtgt actactgcat cagcccctac    300

tactacgcca tggaatactg gggccagggc accaccgtga cagtgtctag cgcctctaca    360

aagggcccca gcgttttccc actggctccc tgtagcagaa gcaccagcga atctacagcc    420

gctctgggct gcctggtcaa ggactacttt cctgagcctg tgaccgtgtc ctggaactct    480

ggcgctctga caagcggagt gcacaccttt ccagccgtgc tgcaaagcag cggcctgtac    540
```

```
tctctgagca gcgtggtcac agtgcctagc tctagcctgg gcaccaagac ctacacctgt    600

aatgtggacc acaagcctag caacaccaag gtggacaagc gcgtggaatc taagtacggc    660

cctccttgtc ctccatgtcc tgcacctgag tttctcggcg gaccctccgt gttcctgttt    720

cctccaaagc ctaaggatac cctgatgatc agcagaaccc ctgaagtgac ctgcgtggtg    780

gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020

agagaacccc aggtgtacac actgcctcca tgccaagagg aaatgaccaa gaaccaggtg   1080

tccctgtggt gcctcgtgaa gggattctac ccctccgata tcgccgtgga atgggagagc   1140

aatggacagc ccgagaacaa ctacaagaca acccctcctg tgctggacag cgacggctca   1200

ttcttcctgt acagcagact gaccgtggac aagagcagat ggcaagaggg caacgtgttc   1260

tcctgcagcg tgatgcacga ggccctgcac aaccactaca cccagaagtc tctgtccctg   1320

tctctgggc                                                            1329
```

```
<210> SEQ ID NO 54
<211> LENGTH: 443
<212> TYPE: PRT
<213> ORGANISM: Artificial Sequence
<220> FEATURE:
<223> OTHER INFORMATION: Amino acid sequence of polypeptide chain H11

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
```

```
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Cys Gln
            340                 345                 350

Glu Glu Met Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 55
<211> LENGTH: 1329
<212> TYPE: DNA
<213> ORGANISM: Artificial Sequence
<220> FEATURE:
<223> OTHER INFORMATION: DNA sequence of polypeptide chain H12

<400> SEQUENCE: 55

```
gaagtgcagc tggtggaatc tggcggagga ctggttcaac ctggcggctc tctgagactg      60

tcttgtgccg ccagcggctt cgtgttcagc agatacgata tggcctgggt ccgacaggcc     120

cctggcaaag gacttgagtg ggtgtccttt atcagcggcg gaggcagcaa cacctactat     180

cccgataccg tgaagggcag attcaccatc agccgggaca acagcaagaa caccctgtac     240

ctgcagatga acagcctgag agccgaggac accgccgtgt actactgcat cagcccctac     300

tactacgcca tggaatactg gggccagggc accaccgtga cagtgtctag cgcctctaca     360

aagggcccca gcgttttccc actggctccc tgtagcagaa gcaccagcga atctacagcc     420

gctctgggct gcctggtcaa ggactacttt cctgagcctg tgaccgtgtc ctggaactct     480

ggcgctctga caagcggagt gcacaccttt ccagccgtgc tgcaaagcag cggcctgtac     540

tctctgagca gcgtggtcac agtgcctagc tctagcctgg gcaccaagac ctacacctgt     600

aatgtggacc acaagcctag caacaccaag gtggacaagc gcgtggaatc taagtacggc     660

cctccttgtc ctccatgtcc tgcacctgag tttctcggcg gaccctccgt gttcctgttt     720

cctccaaagc ctaaggatac cctgatgatc agcagaaccc ctgaagtgac ctgcgtggtg     780
```

```
gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020

agagaacccc aggtgtgcac actgcctcca agccaagagg aaatgaccaa gaaccaggtg   1080

tccctgtcct gcgccgtgaa gggattctac ccctccgata tcgccgtgga atgggagagc   1140

aatggacagc ccgagaacaa ctacaagaca acccctcctg tgctggacag cgacggctca   1200

ttcttcctgg tgagcagact gaccgtggac aagagcagat ggcaagaggg caacgtgttc   1260

tcctgcagcg tgatgcacga ggccctgcac aaccactaca cccagaagtc tctgtccctg   1320

tctctgggc                                                           1329
```

<210> SEQ ID NO 56
<211> LENGTH: 443
<212> TYPE: PRT
<213> ORGANISM: Artificial Sequence
<220> FEATURE:
<223> OTHER INFORMATION: Amino acid sequence of polypeptide chain H12

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

```
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Cys Thr Leu Pro Pro Ser Gln
            340                 345                 350

Glu Glu Met Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 57
<211> LENGTH: 2931
<212> TYPE: DNA
<213> ORGANISM: Artificial Sequence
<220> FEATURE:
<223> OTHER INFORMATION: DNA sequence of polypeptide chain H11a

<400> SEQUENCE: 57

```
gaagtgcagc tggtggaatc tggcggagga ctggttcaac ctggcggctc tctgagactg     60

tcttgtgccg ccagcggctt cgtgttcagc agatacgata tggcctgggt ccgacaggcc    120

cctggcaaag gacttgagtg ggtgtccttt atcagcggcg gaggcagcaa cacctactat    180

cccgataccg tgaagggcag attcaccatc agccgggaca acagcaagaa caccctgtac    240

ctgcagatga acagcctgag agccgaggac accgccgtgt actactgcat cagcccctac    300

tactacgcca tggaatactg gggccagggc accaccgtga cagtgtctag cgcctctaca    360

aagggcccca gcgttttccc actggctccc tgtagcagaa gcaccagcga atctacagcc    420

gctctgggct gcctggtcaa ggactacttt cctgagcctg tgaccgtgtc ctggaactct    480

ggcgctctga caagcggagt gcacaccttt ccagccgtgc tgcaaagcag cggcctgtac    540

tctctgagca gcgtggtcac agtgcctagc tctagcctgg gcaccaagac ctacacctgt    600

aatgtggacc acaagcctag caacaccaag gtggacaagc gcgtggaatc taagtacggc    660

cctccttgtc ctccatgtcc tgcacctgag tttctcggcg gaccctccgt gttcctgttt    720

cctccaaagc ctaaggatac cctgatgatc agcagaaccc ctgaagtgac ctgcgtggtg    780

gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020
```

```
agagaacccc aggtgtacac actgcctcca tgccaagagg aaatgaccaa gaaccaggtg   1080

tccctgtggt gcctcgtgaa gggattctac ccctccgata tcgccgtgga atgggagagc   1140

aatggacagc ccgagaacaa ctacaagaca acccctcctg tgctggacag cgacggctca   1200

ttcttcctgt acagcagact gaccgtggac aagagcagat ggcaagaggg caacgtgttc   1260

tcctgcagcg tgatgcacga ggccctgcac aaccactaca cccagaagtc tctgtccctg   1320

tctctgggct caggtggagg cggtagtggc ggaggcggtt caggcggagg cggatctatt   1380

tgggagctga agaaagacgt gtacgtggtc gagctggact ggtaccctga tgccccaggc   1440

gagatggtcg tgctgacctg cgatacacca gaggaagatg gtatcacctg gacactggat   1500

cagtcctcag aggtgctggg ctctggtaaa acactgacca ttcaggtgaa ggagttcggt   1560

gacgctggac agtacacttg tcataagggc ggggaggtgc tgtctcactc cctgctgctg   1620

ctgcataaga aggaggatgg aatctggtcc actgacatcc tgaaagacca gaaggagcca   1680

aagaacaaaa ccttcctgcg atgcgaggct aagaactaca gcggccgctt tacatgctgg   1740

tggctgacaa ccatcagcac cgatctgacc tttagcgtga agtcatccag gggcagttca   1800

gaccctcagg gagtcacatg tggcgccgca accctgtcag cagagcgagt gcggggagac   1860

aataaggaat acgagtacag cgtcgagtgt caggaggatt ccgcatgtcc agctgcagaa   1920

gaatccctgc ctatcgaagt catggtggac gctgtgcata aactgaagta cgagaattac   1980

accagcagct tttcatccgg ggacatcatc aagcccgatc cacctaagaa tctgcagctg   2040

aagcctctga aaaatagccg acaggtcgaa gtgtcatggg aatacccaga cacctggtca   2100

acaccacact cctacttctc cctgaccttc tgtgtgcagg tccagggaaa aagcaagcgg   2160

gaaaagaaag atcgggtgtt caccgacaag accagtgcta cagtgatttg ccggaagaat   2220

gccagcattt ctgtcagagc tcaggaccgg tactatagct cttcctggag cgagtgggct   2280

tcagtgccat gttctggagg cggtggatct ggcggaggtg gaagcggagg cggtggatct   2340

agaaacctgc ccgtcgcaac ccctgatcca gggatgttcc cctgtctgca tcacagccag   2400

aatctgctga gggctgtctc caacatgctg cagaaggctc gacagaccct ggagttctac   2460

ccatgtacca gcgaagagat cgaccacgag gatatcacaa aggataaaac cagcacagtg   2520

gaagcatgcc tgcctctgga actgaccaag aatgagagct gcctgaatag cagggagacc   2580

tccttcatca ccaacggctc atgcctggct tcaaggaaga ccagcttcat gatggctctg   2640

tgtctgagct ctatctatga ggacctgaag atgtaccagg tggagttcaa gaccatgaac   2700

gccaagctgc tgatggatcc aaagaggcag atcttcctgg atcagaatat gctggcagtg   2760

atcgatgagc tgatgcaggc cctgaatttt aacagtgaga cagtgcctca gaagagctct   2820

ctggaagagc cagactttta caaaactaag atcaagctgt gcattctgct gcacgctttc   2880

cgcatcagag ctgtcactat cgatagagtg atgagctatc tgaatgcctc a            2931
```

<210> SEQ ID NO 58
<211> LENGTH: 977
<212> TYPE: PRT
<213> ORGANISM: Artificial Sequence
<220> FEATURE:
<223> OTHER INFORMATION: Amino acid sequence of polypeptide chain H11a

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
```

-continued

```
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Cys Gln
            340                 345                 350

Glu Glu Met Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ser Gly Gly Gly Gly
        435                 440                 445
```

```
Ser Gly Gly Gly Gly Ser Gly Gly Gly Gly Ser Ile Trp Glu Leu Lys
    450                 455                 460

Lys Asp Val Tyr Val Val Glu Leu Asp Trp Tyr Pro Asp Ala Pro Gly
465                 470                 475                 480

Glu Met Val Val Leu Thr Cys Asp Thr Pro Glu Glu Asp Gly Ile Thr
                485                 490                 495

Trp Thr Leu Asp Gln Ser Ser Glu Val Leu Gly Ser Gly Lys Thr Leu
            500                 505                 510

Thr Ile Gln Val Lys Glu Phe Gly Asp Ala Gly Gln Tyr Thr Cys His
        515                 520                 525

Lys Gly Gly Glu Val Leu Ser His Ser Leu Leu Leu Leu His Lys Lys
    530                 535                 540

Glu Asp Gly Ile Trp Ser Thr Asp Ile Leu Lys Asp Gln Lys Glu Pro
545                 550                 555                 560

Lys Asn Lys Thr Phe Leu Arg Cys Glu Ala Lys Asn Tyr Ser Gly Arg
                565                 570                 575

Phe Thr Cys Trp Trp Leu Thr Thr Ile Ser Thr Asp Leu Thr Phe Ser
            580                 585                 590

Val Lys Ser Ser Arg Gly Ser Ser Asp Pro Gln Gly Val Thr Cys Gly
        595                 600                 605

Ala Ala Thr Leu Ser Ala Glu Arg Val Arg Gly Asp Asn Lys Glu Tyr
    610                 615                 620

Glu Tyr Ser Val Glu Cys Gln Glu Asp Ser Ala Cys Pro Ala Ala Glu
625                 630                 635                 640

Glu Ser Leu Pro Ile Glu Val Met Val Asp Ala Val His Lys Leu Lys
                645                 650                 655

Tyr Glu Asn Tyr Thr Ser Ser Phe Phe Ile Arg Asp Ile Ile Lys Pro
            660                 665                 670

Asp Pro Pro Lys Asn Leu Gln Leu Lys Pro Leu Lys Asn Ser Arg Gln
        675                 680                 685

Val Glu Val Ser Trp Glu Tyr Pro Asp Thr Trp Ser Thr Pro His Ser
    690                 695                 700

Tyr Phe Ser Leu Thr Phe Cys Val Gln Val Gln Gly Lys Ser Lys Arg
705                 710                 715                 720

Glu Lys Lys Asp Arg Val Phe Thr Asp Lys Thr Ser Ala Thr Val Ile
                725                 730                 735

Cys Arg Lys Asn Ala Ser Ile Ser Val Arg Ala Gln Asp Arg Tyr Tyr
            740                 745                 750

Ser Ser Ser Trp Ser Glu Trp Ala Ser Val Pro Cys Ser Gly Gly Gly
        755                 760                 765

Gly Ser Gly Gly Gly Gly Ser Gly Gly Gly Gly Ser Arg Asn Leu Pro
    770                 775                 780

Val Ala Thr Pro Asp Pro Gly Met Phe Pro Cys Leu His His Ser Gln
785                 790                 795                 800

Asn Leu Leu Arg Ala Val Ser Asn Met Leu Gln Lys Ala Arg Gln Thr
                805                 810                 815

Leu Glu Phe Tyr Pro Cys Thr Ser Glu Glu Ile Asp His Glu Asp Ile
            820                 825                 830

Thr Lys Asp Lys Thr Ser Thr Val Glu Ala Cys Leu Pro Leu Glu Leu
        835                 840                 845

Thr Lys Asn Glu Ser Cys Leu Asn Ser Arg Glu Thr Ser Phe Ile Thr
    850                 855                 860
```

```
Asn Gly Ser Cys Leu Ala Ser Arg Lys Thr Ser Phe Met Met Ala Leu
865                 870                 875                 880

Cys Leu Ser Ser Ile Tyr Glu Asp Leu Lys Met Tyr Gln Val Glu Phe
                885                 890                 895

Lys Thr Met Asn Ala Lys Leu Leu Met Asp Pro Lys Arg Gln Ile Phe
            900                 905                 910

Leu Asp Gln Asn Met Leu Ala Val Ile Asp Glu Leu Met Gln Ala Leu
        915                 920                 925

Asn Phe Asn Ser Glu Thr Val Pro Gln Lys Ser Ser Leu Glu Glu Pro
    930                 935                 940

Asp Phe Tyr Lys Thr Lys Ile Lys Leu Cys Ile Leu Leu His Ala Phe
945                 950                 955                 960

Arg Ile Arg Ala Val Thr Ile Asp Arg Val Met Ser Tyr Leu Asn Ala
                965                 970                 975

Ser


<210> SEQ ID NO 59
<211> LENGTH: 1776
<212> TYPE: DNA
<213> ORGANISM: Artificial Sequence
<220> FEATURE:
<223> OTHER INFORMATION: DNA sequence of polypeptide chain H12a

<400> SEQUENCE: 59

gaagtgcagc tggtggaatc tggcggagga ctggttcaac ctggcggctc tctgagactg     60

tcttgtgccg ccagcggctt cgtgttcagc agatacgata tggcctgggt ccgacaggcc    120

cctggcaaag gacttgagtg ggtgtccttt atcagcggcg gaggcagcaa cacctactat    180

cccgataccg tgaagggcag attcaccatc agccgggaca acagcaagaa caccctgtac    240

ctgcagatga acagcctgag agccgaggac accgccgtgt actactgcat cagcccctac    300

tactacgcca tggaatactg gggccagggc accaccgtga cagtgtctag cgcctctaca    360

aagggcccca gcgttttccc actggctccc tgtagcagaa gcaccagcga atctacagcc    420

gctctgggct gcctggtcaa ggactacttt cctgagcctg tgaccgtgtc ctggaactct    480

ggcgctctga caagcggagt gcacaccttt ccagccgtgc tgcaaagcag cggcctgtac    540

tctctgagca gcgtggtcac agtgcctagc tctagcctgg gcaccaagac ctacacctgt    600

aatgtggacc acaagcctag caacaccaag gtggacaagc gcgtggaatc taagtacggc    660

cctccttgtc ctccatgtcc tgcacctgag tttctcggcg gaccctccgt gttcctgttt    720

cctccaaagc ctaaggatac cctgatgatc agcagaaccc ctgaagtgac ctgcgtggtg    780

gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020

agagaacccc aggtgtgcac actgcctcca agccaagagg aaatgaccaa gaaccaggtg   1080

tccctgtcct gcgccgtgaa gggattctac ccctccgata tcgccgtgga atgggagagc   1140

aatggacagc ccgagaacaa ctacaagaca acccctcctg tgctggacag cgacggctca   1200

ttcttcctgg tgagcagact gaccgtggac aagagcagat ggcaagaggg caacgtgttc   1260

tcctgcagcg tgatgcacga ggccctgcac aaccactaca cccagaagtc tctgtccctg   1320

tctctgggct caggtggagg cggtagtggc ggaggcggtt caggcggagg cggatctgca   1380
```

```
cctacttcaa gttctacaaa gaaaacacag ctacaactgg agcatttact gctggattta   1440

cagatgattt tgaatggaat taataattac aagaatccca aactcaccag gatgctcaca   1500

tttaagtttt acatgcccaa gaaggccaca gaactgaaac atcttcagtg tctagaagaa   1560

gaactcaaac ctctggagga agtgctaaat ttagctcaaa gcaaaaactt tcacttaaga   1620

cccagggact taatcagcaa tatcaacgta atagttctgg aactaaaggg atctgaaaca   1680

acattcatgt gtgaatatgc tgatgagaca gcaaccattg tagaatttct gaacagatgg   1740

attacctttt gtcaaagcat catctcaaca ctgact                              1776
```

<210> SEQ ID NO 60
<211> LENGTH: 592
<212> TYPE: PRT
<213> ORGANISM: Artificial Sequence
<220> FEATURE:
<223> OTHER INFORMATION: Amino acid sequence of polypeptide chain H12a

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
```

```
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Cys Thr Leu Pro Pro Ser Gln
            340                 345                 350

Glu Glu Met Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ser Gly Gly Gly Gly
        435                 440                 445

Ser Gly Gly Gly Gly Ser Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 61
<211> LENGTH: 1776
<212> TYPE: DNA
<213> ORGANISM: Artificial Sequence
<220> FEATURE:
<223> OTHER INFORMATION: DNA sequence of polypeptide chain H11b

<400> SEQUENCE: 61

gaagtgcagc tggtggaatc tggcggagga ctggttcaac ctggcggctc tctgagactg      60

tcttgtgccg ccagcggctt cgtgttcagc agatacgata tggcctgggt ccgacaggcc     120

cctggcaaag gacttgagtg ggtgtccttt atcagcggcg gaggcagcaa cacctactat     180

cccgataccg tgaagggcag attcaccatc agccgggaca acagcaagaa caccctgtac     240

ctgcagatga acagcctgag agccgaggac accgccgtgt actactgcat cagcccctac     300

tactacgcca tggaatactg gggccagggc accaccgtga cagtgtctag cgcctctaca     360

aagggcccca gcgttttccc actggctccc tgtagcagaa gcaccagcga atctacagcc     420
```

```
gctctgggct gcctggtcaa ggactacttt cctgagcctg tgaccgtgtc ctggaactct    480

ggcgctctga caagcggagt gcacaccttt ccagccgtgc tgcaaagcag cggcctgtac    540

tctctgagca gcgtggtcac agtgcctagc tctagcctgg gcaccaagac ctacacctgt    600

aatgtggacc acaagcctag caacaccaag gtggacaagc gcgtggaatc taagtacggc    660

cctccttgtc ctccatgtcc tgcacctgag tttctcggcg gaccctccgt gttcctgttt    720

cctccaaagc ctaaggatac cctgatgatc agcagaaccc ctgaagtgac ctgcgtggtg    780

gtggacgtgt cccaagagga tcctgaggtg cagttcaatt ggtacgtgga cggcgtggaa    840

gtgcacaacg ccaagaccaa gcctagagag gaacagttca acagcaccta cagagtggtg    900

tccgtgctga cagtgctgca ccaggattgg ctgaacggca aagagtacaa gtgcaaggtg    960

tccaacaagg gcctgcctag cagcatcgag aaaaccatca gcaaggccaa gggccagcca   1020

agagaacccc aggtgtacac actgcctcca tgccaagagg aaatgaccaa gaaccaggtg   1080

tccctgtggt gcctcgtgaa gggattctac cctccgata tcgccgtgga atgggagagc   1140

aatggacagc ccgagaacaa ctacaagaca acccctcctg tgctggacag cgacggctca   1200

ttcttcctgt acagcagact gaccgtggac aagagcagat ggcaagaggg caacgtgttc   1260

tcctgcagcg tgatgcacga ggccctgcac aaccactaca cccagaagtc tctgtccctg   1320

tctctgggct caggtggagg cggtagtggc ggaggcggtt caggcggagg cggatctgca   1380

cctacttcaa gttctacaaa gaaaacacag ctacaactgg agcatttact gctggattta   1440

cagatgattt tgaatggaat taataattac aagaatccca aactcaccag gatgctcaca   1500

tttaagtttt acatgcccaa gaaggccaca gaactgaaac atcttcagtg tctagaagaa   1560

gaactcaaac ctctggagga agtgctaaat ttagctcaaa gcaaaaactt tcacttaaga   1620

cccagggact taatcagcaa tatcaacgta atagttctgg aactaaaggg atctgaaaca   1680

acattcatgt gtgaatatgc tgatgagaca gcaaccattg tagaatttct gaacagatgg   1740

attacctttt gtcaaagcat catctcaaca ctgact                             1776
```

<210> SEQ ID NO 62
<211> LENGTH: 592
<212> TYPE: PRT
<213> ORGANISM: Artificial Sequence
<220> FEATURE:
<223> OTHER INFORMATION: Amino acid sequence of polypeptide chain H11b

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
```

```
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Cys Gln
            340                 345                 350

Glu Glu Met Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Ser Gly Gly Gly Gly
        435                 440                 445

Ser Gly Gly Gly Gly Ser Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540
```

```
Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 63
<211> LENGTH: 16
<212> TYPE: PRT
<213> ORGANISM: Artificial Sequence
<220> FEATURE:
<223> OTHER INFORMATION: Linker sequence

<400> SEQUENCE: 63

Ser Gly Gly Gly Gly Ser Gly Gly Gly Gly Ser Gly Gly Gly Gly Ser
1               5                   10                  15


<210> SEQ ID NO 64
<211> LENGTH: 16
<212> TYPE: PRT
<213> ORGANISM: Artificial Sequence
<220> FEATURE:
<223> OTHER INFORMATION: Linker sequence
<220> FEATURE:
<221> NAME/KEY: VARIANT
<222> LOCATION: (7)..(16)
<223> OTHER INFORMATION: Up to 2 copies of GGGGS can be deleted

<400> SEQUENCE: 64

Ser Gly Gly Gly Gly Ser Gly Gly Gly Gly Ser Gly Gly Gly Gly Ser
1               5                   10                  15


<210> SEQ ID NO 65
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: VARIANT
<222> LOCATION: (6)..(15)
<223> OTHER INFORMATION: Up to 2 copies of GGGGS can be deleted

<400> SEQUENCE: 65

Gly Gly Gly Gly Ser Gly Gly Gly Gly Ser Gly Gly Gly Gly Ser
1               5                   10                  15


<210> SEQ ID NO 66
<211> LENGTH: 12
<212> TYPE: PRT
<213> ORGANISM: Artificial Sequence
<220> FEATURE:
<223> OTHER INFORMATION: Linker sequence

<400> SEQUENCE: 66

Lys Arg Val Ala Pro Glu Leu Leu Gly Gly Pro Ser
1               5                   10


<210> SEQ ID NO 67
<211> LENGTH: 5
<212> TYPE: PRT
<213> ORGANISM: Artificial Sequence
<220> FEATURE:
<223> OTHER INFORMATION: Linker sequence

<400> SEQUENCE: 67
```

```
Ala Ser Thr Lys Gly
1               5


<210> SEQ ID NO 68
<211> LENGTH: 6
<212> TYPE: PRT
<213> ORGANISM: Artificial Sequence
<220> FEATURE:
<223> OTHER INFORMATION: Linker sequence

<400> SEQUENCE: 68

Asn Ser Pro Pro Ala Ala
1               5


<210> SEQ ID NO 69
<211> LENGTH: 15
<212> TYPE: PRT
<213> ORGANISM: Artificial Sequence
<220> FEATURE:
<223> OTHER INFORMATION: Linker sequence

<400> SEQUENCE: 69

Glu Pro Lys Ser Ser Asp Lys Thr His Thr Ser Pro Pro Ser Pro
1               5                   10                  15


<210> SEQ ID NO 70
<211> LENGTH: 12
<212> TYPE: PRT
<213> ORGANISM: Artificial Sequence
<220> FEATURE:
<223> OTHER INFORMATION: Linker sequence

<400> SEQUENCE: 70

Glu Arg Lys Ser Ser Val Glu Ser Pro Pro Ser Pro
1               5                   10


<210> SEQ ID NO 71
<211> LENGTH: 12
<212> TYPE: PRT
<213> ORGANISM: Artificial Sequence
<220> FEATURE:
<223> OTHER INFORMATION: Linker sequence

<400> SEQUENCE: 71

Glu Ser Lys Tyr Gly Pro Pro Ser Pro Pro Ser Pro
1               5                   10
```

MONOCLONAL ANTIBODY-CYTOKINE FUSION PROTEIN DIMER AND APPLICATION THEREOF

CROSS REFERENCE TO RELATED APPLICATIONS

This is the U.S. National Stage of International Application No. PCT/CN2020/097927 filed, Jun. 24, 2020, which was published in Chinese, which in turn claims the benefit of Chinese Application No. 201910549915.0 filed, Jun. 24, 2019.

TECHNICAL FIELD

The present invention relates to a fusion protein, especially a protein dimer based on monoclonal antibody and cytokine fusion and an application thereof.

INCORPORATION OF AN ELECTRONIC SEQUENCE LISTING

The contents of the electronic sequence listing, named “P10449-PI-U.S. Pat. No. 250,421. Amended Sequence Listing.txt”, having a size of 205, 640 bytes, and a Date of Creation of Apr. 28, 2025, is herein incorporated by reference in its entirety.

BACKGROUND

An immune system is a set of defense system in mammal bodies and can resist invasion of various pathogens and eliminate tumors. Antibody molecules play an important role in the immune system, for example, recognizing a tumor antigen and activating an immune response. Meanwhile, cytokines serve as immunomodulatory factors to be capable of regulating and controlling innate immunity and adaptive immunity at the same time, and also have significance which cannot be ignored in cancer immunotherapy. This kind of regulatory factors almost participate in various links of the immune system, and perform a powerful function in aspects of regulating and balancing the immune system. Interferon and IL-2 are first selected as cytokines to be applied to immunotherapy. IFN-α is used to treat various cancers, such as melanoma, renal cancer, follicular lymphoma, and chronic myelogenous leukemia, while IL-2 was approved by FDA in 1998 to be used to treat advanced metastatic melanoma, metastatic renal cancer and the like. Other cytokines, such as IL-7, IL-10, IL-12, IL-15 and IL-21, are also in a clinical testing stage. Therefore, the cytokines have a certain potential to be used in immunotherapy.

However, the immunotherapy based on the cytokines is severely hindered in clinical use, and is mainly enslaved to severe side effects and underperformed pharmacokinetic properties. Therefore, in order to improve the treatment effect of the cytokines, the cytokines frequently need to be transformed. At present, a common method is to adopt a method of antibody fusion, and the cytokines are targetedly delivered to specific parts through the antibody, thereby effectively reducing cytotoxicity, improving the pharmacokinetic properties, and then enhancing an immunoregulation function. Even so, after some cytokines are fused onto the antibody, the activity of the antibody will be reduced, thereby influencing an overall effect. In addition, some cytokines can only exert the respective optimal effect by combined use, but the prior art cannot meet this requirement.

In immunoregulation, activating and inhibiting an immune response are mainly regulated by two independent signaling pathways. A first signal is antigen-mediated. When a T cell receptor specifically recognizes and binds to an antigen peptide presented by MHC on surfaces of antigen-presenting cells (APC), the first signal is generated. A second signal is provided by the interaction between antigen-presenting cells and costimulatory molecules expressed on the surface of T cells. When the first and second signals are activated in sequence, the tumors can be killed by T cells. If the second signal is in lack, T cells will enter an unresponsive state or immune tolerance, and even cause programmed cell death.

As mentioned above, the second signaling pathway is very important for activating immune cells. Specifically, co-stimulatory and co-inhibitory receptors participate in the second signaling pathway, induce an immune response and regulation of antigen-receptor presentation, balance positive and negative signals while maintaining immune tolerance of autoantigens, and maximize the immune response to invaders. CD28 is a member of a CD28 family, is a major T cell costimulatory receptor, and is subjected to constitutive expression on initial CD4+ and CD8+ T cells. Cytotoxic T lymphocyte-associated antigen 4 (CTLA-4) molecules are also a member of the CD28 receptor family, but are coinhibitory receptors, and the molecules are subjected to constitutive expression on regulatory T cells (Treg) or are generated after the T cells are activated by CD28. Either CD28 or CTLA-4 can be combined with a B7.1 (CD80) or B7.2 (CD86) ligand so as to deliver activating or inhibiting signals in the T cells respectively.

Ligands of the CD28 receptor include CD80, CD86, a programmed death ligand 1 (PD-L1) and a programmed death ligand 2 (PD-L2). Among these is PD-L1, a transmembrane protein that binds to the inhibitory checkpoint molecule of PD-1 and suppresses the adaptive immune response by delivering an inhibitory “don't find me” signal. A PD-1/PD-L1 signaling pathway plays a critical role in development of immune tolerance, and prevents an overreaction of the immune system so as to avoid an autoimmune disease. However, it is usually deregulated in a cancer progress, and tumor cells are allowed to disguise as healthy tissues to circumvent a protection mechanism. The tumor cells with overexpression of PD-L1 can escape T cell mediated death by activating the PD-1/PD-L1 inhibitory signaling pathway so as to inhibit an anti-tumor adaptive immune reaction. PD-1 overexpression in human tumor-associated macrophages (TAMS) is also proved to be capable of inhibiting phagocytosis and tumor immunity. At present, an anti-PD-1 or anti-PD-L1 monoclonal antibody for blocking PD-1/PD-L1 interaction has remarkable effect in cancer treatment. Although Food and Drug Administration approves the anti-PD-1 or anti-PD-L1 monoclonal antibody such as keytruda, opdivo and tecentriq to be used to treat advanced cancers, these anti-tumor drugs only have reaction on part of patients, and it implies that single blocking of the inhibitory signaling pathway is insufficient to activate an immune response, and there are still other mechanisms to inhibit the immune system.

A lymphocyte activation gene 3 (LAG-3) is a transmembrane protein, and is expressed in the activated T cells, natural killer cells, B cells and plasmacytoid dendritic cells. Like PD-1, LAG-3 is one of immune checkpoint receptors combined with MHC II and negatively regulating T cell receptor signal transduction on APC. Because LAG-3 is also expressed on the Treg cells, LAG-3 blocking can inhibit the activity of the Treg cells and enhance its anti-tumor immune function. Preclinical experiments show that LAG-3 signaling pathway blocking has the anti-tumor effect.

TIGIT, known as T cell immunoglobulin and ITIM domain protein, is an inhibitory receptor containing Ig and ITIM domains shared by T cells and NK cells. TIGIT is highly expressed in T cells and natural killer (NK) cells. TIGIT, CD96, CD226 and related ligands together form an immunomodulatory signaling pathway. Similar to the CD28/CTLA-4 signaling pathway, the CD226/TIGIT/CD96 signaling pathway also contains costimulatory receptors and coinhibitory receptors sharing some or all of the ligands, in which CD226 is a costimulatory receptor and delivers stimulus signals upon combining with ligands, and TIGIT and CD96 are coinhibitory receptors and deliver inhibitory signals upon combining with related ligands. TIGIT has two ligands, i.e. CD155 and CD122, which are also ligands of CD226. These two ligands are expressed in APC cells, T cells and tumor cells. The ligands of CD96 include CD155 and CD111. The affinity of TIGIT with the ligand CD155 is significantly higher than that of TIGIT with the ligand CD122, and also significantly higher than the affinity of CD226 or CD96 with the ligand CD155. Similar to PD-1 and CTLA-4 receptors, TIGIT is also an important inhibitory immune receptor. Inhibition of TIGIT can promote the proliferation and function of T cells; blocking of TIGIT can also enhance the anti-tumor immune response mediated by NK cells, thereby inhibiting tumor growth. Therefore, monoclonal antibodies targeting the inhibitory receptor TIGIT can significantly enhance the effect of tumor immunotherapy.

Currently, with the successful launch of PD-1/PD-L1 antibodies, immunotherapy based on immune checkpoint blockade has been rapidly developed and promoted. However, these antibodies are only effective to a part of patients, and will generate drug resistance. Therefore, how to better combine the cytokines and the antibodies to solve these problems is always a research focus.

SUMMARY

In order to solve the above problems, in one aspect, the present invention provides a monoclonal antibody-cytokine fusion protein dimer, the monoclonal antibody includes two heavy chains, the fusion protein dimer includes a first heavy chain polypeptide chain and a second heavy chain polypeptide chain, where one heavy chain of the monoclonal antibody is connected with a cytokine to form the first heavy chain polypeptide chain, and the other heavy chain of the monoclonal antibody is optionally connected with another cytokine to form the second heavy chain polypeptide chain.

In some embodiments, the monoclonal antibody is an anti-immune checkpoint molecular antibody. Preferably, the monoclonal antibody is selected from an anti-LAG-3 antibody, an anti-PD-L1 antibody, an anti-TIGIT antibody or an anti-PD-1 antibody. In some embodiments, the monoclonal antibody is the anti-LAG-3 antibody. In some other embodiments, the monoclonal antibody is the anti-PD-L1 antibody. In some embodiments, the monoclonal antibody is the anti-TIGIT antibody. In some other embodiments, the monoclonal antibody is the anti-PD-1 antibody.

In some embodiments, the two cytokines are selected from IL-2, IL-12, GM-CSF, an IL-2 mutant and a combination thereof. Preferably, the two cytokines are selected from IL-2, IL-12 or the IL-2 mutant or a combination thereof.

In some embodiments, two subunits P35 and P40 of IL-12 are connected through a linker sequence to form an IL-12 single strand protein so as to exist in the fusion protein dimer. In some specific embodiments, the two subunits P35 and P40 of IL-12 are connected through the linker sequence to form the IL-12 single strand protein connected with one heavy chain of the monoclonal antibody to form the first or second heavy chain polypeptide chain.

In some embodiments, the monoclonal antibody and the cytokines are connected through the linker sequence or directly fused. In some embodiments, the linker sequence is selected from $(S(G4S)_{1-3})$ (SEQ ID NO:64), $(G4S)_{1-3}$ (SEQ ID NO:65), KRVAPELLGGPS (SEQ ID NO: 66), ASTKG (SEQ ID NO:67), NSPPAA (SEQ ID NO:68), EPKSSDKTHTSPPSP (SEQ ID NO: 69), ERKSSVESPPSP (SEQ ID NO:70) and ESKYGPPSPPSP (SEQ ID NO:71). Preferably, the linker sequence is $(S(G4S)_{1-3})$ (SEQ ID NO:64). More preferably, the linker sequence is $(S(G4S)_3)$ (SEQ ID NO:63).

In some embodiments, the monoclonal antibody is connected with the cytokines through Fc regions of the heavy chains. In some embodiments, the Fc regions of the two heavy chains of the monoclonal antibody are different and have an asymmetric complementary structure therebetween. The asymmetric complementary structure may be, for example, formed through a knobs-into-holes (KiH) technology. Preferably, the Fc regions of the two heavy chains of the monoclonal antibody have mutation combinations selected from a mutation combination T366W/S354C and a mutation combination T366S/L368A/Y407V/Y349C. In some specific embodiments, the Fc region of any heavy chain of the monoclonal antibody has the mutation combination T366W/S354C, and the Fc region of the other complementary heavy chain has the mutation combination T366S/L368A/Y407V/Y349C. In some specific embodiments, the Fc regions of the heavy chains of the monoclonal antibody are selected from a human IgG1 mutant and a human IgG4 mutant.

In some embodiments, one heavy chain of the monoclonal antibody is connected with the cytokine IL-12 to form the first heavy chain polypeptide chain, and the other heavy chain of the monoclonal antibody is connected with the cytokine IL-2 or IL-2 mutant to form the second heavy chain polypeptide chain; or one heavy chain of the monoclonal antibody is connected with the cytokine IL-2 or IL-2 mutant to form the first heavy chain polypeptide chain, and the other heavy chain of the monoclonal antibody is connected with the cytokine IL-12 to form the second heavy chain polypeptide chain. In some embodiments, one heavy chain of the monoclonal antibody is connected with the cytokine IL-12, IL-2 or IL-2 mutant to form the first heavy chain polypeptide chain, and the other heavy chain of the monoclonal antibody is not connected with the cytokine to serve as the second heavy chain polypeptide chain. In some embodiments, one heavy chain of the monoclonal antibody is connected with the cytokine IL-12 to form the first heavy chain polypeptide chain, and the other heavy chain of the monoclonal antibody is not connected with the cytokine to serve as the second heavy chain polypeptide chain. In some embodiments, one heavy chain of the monoclonal antibody is connected with the cytokine IL-2 or IL-2 mutant to form the first heavy chain polypeptide chain, and the other heavy chain of the monoclonal antibody is not connected with the cytokine to serve as the second heavy chain polypeptide chain.

In some embodiments, the cytokines are connected to a C-terminus of the heavy chain Fc regions of the monoclonal antibody through the linker sequence. In some other embodiments, the cytokines are directly connected to the C-terminus of the heavy chain Fc regions of the monoclonal antibody.

In some embodiments, a heavy chain of the anti-LAG-3 monoclonal antibody has a sequence with at least 80%, 85%, 90%, 95%, 96%, 97%, 98% or 99% identity with an amino acid sequence shown in SEQ ID NOs: 8, 12 or 14, and a light chain of the anti-LAG-3 monoclonal antibody has a sequence with at least 80%, 85%, 90%, 95%, 96%, 97%, 98% or 99% identity with an amino acid sequence shown in SEQ ID NO:10. In some specific embodiments, the heavy chain of the anti-LAG-3 monoclonal antibody has the amino acid sequence as shown in SEQ ID NOs: 8, 12 or 14, and the light chain of the anti-LAG-3 monoclonal antibody has the amino acid sequence as shown in SEQ ID NO:10.

In some embodiments, a heavy chain of the anti-PD-L1 monoclonal antibody has a sequence with at least 80%, 85%, 90%, 95%, 96%, 97%, 98% or 99% identity with an amino acid sequence shown in SEQ ID NOs: 22, 26 or 28, and a light chain of the anti-PD-L1 monoclonal antibody has a sequence with at least 80%, 85%, 90%, 95%, 96%, 97%, 98% or 99% identity with an amino acid sequence shown in SEQ ID NO:24. In some embodiments, the heavy chain of the anti-PD-L1 monoclonal antibody has the amino acid sequence as shown in SEQ ID NOs: 22, 26 or 28, and the light chain of the anti-PD-L1 monoclonal antibody has the amino acid sequence as shown in SEQ ID NO:24.

In some embodiments, a heavy chain of the anti-TIGIT monoclonal antibody has a sequence with at least 80%, 85%, 90%, 95%, 96%, 97%, 98% or 99% identity with an amino acid sequence shown in SEQ ID NOs: 36, 40 or 42, and a light chain of the anti-TIGIT monoclonal antibody has a sequence with at least 80%, 85%, 90%, 95%, 96%, 97%, 98% or 99% identity with an amino acid sequence shown in SEQ ID NO:38. In some embodiments, the heavy chain of the anti-TIGIT monoclonal antibody has the amino acid sequence as shown in SEQ ID NOs: 36, 40 or 42, and the light chain of the anti-TIGIT monoclonal antibody has the amino acid sequence as shown in SEQ ID NO:38.

In some embodiments, a heavy chain of the anti-PD-1 monoclonal antibody has a sequence with at least 80%, 85%, 90%, 95%, 96%, 97%, 98% or 99% identity with an amino acid sequence shown in SEQ ID NOs: 50, 54 or 56, and a light chain of the anti-PD-1 monoclonal antibody has a sequence with at least 80%, 85%, 90%, 95%, 96%, 97%, 98% or 99% identity with an amino acid sequence shown in SEQ ID NO:52. In some embodiments, the heavy chain of the anti-PD-1 monoclonal antibody has the amino acid sequence as shown in SEQ ID NOs: 50, 54 or 56, and the light chain of the anti-PD-1 monoclonal antibody has the amino acid sequence as shown in SEQ ID NO:52.

In some embodiments, the IL-12 single strand protein has an amino acid sequence as shown in SEQ ID NO:4.

In some embodiments, IL-2 has an amino acid sequence as shown in SEQ ID NO:8.

The fusion protein dimer provided by the present invention includes two light chains of the monoclonal antibody.

In some embodiments, the first and second heavy chain polypeptide chains of the fusion protein are selected from sequences with at least 80%, 85%, 90%, 95%, 96%, 97%, 98% or 99% identity with an amino acid sequence shown in SEQ ID NOs: 12, 14, 16, 18, 20, 26, 28, 30, 32, 34, 40, 42, 44, 46, 48, 54, 56, 58, 60 or 62. In some specific embodiments, the first and second heavy chain polypeptide chains of the fusion protein are selected from an amino acid sequence as shown in SEQ ID NOs: 12, 14, 16, 18, 20, 26, 28, 30, 32, 34, 40, 42, 44, 46, 48, 54, 56, 58, 60 or 62.

In some embodiments, the monoclonal antibody is the anti-LAG-3 antibody, and the first and second heavy chain polypeptide chains are selected from sequences with at least 80%, 85%, 90%, 95%, 96%, 97%, 98% or 99% identity with an amino acid sequence shown in SEQ ID NOs: 12, 14, 16, 18 or 20. In some specific embodiments, the monoclonal antibody is the anti-LAG-3 antibody, and the first and second heavy chain polypeptide chains are selected from the amino acid sequence shown in SEQ ID NOs: 12, 14, 16, 18 or 20. In some specific embodiments, the monoclonal antibody is the anti-LAG-3 antibody, where the first heavy chain polypeptide chain has the amino acid sequence as shown in SEQ ID NO:18, and the second heavy chain polypeptide chain has the amino acid sequence as shown in SEQ ID NO: 16; the first heavy chain polypeptide chain has the amino acid sequence as shown in SEQ ID NO:16, and the second heavy chain polypeptide chain has the amino acid sequence as shown in SEQ ID NO: 14; or the first heavy chain polypeptide chain has the amino acid sequence as shown in SEQ ID NO: 20, and the second heavy chain polypeptide chain has the amino acid sequence as shown in SEQ ID NO:14.

In some embodiments, the present invention provides an anti-LAG-3 monoclonal antibody-cytokine fusion protein dimer, including a first heavy chain polypeptide chain, a second heavy chain polypeptide chain and two light chains of an anti-LAG-3 antibody, where the first heavy chain polypeptide chain has the amino acid sequence as shown in SEQ ID NO:18, the second heavy chain polypeptide chain has the amino acid sequence as shown in SEQ ID NO: 16, and the light chains have the amino acid sequence as shown in SEQ ID NO:8. In some other embodiments, the present invention provides an anti-LAG-3 monoclonal antibody-cytokine fusion protein dimer, including a first heavy chain polypeptide chain, a second heavy chain polypeptide chain and two light chains of an anti-LAG-3 antibody, where the first heavy chain polypeptide chain has the amino acid sequence as shown in SEQ ID NO:16, the second heavy chain polypeptide chain has the amino acid sequence as shown in SEQ ID NO:14, and the light chains have the amino acid sequence as shown in SEQ ID NO:8. In another embodiment, the present invention provides an anti-LAG-3 monoclonal antibody-cytokine fusion protein dimer, including a first heavy chain polypeptide chain, a second heavy chain polypeptide chain and two light chains of an anti-LAG-3 antibody, where the first heavy chain polypeptide chain has the amino acid sequence as shown in SEQ ID NO:20, the second heavy chain polypeptide chain has the amino acid sequence as shown in SEQ ID NO:14, and the light chains have the amino acid sequence as shown in SEQ ID NO:8.

In some embodiments, the monoclonal antibody is the anti-PD-L1 antibody, and the first and second heavy chain polypeptide chains are selected from sequences with at least 80%, 85%, 90%, 95%, 96%, 97%, 98% or 99% identity with an amino acid sequence shown in SEQ ID NOs: 26, 28, 30, 32 or 34. In some specific embodiments, the monoclonal antibody is the anti-PD-L1 antibody, and the first and second heavy chain polypeptide chains are selected from the amino acid sequence shown in SEQ ID NOs: 26, 28, 30, 32 or 34. In some specific embodiments, the monoclonal antibody is the anti-PD-L1 antibody, where the first heavy chain polypeptide chain has the amino acid sequence as shown in SEQ ID NO:32, and the second heavy chain polypeptide chain has the amino acid sequence as shown in SEQ ID NO:30; the first heavy chain polypeptide chain has the amino acid sequence as shown in SEQ ID NO:30, and the second heavy chain polypeptide chain has the amino acid sequence as shown in SEQ ID NO:28; or the monoclonal antibody is the anti-PD-L1 antibody, where the first heavy chain polypeptide chain has the amino acid sequence as shown in SEQ ID NO:34, and the second heavy chain polypeptide chain has the amino acid sequence as shown in SEQ ID NO:28.

In some embodiments, the present invention provides an anti-PD-L1 monoclonal antibody-cytokine fusion protein dimer, including a first heavy chain polypeptide chain, a second heavy chain polypeptide chain and two light chains of an anti-PD-L1 antibody, where the first heavy chain polypeptide chain has the amino acid sequence as shown in SEQ ID NO:32, the second heavy chain polypeptide chain has the amino acid sequence as shown in SEQ ID NO: 30, and the light chains have the amino acid sequence as shown in SEQ ID NO:24. In some other embodiments, the present invention provides an anti-PD-L1 monoclonal antibody-cytokine fusion protein dimer, including a first heavy chain polypeptide chain, a second heavy chain polypeptide chain and two light chains of an anti-PD-L1 antibody, where the first heavy chain polypeptide chain has the amino acid sequence as shown in SEQ ID NO:30, the second heavy chain polypeptide chain has the amino acid sequence as shown in SEQ ID NO:28, and the light chains have the amino acid sequence as shown in SEQ ID NO:24. In some more embodiments, the present invention provides an anti-PD-L1 monoclonal antibody-cytokine fusion protein dimer, including a first heavy chain polypeptide chain, a second heavy chain polypeptide chain and two light chains of an anti-PD-L1 antibody, where the first heavy chain polypeptide chain has the amino acid sequence as shown in SEQ ID NO:34, the second heavy chain polypeptide chain has the amino acid sequence as shown in SEQ ID NO:28, and the light chains have the amino acid sequence as shown in SEQ ID NO:24.

In some embodiments, the monoclonal antibody is the anti-TIGIT antibody, and the first and second heavy chain polypeptide chains are selected from sequences with at least 80%, 85%, 90%, 95%, 96%, 97%, 98% or 99% identity with an amino acid sequence shown in SEQ ID NOs: 40, 42, 44, 46 or 48. In some specific embodiments, the monoclonal antibody is the anti-TIGIT antibody, and the first and second heavy chain polypeptide chains are selected from the amino acid sequence shown in SEQ ID NOs: 40, 42, 44, 46 or 48. In some specific embodiments, the monoclonal antibody is the anti-TIGIT antibody, where the first heavy chain polypeptide chain has the amino acid sequence as shown in SEQ ID NO:46, and the second heavy chain polypeptide chain has the amino acid sequence as shown in SEQ ID NO:44; the first heavy chain polypeptide chain has the amino acid sequence as shown in SEQ ID NO:44, and the second heavy chain polypeptide chain has the amino acid sequence as shown in SEQ ID NO:42; or the first heavy chain polypeptide chain has the amino acid sequence as shown in SEQ ID NO: 48, and the second heavy chain polypeptide chain has the amino acid sequence as shown in SEQ ID NO:42.

In some embodiments, the present invention provides an anti-TIGIT monoclonal antibody-cytokine fusion protein dimer, including a first heavy chain polypeptide chain, a second heavy chain polypeptide chain and two light chains of an anti-TIGIT antibody, where the first heavy chain polypeptide chain has the amino acid sequence as shown in SEQ ID NO:46, the second heavy chain polypeptide chain has the amino acid sequence as shown in SEQ ID NO:44, and the light chains have the amino acid sequence as shown in SEQ ID NO:38. In some other embodiments, the present invention provides an anti-TIGIT monoclonal antibody-cytokine fusion protein dimer, including a first heavy chain polypeptide chain, a second heavy chain polypeptide chain and two light chains of an anti-TIGIT antibody, where the first heavy chain polypeptide chain has the amino acid sequence as shown in SEQ ID NO:44, the second heavy chain polypeptide chain has the amino acid sequence as shown in SEQ ID NO:42, and the light chains have the amino acid sequence as shown in SEQ ID NO:38. In some more embodiments, the present invention provides an anti-TIGIT monoclonal antibody-cytokine fusion protein dimer, including a first heavy chain polypeptide chain, a second heavy chain polypeptide chain and two light chains of an anti-TIGIT antibody, where the first heavy chain polypeptide chain has the amino acid sequence as shown in SEQ ID NO:48, the second heavy chain polypeptide chain has the amino acid sequence as shown in SEQ ID NO:42, and the light chains have the amino acid sequence as shown in SEQ ID NO:38.

In some embodiments, the monoclonal antibody is the anti-PD-1 antibody, and the first and second heavy chain polypeptide chains are selected from sequences with at least 80%, 85%, 90%, 95%, 96%, 97%, 98% or 99% identity with an amino acid sequence shown in SEQ ID NOs: 54, 56, 58, 60 or 62. In some specific embodiments, the monoclonal antibody is the anti-PD-1 antibody, and the first and second heavy chain polypeptide chains are selected from the amino acid sequence shown in SEQ ID NOs: 54, 56, 58, 60 or 62. In some specific embodiments, the monoclonal antibody is the anti-PD-1 antibody, where the first heavy chain polypeptide chain has the amino acid sequence as shown in SEQ ID NO:60, and the second heavy chain polypeptide chain has the amino acid sequence as shown in SEQ ID NO:58; the first heavy chain polypeptide chain has the amino acid sequence as shown in SEQ ID NO:58, and the second heavy chain polypeptide chain has the amino acid sequence as shown in SEQ ID NO:56; or the first heavy chain polypeptide chain has the amino acid sequence as shown in SEQ ID NO: 62, and the second heavy chain polypeptide chain has the amino acid sequence as shown in SEQ ID NO:56.

In some embodiments, the present invention provides an anti-PD-1 monoclonal antibody-cytokine fusion protein dimer, including a first heavy chain polypeptide chain, a second heavy chain polypeptide chain and two light chains of an anti-PD-1 antibody, where the first heavy chain polypeptide chain has the amino acid sequence as shown in SEQ ID NO:60, the second heavy chain polypeptide chain has the amino acid sequence as shown in SEQ ID NO:58, and the light chains have the amino acid sequence as shown in SEQ ID NO:52. In some other embodiments, the present invention provides an anti-PD-1 monoclonal antibody-cytokine fusion protein dimer, including a first heavy chain polypeptide chain, a second heavy chain polypeptide chain and two light chains of an anti-PD-1 antibody, where the first heavy chain polypeptide chain has the amino acid sequence as shown in SEQ ID NO:58, the second heavy chain polypeptide chain has the amino acid sequence as shown in SEQ ID NO:56, and the light chains have the amino acid sequence as shown in SEQ ID NO:52. In some more embodiments, the present invention provides an anti-PD-1 monoclonal antibody-cytokine fusion protein dimer, including a first heavy chain polypeptide chain, a second heavy chain polypeptide chain and two light chains of an anti-PD-1 antibody, where the first heavy chain polypeptide chain has the amino acid sequence as shown in SEQ ID NO:62, the second heavy chain polypeptide chain has the amino acid sequence as shown in SEQ ID NO:56, and the light chains have the amino acid sequence as shown in SEQ ID NO:52.

In another aspect, the present invention provides an isolated polynucleotide, encoding a first or second heavy chain polypeptide chain of the fusion protein dimer thereof as described herein.

In some specific embodiments, the polynucleotide has a nucleotide sequence as shown in SEQ ID NO:11, 13, 15, 17, 19, 25, 27, 29, 31, 33, 39, 41, 43, 45, 47, 53, 55, 57, 59 or 61.

In another aspect, the present invention provides an expression vector containing the polynucleotide.

In another aspect, the present invention provides a host cell containing the expression vector.

In another aspect, the present invention provides an application of the fusion protein dimer, polynucleotide, the expression vector or the host cell in the preparation of an anti-tumor drug. In some embodiments, the tumor is melanoma, stomach cancer, renal cancer, Hodgkin lymphoma, head and neck cancer, bladder cancer or non-small cell lung cancer. Preferably, the tumor is melanoma, stomach cancer or renal cancer.

In another aspect, the present invention provides an anti-tumor pharmaceutical composition, where the pharmaceutical composition contains the fusion protein dimer and a pharmaceutically acceptable carrier.

In another aspect, the present invention provides a tumor treating method, comprising administering to the subject a therapeutically effective amount of the fusion protein dimer or the pharmaceutical composition containing the fusion protein dimer.

In some embodiments, the anti-tumor pharmaceutical composition provided by the present invention may be administered to the subject by at least one route selected from the following: parenteral, subcutaneous, intramuscular, intravenous, intra-articular, endobronchial, intra-abdominal, intracapsular, endochondral, endoluminal, intracelial, intracerebellar, intracerebroventricular, intracolonic, intracervical, entogastric, intrahepatic, intramyocardial, endosseous, endopelvic, intrapericardial, intraperitoneal, intrapleural, intraprostatic, intrapulmonary, intrarectal, intrarenal, intraretinal, intraspinal, intrasynovial, intrapleural, intratympanic, intrauterine, intravesical, intravitreous, rapid injection, subconjunctival, transvaginal, transrectal, transbuccal, sublingual, intranasal, intratumoral and transcutaneous. Preferably, the anti-tumor pharmaceutical composition is administered to the subject in an intratumoral or intravenous mode.

DETAILED DESCRIPTION

Figure 1:
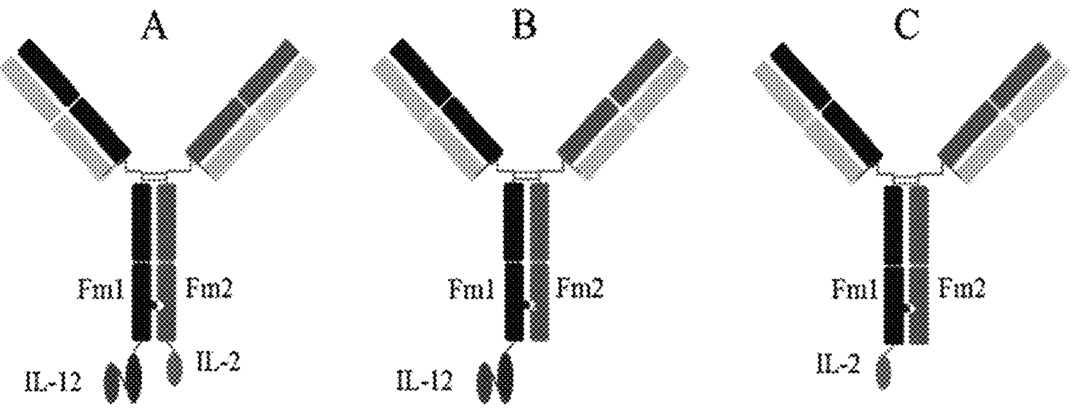
FIG. 1 Structure of monoclonal antibody-cytokine fusion protein dimer
Figure 2:
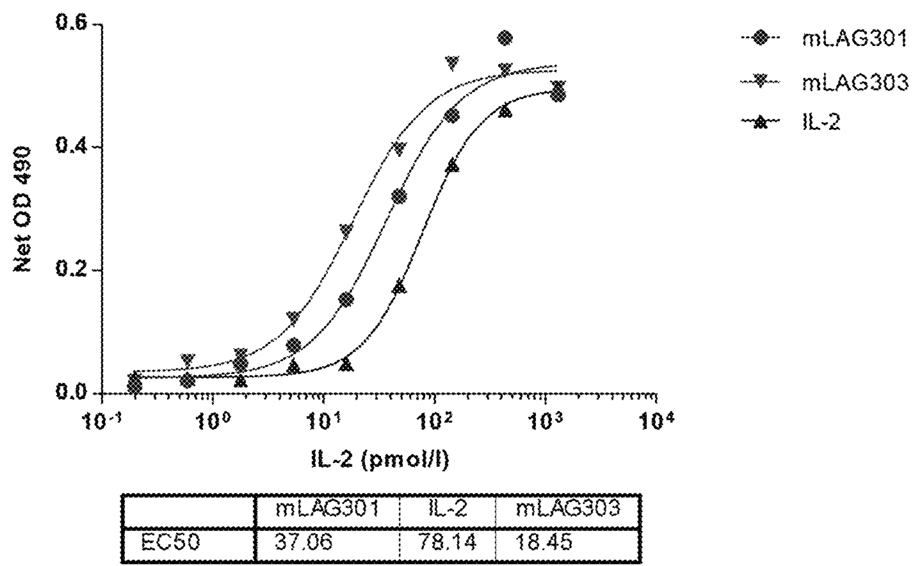
FIG. 2 IL-2 activity detection of an anti-LAG-3 antibody-cytokine fusion protein FIG. 3 IL-2 activity detection of an anti-PD-L1 antibody-cytokine fusion protein FIG. 4 IL-2 activity detection of an anti-TIGIT antibody-cytokine fusion protein FIG. 5 IL-2 activity detection of an anti-PD-1 antibody-cytokine fusion protein FIG. 6 IL-12 activity detection of an anti-LAG-3 antibody-cytokine fusion protein FIG. 7 IL-12 activity detection of an anti-PD-L1 antibody-cytokine fusion protein FIG. 8 IL-12 activity detection of an anti-TIGIT antibody-cytokine fusion protein FIG. 9 IL-12 activity detection of an anti-PD-1 antibody-cytokine fusion protein FIG. 10 Activity detection of LAG-3 blocking of an anti-LAG-3 antibody-cytokine fusion protein FIG. 11 Activity detection of PD-L1 blocking of an anti-PD-L1 antibody-cytokine fusion protein FIG. 12 Activity detection of TIGIT blocking of an anti-TIGIT antibody-cytokine fusion protein FIG. 13 Activity detection of PD-1 blocking of an anti-PD-1 antibody-cytokine fusion protein
Figures 3, 4:
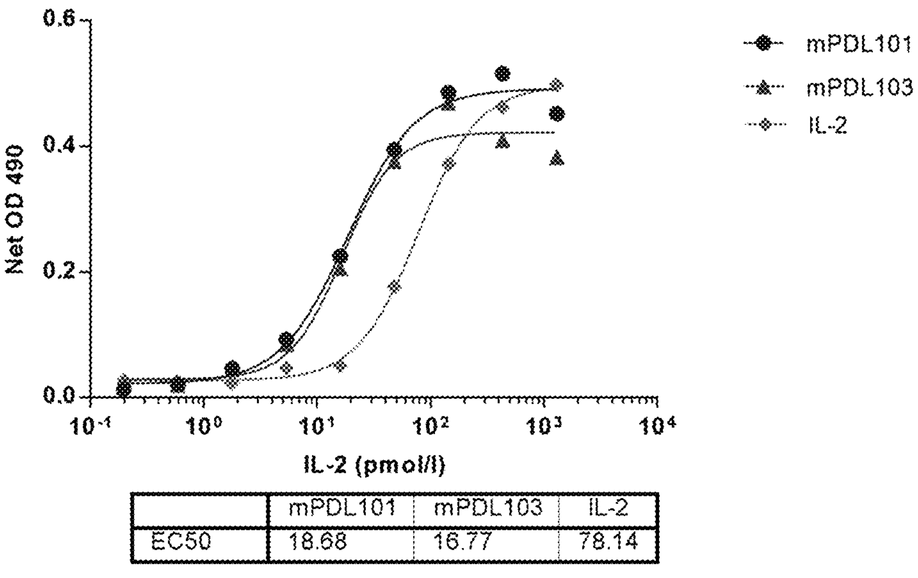
Figure 5:
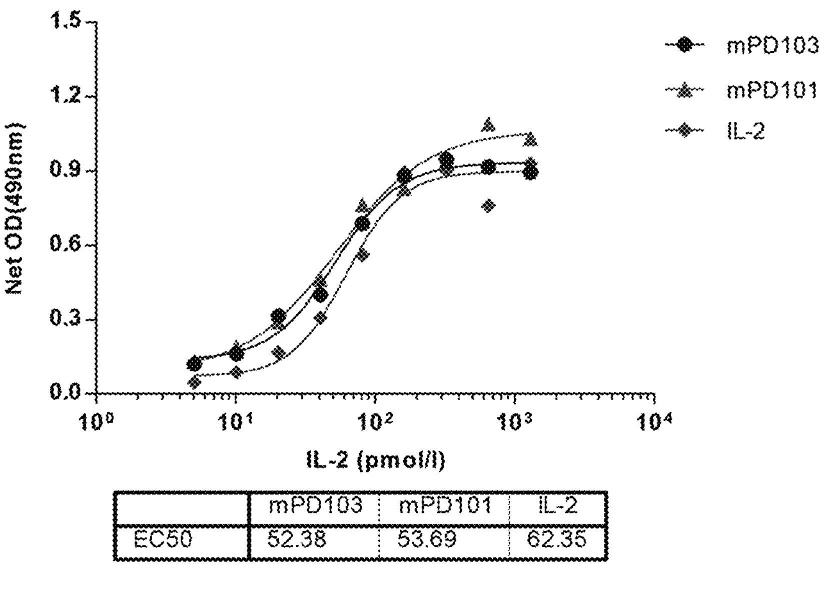
Figure 6:
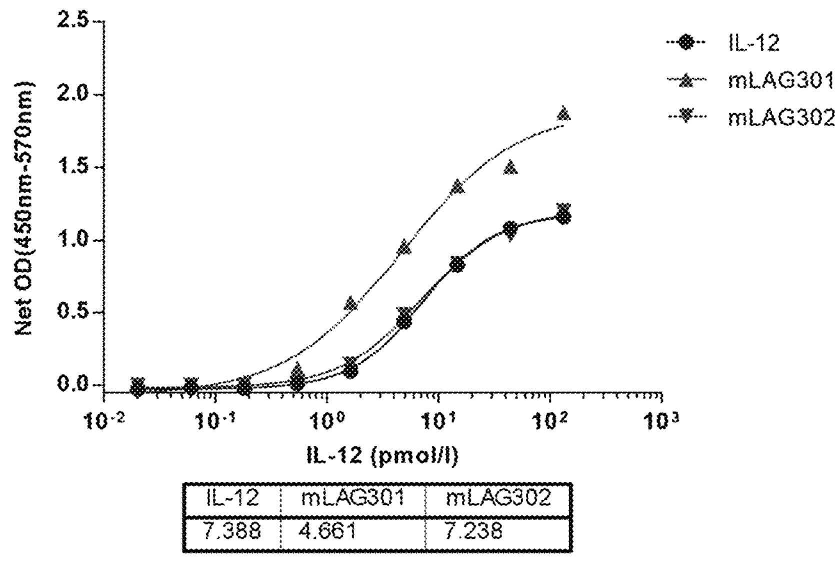
Figures 7, 8:
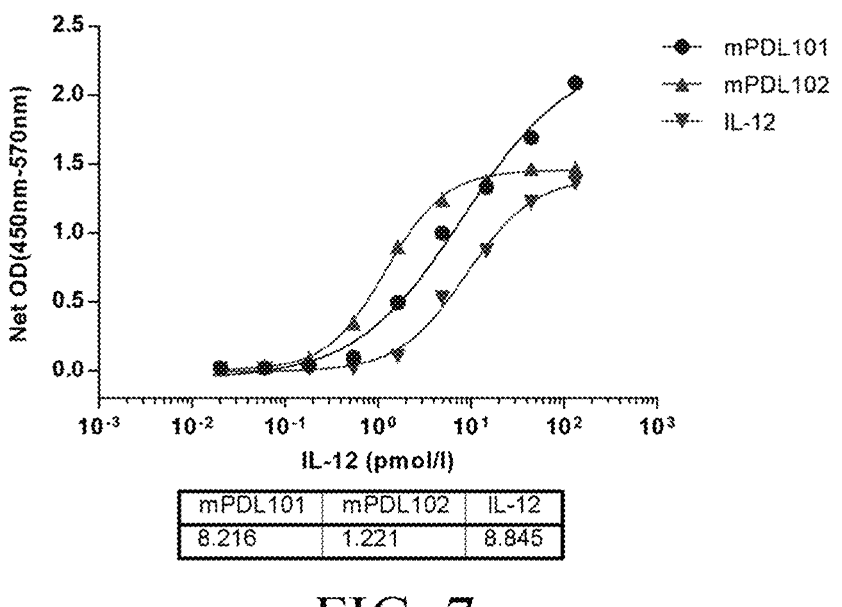
Figure 9:
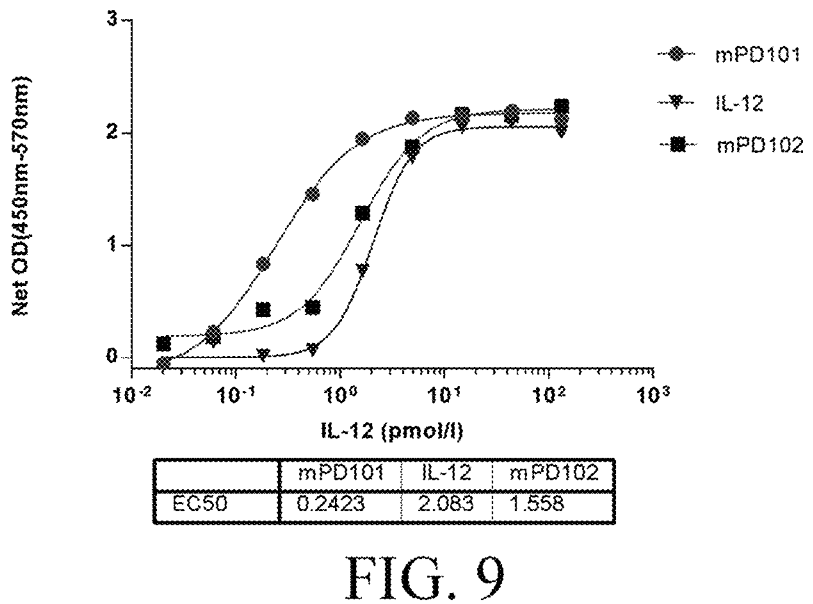

Unless otherwise defined, technical or scientific terms used in the present invention shall have the meanings generally understood by a person skilled in the art to which the present invention pertains.

The present invention provides a fusion protein with anti-tumor activity by utilizing an antibody Fc heterodimer technology, and the fusion protein includes a monoclonal antibody and one or more cytokines. In the present invention, “monoclonal antibody-cytokine fusion protein”, “antibody/cytokine fusion protein” and “McAb-cytokine fusion protein” all refer to the monoclonal antibody-cytokine fusion protein based on the antibody Fc heterodimer technology, including that the one or more cytokines are connected through an antibody heavy chain Fc region to form the fusion protein. Optionally, the monoclonal antibody and the cytokines are connected to a C-terminus of the antibody heavy chain Fc region through a linker sequence.

The term “antibody” refers to a large “Y” shaped protein secreted by a plasmacyte (effector B cells) and used by an immune system to identify and neutralize foreign substances such as bacteria and viruses. In the past more than 10 years, more and more monoclonal antibodies are widely applied to tumor treatment. The antibody usually is a tetramer formed by 2 same heavy chains and 2 same light chains which are mutually connected through disulfide bonds. “anti-immune checkpoint molecular antibody” involved in the present invention refers to an antibody specifically binding to immune checkpoint molecules. The immune checkpoint molecules include but not limited to LAG-3, PD-L1, TIGIT, PD-1 or CTLA-4, and the antibody refers to the monoclonal antibody with the two heavy chains and the two light chains.

The term “antibody Fc region” or “antibody Fc” refers to a shank region of a “Y” shape, namely, a fragment crystallizable (Fc), including second and third constant domains (CH2 and CH3 domains) of the heavy chains. The antibody Fc region may be obtained through hydrolyzing antibody molecules by a proteolytic enzyme (such as papain).

A dimer protein involved in the present invention means that in a protein forming process, if two subunits/monomers are the same, it is called a homodimer (homo-), and if the dimer protein is combined by subunits/monomers which are not exactly the same, it is called a heterodimer (hetero-). The term “antibody Fc heterodimer” means that the protein is combined by the two different subunits/monomers, and each subunit/monomer contains an antibody Fc fragment. The key is that the two antibody Fc fragments have different amino acid site mutations, so that complementary protein spatial structures can be formed, and the two different subunits/monomers can be correctly combined.

The term “knobs-into-holes (KiH) technology” refers to a technology for promoting assembly between two kinds of heterologous antibody heavy chains. For example, a site 366 small-size threonine (T) at a heavy chain CH3 region of one antibody may be mutated into a large-size tyrosine (Y) so as to form a protruding “knobs” type structure (T366Y); meanwhile, a site 407 large tyrosine (Y) residue at a heavy chain CH3 region of another antibody is mutated into a small threonine (T) so as to form a recessed "holes" type structure (Y407T). The two kinds of different antibody heavy chains can be correctly assembled by utilizing a steric-hindrance effect of the "knobs-into-holes" structure (namely, an asymmetric complementary structure). According to the present invention, the better assembly effect is achieved by mutation and combination of a plurality of sites in the two antibody Fc regions.

The term "cytokine (CK)" is a low-molecular-weight soluble protein generated by inducing various cells through an immunogen, a mitogen or other stimulants. In an organism, the cytokine is combined with its specific cell surface receptor to deliver intracellular signals so as to change a cell function, and has the various effects of regulating innate immunity and adaptive immunity, hemocytogenesis, cell growth, APSC pluripotent cells, repairing damaged tissues and the like. Interleukin (such as IL-2 or IL-12) serves as a group of cytokines therein, and regulates an immune response by regulating and controlling the immune system. The cytokines can not only act individually to perform the function, but also can be combined with the antibody to form the antibody-cytokine fusion protein. The new protein form organically combines a unique targeting ability of the antibody with immunoregulation of the cytokines, so as to enhance an immunotherapy effect of the antibody. More importantly, the fused cytokines are transported and enriched to a tumor part through the targeting ability of the antibody, so as to effectively avoid side effects caused by individual using of the high-dose cytokines.

The term "isolated polynucleotide" refers to a polynucleotide not in a natural existing state in the nature, including a polynucleotide isolated from the nature (including the organism bodies), and also including a manually synthetic polynucleotide. The isolated polynucleotide may be a genome DNA, cDNA, mRNA or other synthetic RNAs, or a combination thereof. A plurality of nucleotide sequences used to encode the fusion protein dimer of the present invention and other polypeptide fragments are provided herein. It should be pointed out that the skilled in the art can design nucleotide sequences which are not exactly the same as the nucleotide sequences provided above but encode the same amino acid sequences according to amino acid sequences provided herein and based on codon degeneracy. These changed nucleotide sequences are also included in the scope of the present invention.

When the polynucleotide is involved, the term "vector" refers to any molecule (for example, nucleic acid, plasmid, or virus) used to transfer nucleotide encoding information into host cells. The term "expression vector" refers to a vector suitable for expressing target genes (to-be-expressed nucleotide sequences) in the host cells, and usually includes parts such as the target genes, a promoter, a terminator and a marker gene.

The term "host cell" refers to cells that have been or can be transformed through the nucleotide sequences so as to express the selected target genes. The term includes progeny of parental cells. The progeny has the selected target genes, regardless of whether the progeny is the same as an original parental cell in form or genetic constitution or not. The common host cells include bacterial, yeast and mammalian cells, for example, CHO cells.

As for a pharmaceutical composition, the used term "pharmaceutically acceptable carrier" refers to substances such as a solid or liquid diluent, a filler, an antioxidant and a stabilizer capable of being safely administered. These substances are suitable for human and/or animal drug administration without excessive adverse side effects, and meanwhile are suitable for maintaining activity of drugs or an active agent located thereinto. According to an administration route, various different carriers well known in the art may be administered, including but not limited to saccharides, starch, cellulose and derivatives thereof, maltose, gelatin, talc, calcium sulfate, vegetable oil, synthetic oil, polyols, alginic acid, a phosphatic buffer solution, an emulsifier, isotonic saline, and/or pyrogen-free water. The pharmaceutical composition provided by the present invention may be made into clinically acceptable dosage forms such as powder and injection. The pharmaceutical composition of the present invention may be administered to a subject by using any proper routes, for example, drug administration may be achieved through routes including oral, intravenous injection, intramuscular injection, subcutaneous injection, subperitoneal, rectal, sublingual, or via inhalation and transdermal.

The term "therapeutically effective amount" refers to amount of an active compound enough to cause a biological or medical reaction expected by a clinician in the body of the subject. The "therapeutically effective amount" of the fusion protein of the present invention may be determined by the skilled in the art according to factors including the administration route and the body weight, the age and the state of an illness of the subject. For example, a typical daily dosage range may be 0.01 mg-100 mg of active ingredients per kg of body weight.

The term "amino acid sequence identity" is defined as the percentage of amino acid residues in a candidate sequence that are identical to amino acid residues in a particular peptide or polypeptide sequence obtained by aligning sequences and introducing gaps when necessary to obtain the maximum percent sequence identity without considering any conservative substitutions as portion of the sequence identity. Sequence alignment can be performed in a variety of ways within the skill of the art to determine percent amino acid sequence identity, for example, using publicly available computer software, such as BLAST, BLAST-2, ALIGN, or Megalign (DNASTAR) software. Those skilled in the art can determine the appropriate parameters for measuring the alignment, including any algorithm required to obtain the maximum alignment over the entire length of the sequence being aligned.

The term "and/or" refers to elements before or after the term may exist at the same time, or only one of the elements exist. For example, "A and/or B" may be A and B, only A or only B.

The present invention improves the immunotherapy effect by utilizing advantages of immune cytokines and the monoclonal antibody. The cytokines are fused to the anti-immune checkpoint molecular antibody, such as the anti-LAG-3 antibody, the anti-PD-L1 antibody, the anti-TIGIT antibody, or the C-terminus of the heavy chain Fc region of the anti-PD-1 antibody, so that the protein antibody-cytokine fusion protein dimer aiming at anti-immune checkpoints is developed. The activity of these fusion proteins is evaluated through in-vitro activity analysis. It is found that these fusion protein dimers not only fully retain the biological activity of the antibody, but also significantly improve the biological activity of the cytokines. The cytokines mentioned in the present invention include interleukin, for example, interleukin-2 (IL-2), interleukin-12 (IL-12) and a granulocyte-macrophage colony stimulating factor (GM-CSF), where interleukin-2 and interleukin-12 participate in various links of immunoregulation, so as to enhance the immune response. More importantly, the present invention uses the target specificity of the antibody molecule, so that the immune response of immune cells is enhanced and the toxicity of the cytokines is reduced, and thus, on the premise of enhancing the efficacy of the drug, the safety of the medication is ensured.

Example 1 Design and Construction of a Monoclonal Antibody-Cytokine Fusion Protein and Expression and Purification in CHO Cells Cytokines IL-2 or IL-12 may be connected to a heavy chain C-terminus of a monoclonal antibody through a linker sequence (Ser (Gly4Ser)3) (namely, S (G4S)3, SEQ ID NO:63), and a formed fusion protein keeps the double effects of the antibody and the cytokines. Because the functional IL-12 is constituted by two subunits of p35 and p40, IL-12 will be individually fused onto the antibody Fc in a form of the two subunits, or the two subunits of IL-12 form a single strand protein through the linker sequence (S(G4S)3) firstly, and then are connected to the C-terminus of the monoclonal antibody heavy chain through the linker sequence (S(G4S)3).

In a traditional antibody-cytokine fusion protein structure, the cytokines are connected to two heavy chains or two light chains of the antibody simultaneously so as to exist in a form of a homodimer. However, the pharmacokinetic properties of this fused immune cytokines based on IgG platform is poor. In order to fuse the cytokines into the antibody in a form of a monomer and meanwhile change the proportion of the antibody and the cytokines so as to enhance the targeting ability of the fusion protein, with an antibody heterodimer technology being adopted and based, IL-2 or IL-12 is individually fused into one heavy chain, the other chain is not connected with the cytokines so as to form an IL-12 or IL-2 monomer fusion protein, as shown in FIG. 1B and FIG. 1C respectively, or IL-2 and IL-12 are respectively connected to one heavy chain to generate the fusion protein having IL-2 and IL-12 at the same time, as shown in FIG. 1A.

The core of the antibody heterodimer technology is that the two heavy chains of the monoclonal antibody are transformed respectively to generate an asymmetric complementary structure, so that the two transformed chains can be combined to avoid generation of the homodimer. The principle of transformation is based on the following aspects: hydrophobic/spatial complementation (such as KiH and ZW1), electrostatic complementation (such as DD-KK), a spatial complementation+static electricity interaction (such as EW-RVT), spatial complementation+hydrogen bonding complementation (such as A107), and the like. In the present research, hydrophobic/spatial complementation is adopted to transform the two heavy chains of the monoclonal antibody to form the two different heavy chains, named Fm1 and Fm2 (FIG. 1) respectively, then one cytokine is connected to the C-terminus of one heavy chain, and the other heavy chain is not connected with the cytokine; or one cytokine is connected to the heavy chain Fm1, the other cytokine is connected to the heavy chain Fm2, so that the number of each cytokine contained in the finally formed heterodimer is one, instead of two in the homodimer.

The monoclonal antibody-cytokine fusion protein constructed through the above method will be expressed in CHO-3E7 cells, and then is subjected to Protein A affinity chromatography and molecular sieve purification to obtain the protein used for in-vitro analysis.

Example 2 In-Vitro Activity Analysis Experiment of a Monoclonal Antibody-Cytokine Fusion Protein 2.1: IL-2 Activity Detection:

(1) Cell culture and preparation: a piece of CTLL-2 cells is taken out of a liquid nitrogen container for recovery, and are cultured in a 5% $CO_2$ incubator at 37° C., and the cells after recovery are subjected to secondary and enlarged culture according to a total cell count required by an activity detection experiment design.

(2) Plating: the cultured CTLL-2 cells are sampled and counted, and a moderate amount of cells are taken and inoculated into a 96-well plate.

(3) Sample dilution: the fusion protein solution sample obtained through purification and IL-2 control (100 μg/ml) are subjected to gradient dilution, each sample is provided with 9 concentration gradients, and each concentration is provided with 3 repetition holes.

(4) Sample adding: the fusion protein sample and control are added into the 96-well plate inoculated with the CTLL-2 cells, and incubated for 70 hours in the 5% $CO_2$ incubator at 37° C.

(5) Color developing: the 96-well plate is taken out of the incubator, illuminating lamps of a biosafety cabinet are turned off, light is avoided, a Promega Substrate Cell Titer 96 Aqueous One Solution Reagent reagent is added into each experimental hole, and a reaction is performed for about 3 h at 37° C. under a light avoiding condition. After the reaction is completed, the 96-well plate is placed on a microplate reader, an OD value is detected under a 490 nm wave length.

2.2: IL-12 Activity Detection:

(1) Cell culture and preparation: a piece of NK-92 cells is taken out of a liquid nitrogen container for recovery, and are cultured in a 5% $CO_2$ incubator at 37° C., and the cells after recovery are subjected to secondary and enlarged culture according to a total cell count required by an activity detection experiment design.

(2) Plating: the cultured NK-92 cells are sampled and counted, and a moderate amount of cells are taken and inoculated into the 96-well plate.

(3) Sample dilution: a to-be-detected fusion protein solution sample obtained through purification and IL-12 control (100 μg/ml) are dissolved and subjected to gradient dilution, each sample is provided with 9 concentration gradients, and each concentration is provided with 3 repetition holes.

(4) Sample adding: the fusion protein sample and control are added into the 96-well plate inoculated with the NK-92 cells, and incubated for 24 hours in the 5% $CO_2$ incubator at 37° C.

(5) Sample collection: the 96-well plate is taken out of the incubator, and subjected to 4-degree centrifugation at 3700 rpm for 20 min, a supernatant is absorbed, labeling is performed, and preservation is performed at −20° C.

(6) Detection: the cryopreserved sample is taken out, and a content of human IFN gamma in the sample is detected according to operation steps of a human IFN gamma ELISA MAX™ Standard kit. The 96-well plate is placed on a microplate reader, and an OD value is detected under a 450 nm wave length.

2.3: Testing of Activity of an Anti-PD-1/PD-L1 Antibody-Cytokine Fusion Protein Through PD-1/PD-L1 Pathway Blocking Experiment An experiment for detecting an in-vitro function of an anti-PD-1/PD-L1 McAb-cytokine fusion protein sample uses a PD-1/PD-L1 blocking function report gene kit (PD-1/PD-L1 Blockade Bioassay, a product number of a Promega kit is J1250) from Promega. The detection system of the kit is composed of two kinds of cell lines transformed by genetic engineering. A stimulating cell line is PD-L1 aAPC/CHO-K1 cells, and the cells stably express human PD-L1 and a cell surface protein capable of activating a homologous TCR in a mode independent of antigen. An effector cell line is a Jurkat T cell line, and the cell line stably expresses a luciferase reporter gene induced by human PD-1 and NFAT. When the two types of cells are co-cultured, PD-1/PD-L1 interact to inhibit TCR signal transduction and NFAT-mediated luciferase activity. Adding of the anti-PD-1/PD-L1 antibodies can block combination of PD-1 and PD-L1, so as to activate a TCR signaling pathway, enhance the NFAT-mediated luciferase activity, and generate chemiluminescence.

Firstly, the Jurkat T cells of the effector cell line are laid in the 96-well plate, and then the anti-PD-1/PD-L1 antibody-cytokine fusion protein sample and the PD-L1 aAPC/CHO-K1 cells of the stimulating cell line are added. The system is incubated for 6 hours at 37° C. Then a Bio-Glo™ fluorescent detection reagent is added, and incubation is performed for 5-10 minutes at the room temperature. Finally, a chemiluminescence signal reader is used to read fluorescence signals in the 96-well plate. The experiment uses a form of 8 concentrations and three repetition holes, a relative fluorescence unit serves as a y-axis, and the concentration of the antibody sample serves as an x-axis to draw a four-parameter curve. GraphPad Prism software is used to analyze the curve and obtain an $EC_{50}$ value of the anti-PD-1/PD-L1 antibody-cytokine fusion protein sample.

2.4: In-Vitro Activity Analysis of an Anti-TIGIT Antibody-Cytokine Fusion Protein An experiment for detecting an in-vitro function of an anti-TIGIT McAb-cytokine fusion protein sample uses a TIGIT/CD155 blocking function report gene kit (TIGIT/CD155 Blockade Bioassay, a product number of a Promega kit is J2201) from Promega. A detection system of the kit is composed of two kinds of cell lines transformed by genetic engineering. A stimulating cell line is CD155 aAPC/CHO-K1 cells, and the cells express human CD-155 and a cell surface protein capable of activating a homologous TCR complex in a mode independent of antigen. An effector cell line is a Jurkat T cell line, and the cell line expresses human TIGIT and a luciferase reporter gene driven by a natural promoter and generating a response for both TCR activation and CD226 co-stimulation. When the two types of cells are co-cultured, TIGIT inhibits CD226 activation and promoter-mediated luminescence. Adding of the anti-TIGIT antibody can block interaction of TIGIT and CD155 or inhibit an ability of TIGIT for preventing CD226 from forming a homodimer, so as to recover promoter-mediated chemiluminescence.

Firstly, the Jurkat T cells of the effector cell line are laid in the 96-well plate, and then the anti-TIGIT antibody-cytokine fusion protein sample and the CD155 aAPC/CHO-K1 cells of the stimulating cell line are added. The system is incubated for 6 hours at 37° C. Then a Bio-Glo™ fluorescent detection reagent is added, and incubation is performed for 5-10 minutes at the room temperature. Finally, a chemiluminescence signal reader is used to read fluorescence signals in the 96-well plate. The experiment uses a form of 8 concentrations and three repetition holes, a relative fluorescence unit serves as a y-axis, and the concentration of the antibody sample serves as an x-axis to draw a four-parameter curve. GraphPad Prism software is used to analyze the curve and obtain an $EC_{50}$ value of the anti-TIGIT antibody-cytokine fusion protein sample.

2.5: In-Vitro Activity Analysis of an Anti-LAG-3 Antibody-Cytokine Fusion Protein An experiment for detecting an in-vitro function of an anti-LAG3 McAb-cytokine fusion protein sample uses an LAG3 blocking function report gene kit (LAG3 Blockade Bioassay, a product number of a Promega kit is CS194804) from Promega. A detection system of the kit is composed of two kinds of cell lines transformed by genetic engineering. A stimulating cell line is aAPC/Raji cells, and the cells express MHC II and can activate a TCR complex. An effector cell line is a Jurkat T cell line, and the cell line expresses human LAG3 and a luciferase reporter gene driven by a natural promoter and generating a response for TCR activation. When the two types of cells are co-cultured, LAG3 inhibits MHCII activation and promoter-mediated luminescence. Adding of the anti-LAG3 antibody can block interaction of LAG3 and MHCII so as to recover promoter-mediated chemiluminescence.

Firstly, the Jurkat T cells of the effector cell line are laid in the 96-well plate, and then the anti-LAG-3 antibody-cytokine fusion protein sample and the aAPC/Raji cells of the stimulating cell line are added. The system is incubated for 6 hours at 37° C. Then a Bio-Glo™ fluorescent detection reagent is added, and incubation is performed for 5-10 minutes at the room temperature. Finally, a chemiluminescence signal reader is used to read fluorescence signals in the 96-well plate. The experiment uses a form of 8 concentrations and three repetition holes, a relative fluorescence unit serves as a y-axis, and the concentration of the antibody sample serves as an x-axis to draw a four-parameter curve. GraphPad Prism software is used to analyze the curve and obtain an $EC_{50}$ value of the anti-LAG3 antibody-cytokine fusion protein sample.

Experiment Results and Analysis

1. Construction of an Immune Cytokine Fusion Protein Based on a Monoclonal Antibody Heterodimer The research constructs a series of antibody-cytokine fusion proteins based on a monoclonal antibody heterodimer. The components for constructing the fusion proteins are the monoclonal antibody, cytokines IL-12 and IL-2. The present invention adopts the four different monoclonal antibodies for testing whether the technology platform is suitable for most of the monoclonal antibodies or not. The four different monoclonal antibodies are the anti-LAG-3 monoclonal antibody, the anti-PD-L1 monoclonal antibody, the anti-TIGIT monoclonal antibody and the anti-P-1 monoclonal antibody respectively. The anti-LAG-3 monoclonal antibody is Relatlimab from BMS, and belongs to a human IgG4 antibody. The anti-PD-L1 monoclonal antibody is Atezolizumab from Roche, and belongs to a human IgG1 antibody. The anti-TIGIT monoclonal antibody is Tiragolumab from Roche, and belongs to a human IgG1 antibody. The anti-PD-1 monoclonal antibody is from a patent application WO2018119474, and belongs to a human IgG4 antibody.

Firstly, encoding sequences of the heavy chain or the light chain of all the monoclonal antibodies are inserted between multiple cloning sites EcoRI and HindIII of a pTT5 expression vector, and meanwhile, a KOZAK sequence GCCGCCACC and a signal peptide sequence (SEQ ID NO:2) are further added in front of an initiation codon ATG.

In order to generate the heterodimer, a knob-into-holes (KIH) technology is utilized to transform the heavy chain Fc regions of the monoclonal antibodies, a mutation site combination of one heavy chain Fc chain is T366W/S354C, and a mutation site combination of the other heavy chain Fc chain is T366S/L368A/Y407V/Y349C. In addition, if the last amino acid of the C-terminus of the two transformed heavy chains is K, it will also be removed. DNA sequences for encoding IL-12 and IL-2 are connected to the C-terminus of the heavy chains through the linker sequence ($S(G4S)_3$) in a Gibson assembling method respectively, so as to generate plasmids for encoding the fusion protein with the different heavy chains.

As mentioned above, the anti-LAG-3 monoclonal antibody is composed of a heavy chain H1 and a light chain L1. The heavy chain H1 is transformed by the KIH technology to generate 2 heavy chain mutants H2 and H3. The IL-12 sequence is connected to a C-terminus of the heavy chain H2 through the linker sequence (S(G4S)3) to generate a new polypeptide, called H2a. The IL-2 sequence is respectively connected to a C-terminus of the heavy chains H2 and H3 through the linker sequence (S(G4S)3) to generate new polypeptides, called H2b and H3a.

The anti-PD-L1 monoclonal antibody is composed of a heavy chain H4 and a light chain L2. The heavy chain H4 is transformed by the KIH technology to generate 2 heavy chain mutants H5 and H6. The IL-12 sequence is connected to a C-terminus of the heavy chain H5 through the linker sequence (S(G4S)3) to generate a new polypeptide, called H5a. The IL-2 sequence is respectively connected to a C-terminus of the heavy chain H5 and H6 through the linker sequence (S(G4S)3) to generate new polypeptides, called H5b and H6a.

The anti-TIGIT monoclonal antibody is composed of a heavy chain H7 and a light chain L3. The heavy chain H7 is transformed by the KIH technology to generate 2 heavy chain mutants H8 and H9. The IL-12 sequence is connected to a C-terminus of the heavy chain H8 through the linker sequence (S(G4S)3) to generate a new polypeptide, called H8a. The IL-2 sequence is respectively connected to a C-terminus of the heavy chains H8 and H9 through the linker sequence (S(G4S)3) to generate new polypeptides, called H8b and H9a.

The anti-PD-1 monoclonal antibody is composed of a heavy chain H10 and a light chain L4. The heavy chain H10 is transformed by the KIH technology to generate 2 heavy chain mutants H11 and H12. The IL-12 sequence is connected to a C-terminus of the heavy chain H11 through the linker sequence (S(G4S)3) to generate a new polypeptide, called H11a. The IL-2 sequence is respectively connected to a C-terminus of the heavy chains H11 and H12 through the linker sequence (S(G4S)3) to generate new polypeptides, called H11b and H12a.

These constructed fusion proteins are combined with non-transformed parental light chains so as to generate a series of antibody-cytokine fusion proteins. The light chain L1 and the two heavy chains H2a and H3a are combined to generate the antibody-cytokine fusion protein mLAG301, the light chain L1 and the two heavy chains H2a and H3 are combined to generate the antibody-cytokine fusion protein mLAG302, and the light chain L1 and the two heavy chains H2b and H3 are combined to generate the antibody-cytokine fusion protein mLAG303; the light chain L2 and the two heavy chains H5a and H6a are combined to generate the antibody-cytokine fusion protein mPDL101, the light chain L2 and the two heavy chains H5a and H6 are combined to generate the antibody-cytokine fusion protein mPDL102, and the light chain L2 and the two heavy chains H5b and H6 are combined to generate the antibody-cytokine fusion protein mPDL103; the light chain L3 and the two heavy chains H8a and H9a are combined to generate the antibody-cytokine fusion protein mTIGIT01, the light chain L3 and the two heavy chains H8a and H9 are combined to generate the antibody-cytokine fusion protein mTIGIT02, and the light chain L3 and the two heavy chains H8b and H9 are combined to generate the antibody-cytokine fusion protein mTIGIT03; and the light chain L4 and the two heavy chains H11a and H12a are combined to generate the antibody-cytokine fusion protein mPD101, the light chain L4 and the two heavy chains H11a and H12 are combined to generate the antibody-cytokine fusion protein mPD102, and the light chain L4 and the two heavy chains H11b and H12 are combined to generate the antibody-cytokine fusion protein mPD103. The information of the plasmids and the proteins constructed in the experiment is shown in table 1.

TABLE 1

Construction of plasmids and proteins in an antibody-cytokine fusion protein

| Fusion protein | Component | Plasmid | Amino acid sequence SEQ ID NO: |
|---|---|---|---|
| mLAG300 | H1 | pTT5-mLAG3-H | 8 |
| | L1 | pTT5-mLAG3-L | 10 |
| / | H2 | pTT5-mLAG3-H1 | 12 |
| / | H3 | pTT5-mLAG3-H2 | 14 |
| mLAG301 | H2a | pTT5-mLAG3a-IL12 | 16 |
| | H3a | pTT5-mLAG3a-IL2 | 18 |
| | L1 | pTT5-mLAG3-L | 8 |
| mLAG302 | H3 | pTT5-mLAG3-H2 | 14 |
| | H2a | pTT5-mLAG3a-IL12 | 16 |
| | L1 | pTT5-mLAG3-L | 8 |
| mLAG303 | H3 | pTT5-mLAG3-H2 | 14 |
| | H2b | pTT5-mLAG3b-IL2 | 20 |
| | L1 | pTT5-mLAG3-L | 8 |
| mPDL100 | H4 | pTT5-mPDL1-H | 22 |
| | L2 | pTT5-mPDL1-L | 24 |
| / | H5 | pTT5-mPDL1-H1 | 26 |
| / | H6 | pTT5-mPDL1-H2 | 28 |
| mPDL101 | H5a | pTT5-mTIGITa-IL12 | 30 |
| | H6a | pTT5-mTIGITa-IL2 | 32 |
| | L2 | pTT5-mPDL1-L | 24 |
| mPDL102 | H6 | pTT5-mPDL1-H2 | 28 |
| | H5a | pTT5-mTIGITa-IL12 | 30 |
| | L2 | pTT5-mPDL1-L | 24 |
| mPDL103 | H6 | pTT5-mPDL1-H2 | 28 |
| | H5b | pTT5-mTIGITb-IL2 | 34 |
| | L2 | pTT5-mPDL1-L | 24 |
| mTIGIT00 | H7 | pTT5-mTIGIT-H | 36 |
| | L3 | pTT5-mTIGIT-L | 38 |
| / | H8 | pTT5-mTIGIT-H1 | 40 |
| / | H9 | pTT5-mTIGIT-H2 | 42 |
| mTIGIT01 | H8a | pTT5-mTIGITa-IL12 | 44 |
| | H9a | pTT5-mTIGITa-IL2 | 46 |
| | L3 | pTT5-mTIGIT-L | 38 |
| mTIGIT02 | H9 | pTT5-mTIGIT-H2 | 42 |
| | H8a | pTT5-mTIGITa-IL12 | 44 |
| | L3 | pTT5-mTIGIT-L | 38 |
| mTIGIT03 | H9 | pTT5-mTIGIT-H2 | 42 |
| | H8b | pTT5-mTIGITb-IL2 | 48 |
| | L3 | pTT5-mTIGIT-L | 38 |
| mPD100 | H10 | pTT5-mPD1-H | 50 |
| | L4 | pTT5-mPD1-L | 52 |
| / | H11 | pTT5-mPD1-H1 | 54 |
| / | H12 | pTT5-mPD1-H2 | 56 |
| mPD101 | H11a | pTT5-mPD1a-IL12 | 58 |
| | H12a | pTT5-mPD1a-IL2 | 60 |
| | L4 | pTT5-mPD1-L | 52 |
| mPD102 | H12 | pTT5-mPD1-H2 | 56 |
| | H11a | pTT5-mPD1a-IL12 | 58 |
| | L4 | pTT5-mPD1-L | 52 |
| mPD103 | H12 | pTT5-mPD1-H2 | 56 |
| | H11b | pTT5-mPD1b-IL2 | 62 |
| | L4 | pTT5-mPD1-L | 52 |

The above fusion protein plasmids constructed on the pTT5 expression vectors transiently transfect CHO-3E7 cells through a PEI transfection reagent, and then culturing is performed at 37° C. for 6 days. A culture solution supernatant is centrifugally taken, the fusion proteins are first purified through Protein A affinity columns, then a further purification is performed through a molecular sieve, and the final purity reaches 95% or above.

2. Result Analysis of Cytokine Activity Detection

In order to prove broad spectrum of the technological platform of the monoclonal antibody-cytokine fusion protein based on the antibody heterodimer technology, the present invention utilizes the 4 different antibodies to construct the series of antibody-cytokine fusion proteins. As for the antibody-cytokine fusion protein fused with IL-2, compared with biological activity of free IL-2, the activity of IL-2 of all the fusion proteins is obviously enhanced (FIGS. 2, 3, 4, and 5), and this shows that a structure of the monoclonal antibody-cytokine fusion protein based on the antibody heterodimer technology can significantly improve the activity of IL-2.

As for the fusion protein fused with IL-12, compared with biological activity of free IL-12, the activity of IL-12 of the antibody-cytokine fusion proteins constructed by utilizing the 4 different antibodies is enhanced or unchanged (FIGS. 6, 7, 8 and 9). The activity of IL-12 of the fusion protein only fused with IL-2 is kept unchanged, and this shows that the structure of the monoclonal antibody-cytokine fusion protein based on the antibody heterodimer technology can well maintain the activity of IL-12. More importantly, the IL-12 cytokine activity of the antibody-cytokine fusion protein simultaneously fused with IL-12 and IL-2 is higher than the fusion protein only fused with IL-12, this shows that IL-12 and IL-2 may have a synergistic effect, and it is further proved that the structure of the monoclonal antibody-cytokine fusion protein based on the antibody heterodimer technology can significantly improve the activity of IL-12.

3. Result Analysis of Antibody Activity Detection

Figure 10:
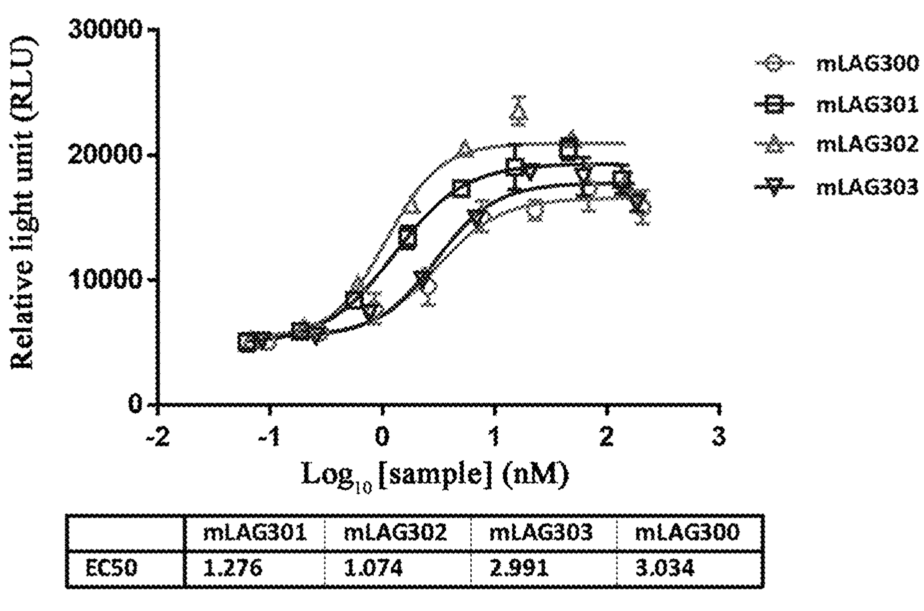
Figure 11:
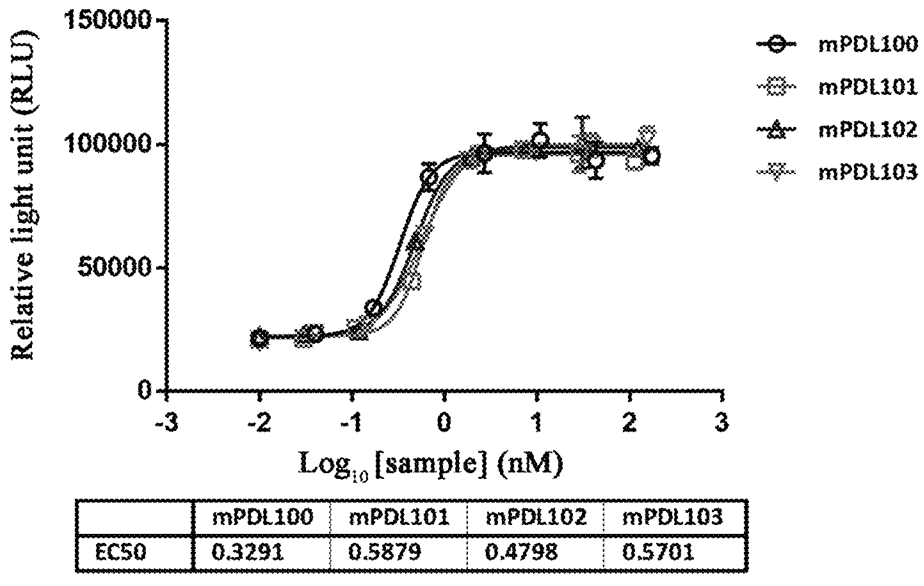
Figure 12:
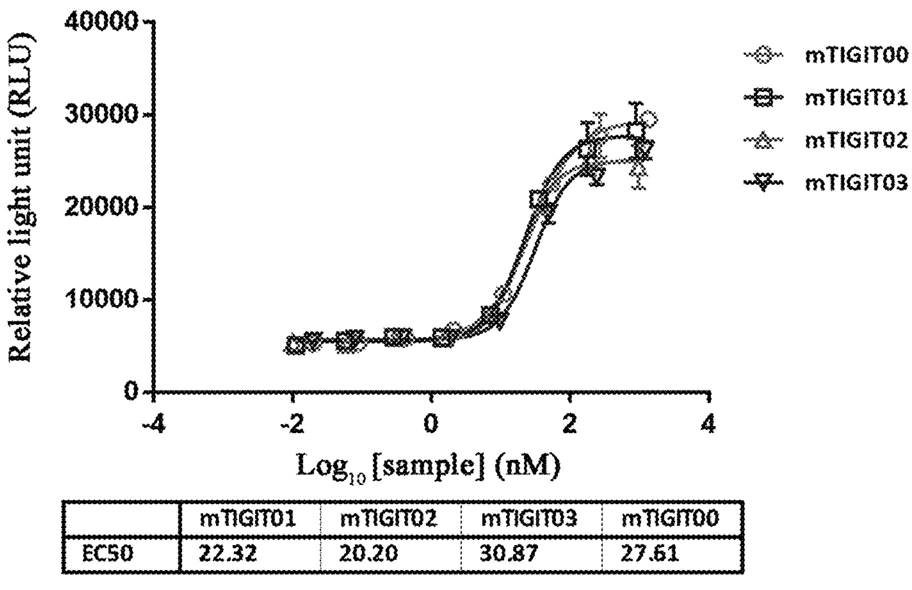
Figure 13:
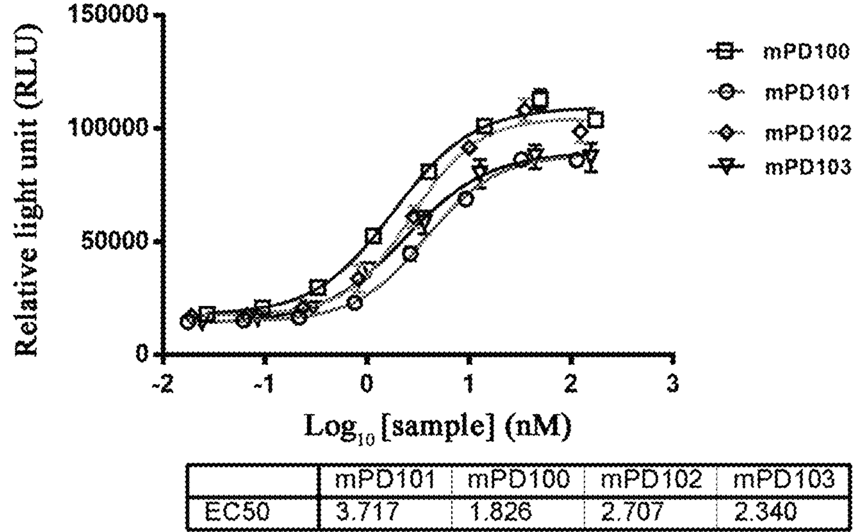

In the present invention, the series of antibody-cytokine fusion proteins are constructed based on the 4 different monoclonal antibodies, and then the antibody activity in each fusion protein is detected by utilizing the antibody activity detection kit of Promega. Results show that compared with untransformed anti-LAG-3 monoclonal antibody control mLAG300, the antibody activity of the constructed heterodimer fusion protein (mLAG303) is almost the same as the control (FIG. 10), and this shows that the antibody-cytokine fusion protein based on the antibody heterodimer technology does not influence exertion of the antibody activity of the fusion protein. More importantly, the antibody activity of the heterodimer fusion protein (mLAG301 and mLAG302) fused with IL-12 is enhanced by 2 times or more than the antibody activity of the monoclonal antibody control (FIG. 10), and this shows that the antibody-cytokine fusion proteins based on the antibody heterodimer technology and fused with IL-12 can significantly enhance the antibody activity of the fusion proteins. Similarly, the antibody activity of the antibody-cytokine fusion protein transformed from the other three monoclonal antibodies (the anti-PD-L1 antibody, the anti-TIGIT antibody, and the anti-PD-1 antibody) is similar to the activity of the respective monoclonal antibody control (mPDL100, mTIGIT00 and mPD100). This shows that the antibody-cytokine fusion proteins based on the antibody heterodimer technology do not influence exertion of the antibody activity, and even enhance the antibody activity of certain fusion proteins.

In conclusion, the present invention develops the novel technological platform of the antibody-cytokine fusion proteins based on the antibody heterodimer technology, constructs the series of antibody-cytokine fusion proteins by utilizing the 4 different antibodies, and verifies that the technological platform can enhance the antibody activity or cytokine activity through a series of antibody and cytokine activity analysis experiments.

A person skilled in the art to which the present invention belongs should understand that the above described methods and materials are only exemplary, and should not be regarded as limitation to the scope of the present invention.

What is claimed is:

1. A monoclonal antibody-cytokine fusion protein dimer, wherein the monoclonal antibody comprises two heavy chains and two associated light chains, the fusion protein dimer comprises a first heavy chain polypeptide chain and a second heavy chain polypeptide chain, wherein one heavy chain of the monoclonal antibody is connected with a cytokine to form the first heavy chain polypeptide chain, and the other heavy chain of the monoclonal antibody is connected with another cytokine to form the second heavy chain polypeptide chain, wherein the monoclonal antibody is a full-length anti-PD-1 antibody, wherein the associated light chains each comprise the amino acid sequence of SEQ ID NO:52, and wherein:

the first heavy chain polypeptide chain comprises the amino acid sequence of SEQ ID NO: 60, and the second heavy chain polypeptide chain comprises the amino acid sequence of SEQ ID NO:58;

the first heavy chain polypeptide chain comprises the amino acid sequence of SEQ ID NO: 58, and the second heavy chain polypeptide chain comprises the amino acid sequence of SEQ ID NO:56; or the first heavy chain polypeptide chain comprises the amino acid sequence of SEQ ID NO: 62, and the second heavy chain polypeptide chain comprises the amino acid sequence of SEQ ID NO:56.

2. The monoclonal antibody-cytokine fusion protein dimer according to claim 1, wherein one heavy chain of the monoclonal antibody is connected with cytokine IL-12 to form the first heavy chain polypeptide chain, and the other heavy chain of the monoclonal antibody is connected with the cytokine IL-2 or an IL-2 mutant to form the second heavy chain polypeptide chain.

3. The monoclonal antibody-cytokine fusion protein dimer according to claim 2, wherein the monoclonal antibody is connected with the cytokines through Fc regions of the heavy chains.

4. The monoclonal antibody-cytokine fusion protein dimer according to claim 3, wherein the Fc regions of the two heavy chains of the monoclonal antibody are different and have an asymmetric complementary structure therebetween.

5. The monoclonal antibody-cytokine fusion protein dimer according to claim 4, wherein the Fc region of any one heavy chain of the monoclonal antibody has a mutation combination T366W/S354C, and the Fc region of the other complementary heavy chain has a mutation combination T366S/L368A/Y407V/Y349C.

6. The monoclonal antibody-cytokine fusion protein dimer according to claim 2, wherein the IL-12 has an amino acid sequence of SEQ ID NO:4.

7. The monoclonal antibody-cytokine fusion protein dimer according to claim 2, wherein the monoclonal antibody and the cytokines are connected through the linker sequence or directly fused.

8. The monoclonal antibody-cytokine fusion protein dimer according to claim 7, wherein the linker sequence is selected from $(S(G_4S)_{1-3})$ (SEQ ID NO:64), $(G_4S)_{1-3}$ (SEQ ID NO:65), KRVAPELLGGPS (SEQ ID NO:66), ASTKG (SEQ ID NO:67), NSPPAA (SEQ ID NO:68), EPKSSDKTHTSPPSP (SEQ ID NO:69), ERKSSVESPPSP (SEQ ID NO:70) and ESKYGPPSPPSP (SEQ ID NO:71).

9. An isolated polynucleotide, encoding the monoclonal antibody-cytokine fusion protein dimer according to claim 2.

10. An expression vector comprising the polynucleotide according to claim 9.

11. A host cell comprising the expression vector of claim 10.

12. An anti-tumor pharmaceutical composition, comprising the monoclonal antibody-cytokine fusion protein dimer according to claim 2 and a pharmaceutically acceptable carrier.

13. An isolated polynucleotide, encoding the monoclonal antibody-cytokine fusion protein dimer according to claim 1.

14. An expression vector comprising the polynucleotide according to claim 13.

15. A host cell comprising the polynucleotide according to claim 13.

16. A method of treating a tumor, comprising administrating to the subject a therapeutically effective amount of the monoclonal antibody-cytokine fusion protein dimer according to claim 2.

* * * * *